United States Patent
Han et al.

(10) Patent No.: US 11,447,489 B2
(45) Date of Patent: Sep. 20, 2022

(54) DIHYDROPYRIMIDINYLTHIAZOLE FOR THE TREATMENT AND PROPHYLAXIS OF HEPATITIS B VIRUS INFECTION

(71) Applicant: Hoffmann-La Roche Inc., Little Falls, NJ (US)

(72) Inventors: Xingchun Han, Shanghai (CN); Min Jiang, Shanghai (CN); Yongguang Wang, Shanghai (CN); Song Yang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 88 days.

(21) Appl. No.: 16/958,658

(22) PCT Filed: Dec. 21, 2018

(86) PCT No.: PCT/EP2018/086473
§ 371 (c)(1),
(2) Date: Jun. 26, 2020

(87) PCT Pub. No.: WO2019/129681
PCT Pub. Date: Jul. 4, 2019

(65) Prior Publication Data
US 2021/0061801 A1     Mar. 4, 2021

(30) Foreign Application Priority Data

Dec. 28, 2017  (CN) .................. PCT/CN2017/119319
Oct. 8, 2018   (CN) .................. PCT/CN2018/109334

(51) Int. Cl.
| *C07D 471/04* | (2006.01) |
| *A61P 31/20* | (2006.01) |
| *C07D 455/06* | (2006.01) |
| *C07D 519/00* | (2006.01) |

(52) U.S. Cl.
CPC ............ *C07D 471/04* (2013.01); *A61P 31/20* (2018.01); *C07D 455/06* (2013.01); *C07D 519/00* (2013.01)

(58) Field of Classification Search
CPC .................................................. C07D 471/04
See application file for complete search history.

(56) References Cited

U.S. PATENT DOCUMENTS

| 2015/0210682 A1 | 7/2015 | Han et al. |
| 2016/0083383 A1 | 3/2016 | Guo et al. |
| 2017/0298067 A1 | 10/2017 | Cheng et al. |

FOREIGN PATENT DOCUMENTS

| WO | 2014/037480 A1 | 3/2014 |
| WO | 2015/113990 A1 | 8/2015 |
| WO | 2015/132276 A1 | 9/2015 |
| WO | 2016/016196 A1 | 2/2016 |
| WO | 2016/177655 A1 | 11/2016 |
| WO | 2017/064156 A1 | 4/2017 |
| WO | 2017/076791 A1 | 5/2017 |

OTHER PUBLICATIONS

"International Preliminary Report on Patentability—PCT/EP2018/086473" (dated Jun. 30, 2020),: 1-8 (Jul. 9, 2020).
"International Search Report—PCT/EP2018/086473":pp. 1-5 (dated Feb. 28, 2019).

*Primary Examiner* — Paul V Ward
(74) *Attorney, Agent, or Firm* — Genentech, Inc.; Richard G. A. Bone

(57) ABSTRACT

The present invention provides novel compounds having the general formula: wherein $R^1$, $R^2$, X, Y and A are as described herein, compositions including the compounds and methods of using the compounds.

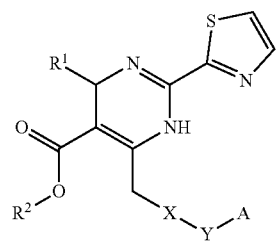

16 Claims, No Drawings

DIHYDROPYRIMIDINYLTHIAZOLE FOR THE TREATMENT AND PROPHYLAXIS OF HEPATITIS B VIRUS INFECTION

The present invention relates to organic compounds useful for therapy and/or prophylaxis in a mammal, and in particular to HBsAg (HBV Surface antigen) inhibitors and HBV DNA production inhibitors useful for treating HBV infection.

FIELD OF THE INVENTION

The present invention relates to novel dihydropyrimidinylthiazole having pharmaceutical activity, their manufacture, pharmaceutical compositions containing them and their potential use as medicaments.

The present invention relates to compounds of formula I

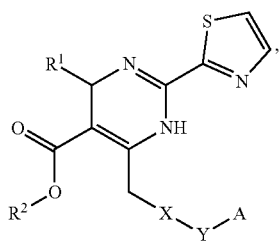

(I)

wherein $R^1$, $R^2$, X, Y and A are as described below, or pharmaceutically acceptable salts, or enantiomers, or diastereomers thereof.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion or to progressive functional impairment (Kondo et al. Journal of Immunology (1993), 150, 4659-4671; Kondo et al. Journal of Medical Virology (2004), 74, 425-433; Fisicaro et al. Gastroenterology, (2010), 138, 682-93. Moreover HBsAg has been reported to suppress the function of immune cells such as monocytes, dendritic cells (DCs) and natural killer (NK) cells by direct interaction (Op den Brouw et al. Immunology, (2009b), 126, 280-9; Woltman et al. PLoS One, (2011), 6, e15324; Shi et al. J Viral Hepat. (2012), 19, e26-33; Kondo et al. ISRN Gasteroenterology, (2013), Article ID 935295).

HBsAg quantification is a significant biomarker for prognosis and treatment response in chronic hepatitis B. However the achievement of HBsAg loss and seroconversion is rarely observed in chronically infected patients but remains the ultimate goal of therapy. Current therapy such as Nucleos(t)ide analogues are molecules that inhibit HBV DNA synthesis but are not directed at reducing HBsAg level. Nucleos(t)ide analogs, even with prolonged therapy, have demonstrated rates of HBsAg clearance comparable to those observed naturally (between −1%-2%) (Janssen et al. Lancet, (2005), 365, 123-9; Marcellin et al. N. Engl. J. Med., (2004), 351, 1206-17; Buster et al. Hepatology, (2007), 46, 388-94). Therefore, there is an unmet medical need to target HBsAg for HBV treatment (Wieland, S. F. & F. V. Chisari. J Virol, (2005), 79, 9369-80; Kumar et al. J Virol, (2011), 85, 987-95; Woltman et al. PLoS One, (2011), 6, e15324; Op den Brouw et al. Immunology, (2009b), 126, 280-9).

SUMMARY OF THE INVENTION

Objects of the present invention are novel compounds of formula I, their manufacture, medicaments based on a compound in accordance with the invention and their production as well as the use of compounds of formula I as HBV inhibitors and for the treatment or prophylaxis of HBV infection. The compounds of formula I show superior anti-HBV activity.

The present invention relates to a compound of formula (I),

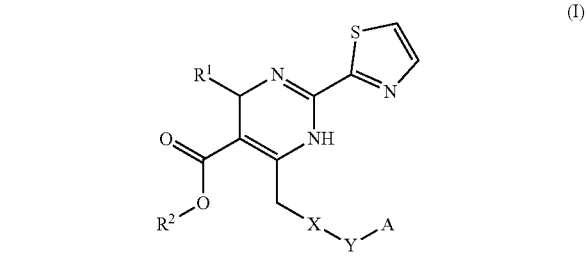

(I)

wherein $R^1$ is phenyl, which is unsubstituted or substituted one or two or three times by halogen or $C_{1-6}$alkyl;

$R^2$ is $C_{1-6}$alkyl;

X is —$(Cy)_{0-1}$-$(L^1)_{0-1}$-$(L^2)_{0-1}$-; wherein

Cy is 3-20 membered heterocyclyl;

$L^1$ is $C_{1-6}$alkyl or carboxy$C_{1-6}$alkyl;

$L^2$ is O, S, —N($R^3$)— or —C(O)—NH—; wherein $R^3$ is H or $C_{1-6}$alkyl;

Y is a bond, $C_{1-9}$alkyl, $C_{1-6}$alkoxy$C_{1-6}$alkoxy$C_{1-6}$alkyl or carboxy$C_{1-9}$alkyl;

A is formula (A1)

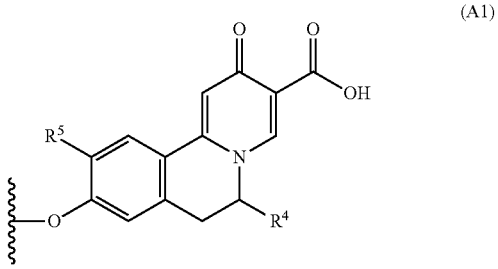

(A1)

wherein
R⁴ is hydrogen or $C_{1-6}$alkyl;
R⁵ is hydrogen or $C_{1-6}$alkoxy;
or formula (A2)

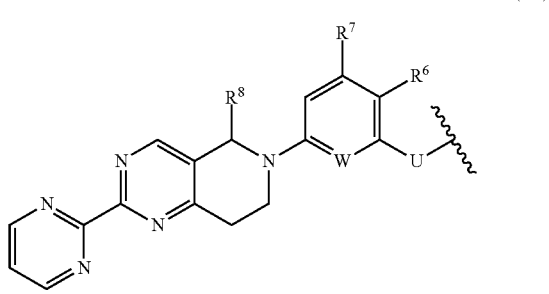

(A2)

wherein
R⁶ is hydrogen or halogen;
R⁷ is hydrogen or halogen;
R⁸ is hydrogen or $C_{1-6}$ alkyl;
is a bond or O;
W is CH or N.
or a pharmaceutically acceptable salt thereof.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise. In some instances dashes ("-") may be used interchangeably within definitions (for example, "alkoxyalkyl" omits the dash found in the equivalent term "alkoxy-alkyl").

When indicating the number of substitutions, the term "one or two or three" refers to the range from one time to the three times number of substitution, i.e. replacement of one hydrogen up to replacement of all hydrogens by substituents. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents.

As used herein, the term "alkyl" signifies a saturated, linear- or branched-chain monovalent hydrocarbon radical of one to nine carbon atoms ($C_1$-$C_9$). In another embodiment, the term "$C_{1-9}$alkyl" signifies a saturated, linear- or branched chain alkyl group containing 1 to 9 carbon atoms. In another embodiment, the term "$C_{1-6}$alkyl" signifies a saturated, linear- or branched chain alkyl group containing 1 to 6 carbon atoms. In another embodiment, an alkyl radical is 1, 2, 3, 4, 5 or 6 carbon atoms, for example methyl, ethyl, propyl, isopropyl, 1-butyl, 2-butyl, tert-butyl, 1-pentyl, 1-hexyl and the like. Particular "alkyl" groups are ethyl, propyl, isopropyl, 1-butyl, 1-pentyl and -hexyl.

As used herein, "heterocyclyl" refer to any mono-, bi-, tricyclic or spiro, saturated or unsaturated, aromatic (heteroaryl) or non-aromatic (e.g., heterocycloalkyl), ring system, having 3 to 20 ring atoms, where the ring atoms are carbon, and at least one atom in the ring or ring system is a heteroatom selected from nitrogen, sulfur or oxygen. If any ring atom of a cyclic system is a heteroatom, that system is a heterocyclyl, regardless of the point of attachment of the cyclic system to the rest of the molecule. In one example, heterocyclyl includes 3-11 ring atoms ("members") and includes monocycles, bicycles, tricycles and spiro ring systems, wherein the ring atoms are carbon, where at least one atom in the ring or ring system is a heteroatom selected from nitrogen, sulfur or oxygen. In one example, heterocyclyl includes 3- to 7-membered monocycles having 1, 2, 3 or 4 heteroatoms selected from nitrogen, sulfur or oxygen. In another example, heterocyclyl includes 4-, 5- or 6-membered monocycles having 1, 2, 3 or 4 heteroatoms selected from nitrogen, sulfur or oxygen. In one example, heterocyclyl includes 8- to 12-membered bicycles having 1, 2, 3, 4, 5 or 6 heteroatoms selected from nitrogen, sulfur or oxygen. In another example, heterocyclyl includes 9- or 10-membered bicycles having 1, 2, 3, 4, 5 or 6 heteroatoms selected from nitrogen, sulfur or oxygen. Exemplary heterocyclyls are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-oxo-5,6,8,8a-tetrahydro-1H-imidazo[1,5-a]pyrazinyl, 3-azabicyclo[3.1.0] hexanyl, 3,6-diazabicyclo[3.1.1]heptanyl, 6-azabicyclo [3.1.1]heptanyl, 3-azabicyclo[3.1.1]heptanyl, 3-azabicyclo [4.1.0]heptanyl, azabicyclo[2.2.2]hexanyl, 2-azabicyclo [3.2.1]octanyl, 8-azabicyclo[3.2.1]octanyl, 2-azabicyclo [2.2.2]octanyl, 8-azabicyclo[2.2.2]octanyl, 7-oxabicyclo [2.2.1 Jheptane, azaspiro [3.5]nonany 1, azaspiro [2.5 Joctany 1, azaspiro [4.5] decanyl, 1-azaspiro [4.5]decan-2-only, azaspiro [5.5 Jundecanyl, 4,5,6,7-tetrahydro[2H]indazolyl, tetrahydrobenzoimidazolyl, 4,5,6,7-tetrahy drobenzo [d] imidazoly 1,1,6-dihydroimidazol [4,5-d]pyrrolo[2,3-b] pyridinyl, tetrahydroindolyl, octahydroindolyl, tetrahydroisoindolyl, tetrahydroindazolyl, 1,1-dioxohexahydrothiopyranyl. Heterocyclyl may be optionally substituted by halogen, OH, SH, CN, $NH_2$, $NHCH_3$, $N(CH_3)_2$, $NO_2$, $N_3$, $C(O)CH_3$, COOH, $CO_2CH_3$, $C_{1-6}$alkyl, $C_{1-6}$alkoxy, oxo, halo$C_{1-6}$alkyl, phenyl or heterocyclyl.

The term "alkoxy" alone or in combination signifies a group alkyl-O—, wherein the "alkyl" is as defined above; for example methoxy, ethoxy, propoxy, iso-propoxy, n-butoxy, iso-butoxy, 2-butoxy, tert-butoxy, pentoxy, hexyloxy and the like. Particular "alkoxy" groups are methoxy, ethoxy and propoxy.

The term "bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

As used herein, the wavy line "⌇" that intersects a bond in a chemical structure refers to the point of attachment of the bond to which the wavy bond intersects in the chemical structure fragment to the remainder of a molecule or structural formula.

As used herein, the representation of a group (e.g., $L^1$) in parenthesis followed by a subscript integer range (e.g., $(L^1)_{0-1}$) means that the group can have the number of occurrences as designated by the integer range. For example, $(L^1)_{0-1}$ means the group $L^1$ can be absent or can occur one time.

The term "halogen" means fluorine, chlorine, bromine or iodine.

The term "carbonyl" alone or in combination refers to the group —C(O)—.

The term "oxo" means an =O group and may be attached to a carbon atom or a sulfur atom.

The term "LG" denotes a leaving group, which is a molecular fragment that departs with a pair of electrons in heterolytic bond cleavage. Leaving groups can be anions or neutral molecules, but in either case it is crucial that the leaving group be able to stabilize the additional electron density that results from bond heterolysis. Common anionic leaving groups are halides, and sulfonate esters such as halogen, OTf, OTs and OMs.

The term "PG" denotes a protecting group, which is introduced into a molecule by chemical modification of a functional group to obtain chemoselectivity in a subsequent chemical reaction. Typical protecting groups are Boc, Cbz and Bn.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitor of HBsAg

The present invention provides (i) a compound having the general formula I:

A compound of the formula (I),

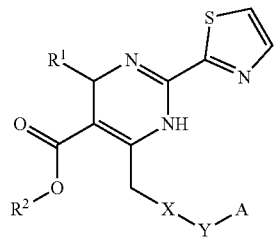

(I)

wherein $R^1$ is phenyl, which is unsubstituted or substituted one or two or three times by halogen or $C_{1-6}$alkyl;

$R^2$ is $C_{1-6}$alkyl;

X is —(Cy)$_{0-1}$-(L$^1$)$_{0-1}$-(L$^2$)$_{0-1}$-; wherein
 Cy is 3-20 membered heterocyclyl;
 $L^1$ is $C_{1-6}$alkyl or carboxy$C_{1-6}$alkyl;
 $L^2$ is O, S, —N(R$^3$)— or —C(O)—NH—; wherein R$^3$ is H or $C_{1-6}$alkyl;

Y is a bond, $C_{1-9}$alkyl, $C_{1-6}$alkoxy$C_{1-6}$alkoxy$C_{1-6}$alkyl or carboxy$C_{1-9}$alkyl;

A is formula (A1)

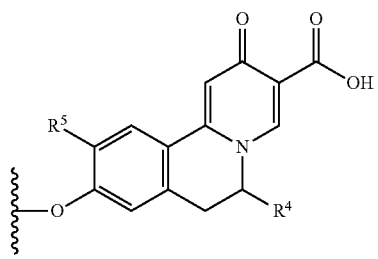

(A1)

wherein $R^4$ is hydrogen or $C_{1-6}$alkyl;

$R^5$ is hydrogen or $C_{1-6}$alkoxy;

or formula (A2)

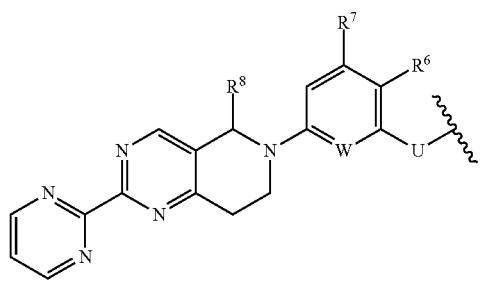

(A2)

wherein $R^6$ is hydrogen or halogen;

$R^7$ is hydrogen or halogen;

$R^8$ is hydrogen or $C_{1-6}$alkyl;

U is a bond or O;

W is CH or N.

or a pharmaceutically acceptable salt thereof.

A further embodiment of the present invention is (ii) a compound of formula I according to embodiment (i), wherein $R^1$ is phenyl, which is one or two or three times substituted by halogen;
$R^2$ is $C_{1-6}$alkyl;
X is —$(Cy)_{0-1}$-$(L^1)_{0-1}$-$(L^2)_{0-1}$-; wherein
  Cy is 5-6 membered monocyclic heterocyclyl or 9-10 membered fused bicyclic heterocyclyl;
  $L^1$ is $C_{1-6}$alkyl or carboxy$C_{1-6}$alkyl;
  $L^2$ is O, S, —N($R^3$)— or —C(O)—NH—; wherein $R^3$ is H or $C_{1-6}$alkyl;
Y is a bond, $C_{1-9}$alkyl, $C_{1-6}$alkoxy$C_{1-6}$alkoxy$C_{1-6}$alkyl or carboxy$C_{1-9}$alkyl;
A is formula (A1), wherein $R^4$ is $C_{1-6}$alkyl, $R^5$ is $C_{1-6}$alkoxy; or formula (A2), wherein $R^6$ is hydrogen or halogen, $R^7$ is halogen, $R^8$ is $C_{1-6}$alkyl, U is a bond or O, W is CH or N;
or a pharmaceutically acceptable salt thereof.

Another embodiment of the present invention is (iii) a compound of formula I according to embodiment (i), wherein $R^1$ is chlorofluorophenyl;
$R^2$ is methyl or ethyl;
X is a bond; O; —N(CH$_3$)—; piperazinyl; carboxypiperazinyl; (aminocarboxy) propylpiperazinyl; (methylamino) methylmorpholinyl; (aminocarbonyl)morpholinyl; 3-oxo-5,6,8,8a-tetrahydro-1H-imidazo[1,5-a]pyrazinyl or (aminocarbonyl)propyl-3-oxo-5,6,8,8a-tetrahydro-1H-imidazo[1,5-a]pyrazinyl;
Y is a bond, hexyl, pentyl, butyl, propyl, (ethoxyethoxy) ethyl or carboxyhexyl;
A is formula (A1), wherein $R^4$ is tert-butyl, $R^5$ is methoxy; or formula (A2), wherein $R^6$ is hydrogen or fluoro, $R^7$ is fluoro, $R^8$ is methyl, U is a bond or O, W is CH or N;
or a pharmaceutically acceptable salt thereof.

A further embodiment of the present invention is (iv) a compound of formula I according to embodiment (i), or pharmaceutically acceptable salt thereof, wherein $R^1$ is phenyl, which is two times substituted by halogen.

Another embodiment of the present invention is (v) a compound of formula I according to embodiment (i), or pharmaceutically acceptable salt thereof, wherein $R^1$ is chlorofluorophenyl.

Another embodiment of the present invention is (vi) a compound of formula I according to embodiment (i), or pharmaceutically acceptable salt thereof, wherein $R^2$ is methyl or ethyl.

A further embodiment of the present invention is (vii) a compound of formula I according to embodiment (i), or pharmaceutically acceptable salt thereof, wherein
X is —$(Cy)_1$-$(L^1)_{0-1}$-$(L^2)_{0-1}$-; wherein Cy is piperazinyl, carboxypiperazinyl, morpholinyl or 3-oxo-5,6,8,8a-tetrahydro-1H-imidazo[1,5-a]pyrazinyl.

Another embodiment of the present invention is (viii) a compound of formula I according to embodiment (i), or pharmaceutically acceptable salt thereof, wherein
X is piperazinyl; carboxypiperazinyl; (aminocarbonyl)propyl-3-oxo-5,6,8,8a-tetrahydro-1H-imidazo[1,5-a]pyrazinyl.

A further embodiment of the present invention is (ix) a compound of formula I according to embodiment (i), or pharmaceutically acceptable salt thereof, wherein Y is a bond, $C_{1-9}$alkyl or $C_{1-6}$alkoxy$C_{1-6}$alkoxy$C_{1-6}$alkyl.

Another embodiment of the present invention is (x) a compound of formula I according to embodiment (i), or pharmaceutically acceptable salt thereof, wherein
Y is a bond; hexyl; propyl; (ethoxyethoxy)ethyl.

Another embodiment of the present invention is (xi) a compound of formula I according to embodiment (i), or pharmaceutically acceptable salt thereof, wherein
A is formula (A1), wherein $R^4$ is tert-butyl, $R^5$ is methoxy; or formula (A2), wherein $R^6$ is hydrogen or fluoro, $R^7$ is fluoro, $R^8$ is methyl, U is a bond or O, W is CH or N.

Any of the above embodiments may be combined.

Particular compounds of formula I according to the invention are the following:

6-tert-butyl-9-[6-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylic acid;

6-tert-butyl-9-[5-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]pentoxy]-10-methoxy-2-oxo-6,7-dihydrobenzo[a]quinolizine-3-carboxylic acid;

6-tert-butyl-9-[4-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]butoxy]-10-methoxy-2-oxo-6,7-dihydrobenzo[a]quinolizine-3-carboxylic acid;

6-tert-butyl-9-[3-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]propoxy]-10-methoxy-2-oxo-6,7-dihydrobenzo[a]quinolizine-3-carboxylic acid;

6-tert-butyl-9-[3-[2-carboxy-4-[[(4R)-4-(2-chloro-4-fluoro-phenyl)-5-methoxycarbonyl-2-thiazol-2-yl-1,4-dihydro-pyrimidin-6-yl]methyl]piperazin-1-yl]propoxy]-10-methoxy-2-oxo-6,7-dihydrobenzo[a]quinolizine-3-carboxylic acid;

6-tert-butyl-9-[6-[3-carboxy-4-[[(4R)-4-(2-chloro-4-fluoro-phenyl)-5-methoxycarbonyl-2-thiazol-2-yl-1,4-dihydro-pyrimidin-6-yl]methyl]piperazin-1-yl]hexoxy]-10-methoxy-2-oxo-6,7-dihydrobenzo[a]quinolizine-3-carboxylic acid;

6-tert-butyl-9-[6-[2-carboxy-4-[[(4R)-4-(2-chloro-4-fluoro-phenyl)-5-methoxycarbonyl-2-thiazol-2-yl-1,4-dihydro-pyrimidin-6-yl]methyl]piperazin-1-yl]hexoxy]-10-methoxy-2-oxo-6,7-dihydrobenzo[a]quinolizine-3-carboxylic acid;

6-tert-butyl-9-[6-[7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]hexoxy]-10-methoxy-2-oxo-6,7-dihydrobenzo[a]quinolizine-3-carboxylic acid;

6-tert-butyl-9-[6-[[(4R)-4-(2-chloro-4-fluoro-phenyl)-5-methoxycarbonyl-2-thiazol-2-yl-1,4-dihydropyrimidin-6-yl]methyl-methyl-amino]hexoxy]-10-methoxy-2-oxo-6,7-dihydrobenzo[a]quinolizine-3-carboxylic acid;

6-tert-butyl-9-[2-[2-[2-[[(3S)-4-[[(4R)-4-(2-chloro-4-fluoro-phenyl)-5-methoxycarbonyl-2-thiazol-2-yl-1,4-dihydropyrimidin-6-yl]methyl]morpholine-3-carbonyl]amino]ethoxy]ethoxy]ethoxy]-10-methoxy-2-oxo-6,7-dihydrobenzo[a]quinolizine-3-carboxylic acid;

6-tert-butyl-9-[2-[2-[2-[2-carboxy-4-[[(4R)-4-(2-chloro-4-fluoro-phenyl)-5-methoxycarbonyl-2-thiazol-2-yl-1,4-dihydropyrimidin-6-yl]methyl]piperazin-1-yl]ethoxy]ethoxy]ethoxy]-10-methoxy-2-oxo-6,7-dihydrobenzo[a]quinolizine-3-carboxylic acid;

6-tert-butyl-9-[4-carboxy-6-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylic acid;

6-tert-butyl-9-[6-[[(3S)-4-[[(4R)-4-(2-chloro-4-fluoro-phenyl)-5-methoxycarbonyl-2-thiazol-2-yl-1,4-dihydropyrimidin-6-yl]methyl]morpholine-3-carbonyl]amino]hexoxy]-10-methoxy-2-oxo-6,7-dihydrobenzo[a]quinolizine-3-carboxylic acid;

6-tert-butyl-9-[6-[[4-(2-chloro-4-fluoro-phenyl)-5-ethoxycarbonyl-2-thiazol-2-yl-1,4-dihydropyrimidin-6-yl]methoxy]hexoxy]-10-methoxy-2-oxo-6,7-dihydrobenzo[a]quinolizine-3-carboxylic acid;

9-[6-[[3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoyl]amino]hexoxy]-6-tert-butyl-10-methoxy-2-oxo-6,7-dihydrobenzo[a]quinolizine-3-carboxylic acid;

9-[6-[[4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoyl]amino]hexoxy]-6-tert-butyl-10-methoxy-2-oxo-6,7-dihydrobenzo[a]quinolizine-3-carboxylic acid;

methyl (4R)-6-[[(8aS)-2-[4-[6-[2,3-difluoro-5-[5-methyl-2-pyrimidin-2-yl-7,8-dihydro-5H-pyrido[4,3-d]pyrimidin-6-yl]phenoxy]hexylamino]-2,2-dimethyl-4-oxo-butyl]-3-oxo-5,6,8,8a-tetrahydro-1H-imidazo[1,5-a]pyrazin-7-yl]methyl]-4-(2-chloro-4-fluoro-phenyl)-2-thiazol-2-yl-1,4-dihydropyrimidine-5-carboxylate;

methyl (4R)-4-(2-chloro-4-fluoro-phenyl)-6-[[(3S)-3-[6-[2,3-difluoro-5-(5-methyl-2-pyrimidin-2-yl-7,8-dihydro-5H-pyrido[4,3-d]pyrimidin-6-yl)phenoxy]hexylcarbamoyl]morpholin-4-yl]methyl]-2-thiazol-2-yl-1,4-dihydropyrimidine-5-carboxylate;

methyl (4R)-4-(2-chloro-4-fluoro-phenyl)-6-[[(3R)-3-[[6-[2,3-difluoro-5-(5-methyl-2-pyrimidin-2-yl-7,8-dihydro-5H-pyrido[4,3-d]pyrimidin-6-yl)phenoxy]hexyl-methyl-amino]methyl]morpholin-4-yl]methyl]-2-thiazol-2-yl-1,4-dihydropyrimidine-5-carboxylate;

methyl (4R)-4-(2-chloro-4-fluoro-phenyl)-6-[[2,3-difluoro-5-(5-methyl-2-pyrimidin-2-yl-7,8-dihydro-5H-pyrido[4,3-d]pyrimidin-6-yl)phenoxy]methyl]-2-thiazol-2-yl-1,4-dihydropyrimidine-5-carboxylate;

(2R)-4-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]-2-[6-[2,3-difluoro-5-(5-methyl-2-pyrimidin-2-yl-7,8-dihydro-5H-pyrido[4,3-d]pyrimidin-6-yl)phenoxy]hexylamino]butanoic acid;

4-[[(4R)-4-(2-chloro-4-fluoro-phenyl)-5-methoxycarbonyl-2-thiazol-2-yl-1,4-dihydropyrimidin-6-yl]methyl]-1-[4-fluoro-6-[5-methyl-2-pyrimidin-2-yl-7,8-dihydro-5H-pyrido[4,3-d]pyrimidin-6-yl]-2-pyridyl]piperazine-2-carboxylic acid;

or a pharmaceutically acceptable salt thereof.

Synthesis

The compounds of the present invention can be prepared by any conventional means. Suitable processes for synthesizing these compounds as well as their starting materials are provided in the schemes below and in the examples. All substituents, in particular, $R^1$, $R^2$ and $R^3$ are as defined above unless otherwise indicated. Furthermore, and unless explicitly otherwise stated, all reactions, reaction conditions, abbreviations and symbols have the meanings well known to a person of ordinary skill in organic chemistry.

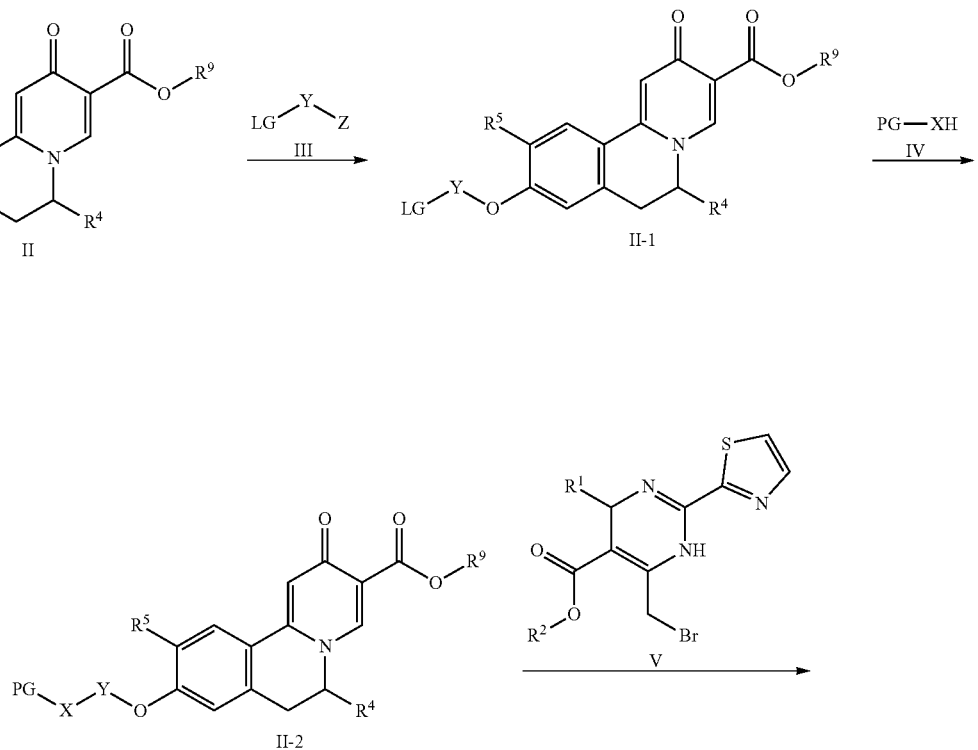

Scheme 1

-continued

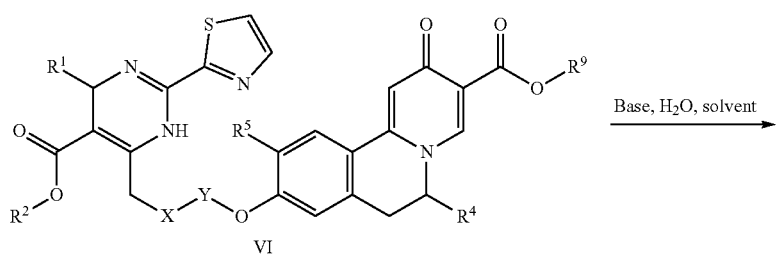

VI

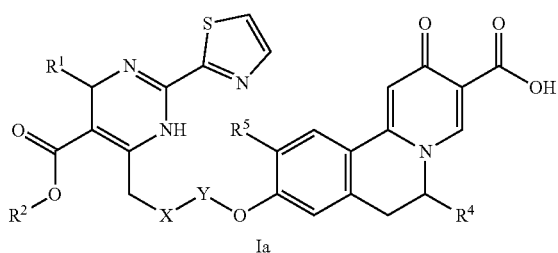

Ia

Wherein Z is halogen; LG is halogen; PG is Boc; $R^9$ is $C_{1-6}$alkyl.

Compound of formula II reacts with a halide III in the presence of a base such as $K_2CO_3$, to give compound of formula II-1, which then reacts with compound of formula IV to give intermediate II-2. De-protection of compound of formula II-2 followed by reaction with bromide V in the presence of a base such as DIPEA, in a solvent such as DMF or DCM, affords compound of formula VI, which is then hydrolyzed with a base such as LiOH or NaOH, in a suitable solvent such as THF/$H_2O$ or MeOH/$H_2O$, to afford compound of formula Ia.

Scheme 2

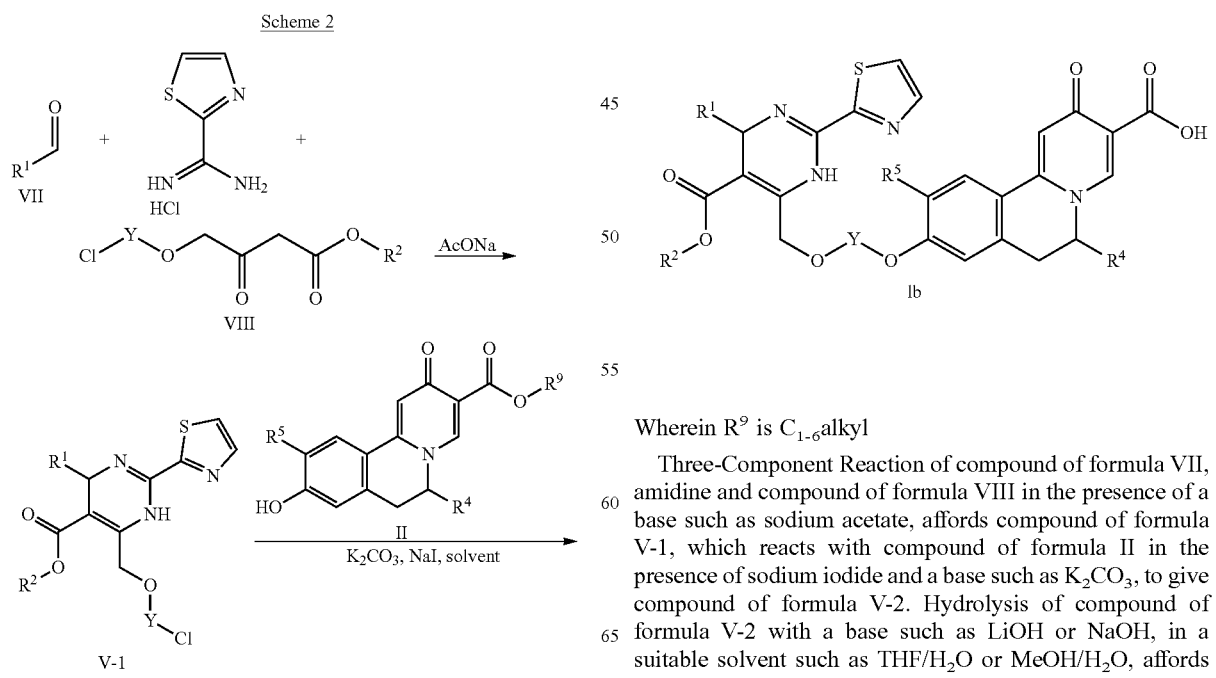

-continued

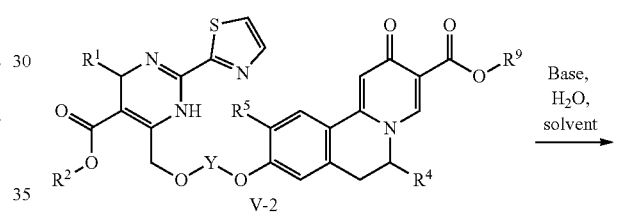

Ib

Wherein $R^9$ is $C_{1-6}$alkyl

Three-Component Reaction of compound of formula VII, amidine and compound of formula VIII in the presence of a base such as sodium acetate, affords compound of formula V-1, which reacts with compound of formula II in the presence of sodium iodide and a base such as $K_2CO_3$, to give compound of formula V-2. Hydrolysis of compound of formula V-2 with a base such as LiOH or NaOH, in a suitable solvent such as THF/$H_2O$ or MeOH/$H_2O$, affords compound of formula Ib.

Scheme 3

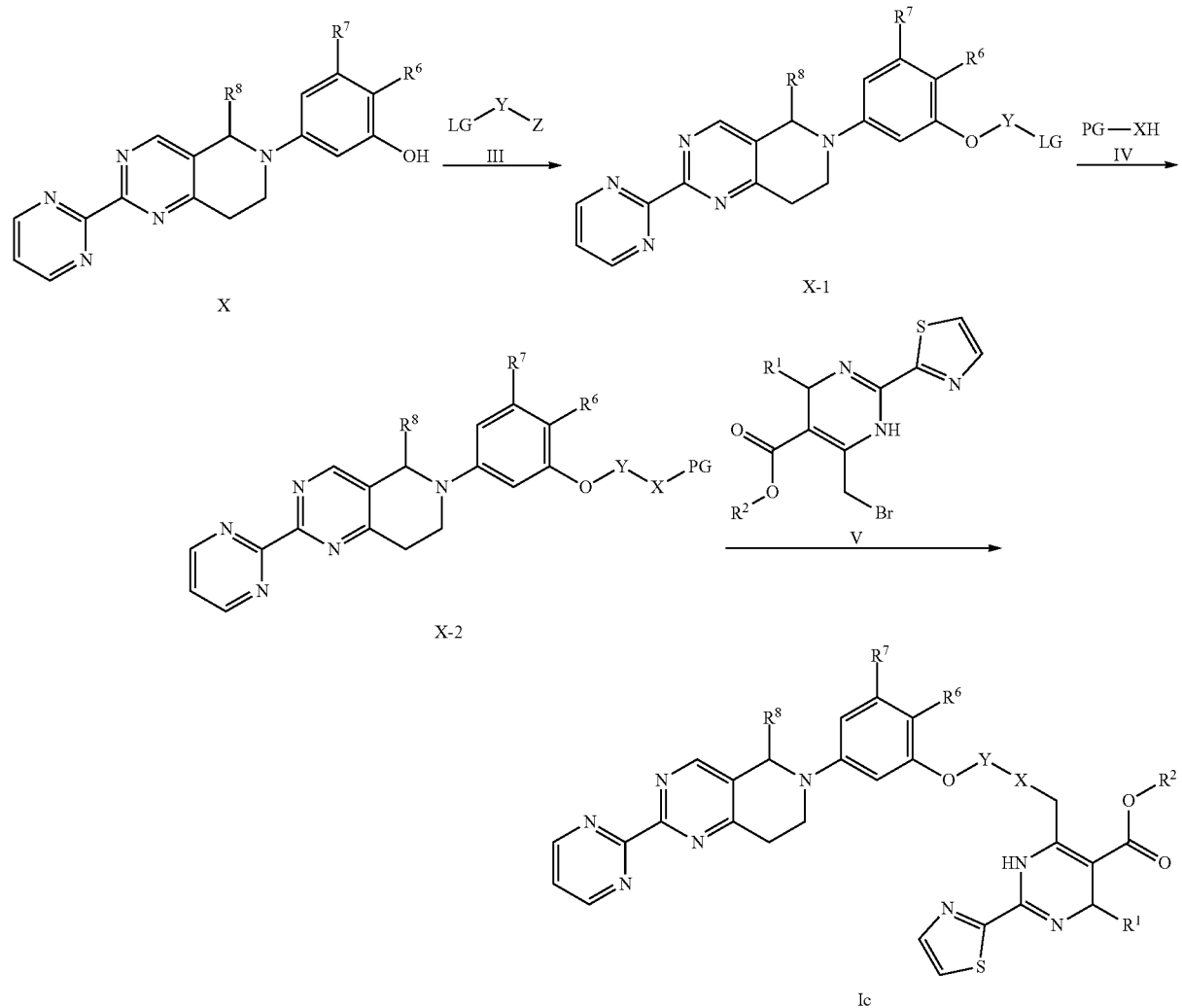

Wherein Z is halogen; LG is leaving group, such as halogen; PG is protecting group, such as Boc.

Phenol X reacts with a halide III in the presence of a base such as K₂CO₃, to give compound of formula X-1, which then reacts with compound of formula IV to give compound of formula X-2. De-protection of compound of formula X-2 followed by reaction with bromide V in the presence of a base such as DIPEA, in a solvent such as DMF or DCM, affords compound of formula Ic.

Scheme 4

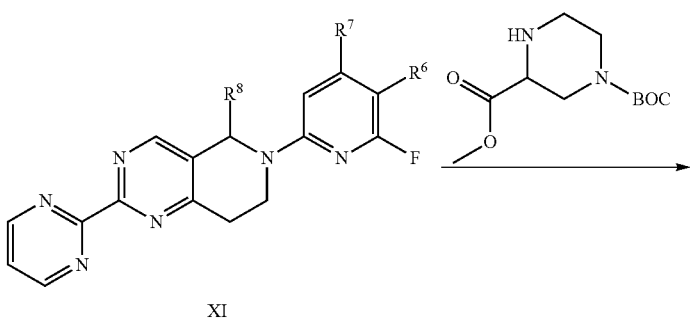

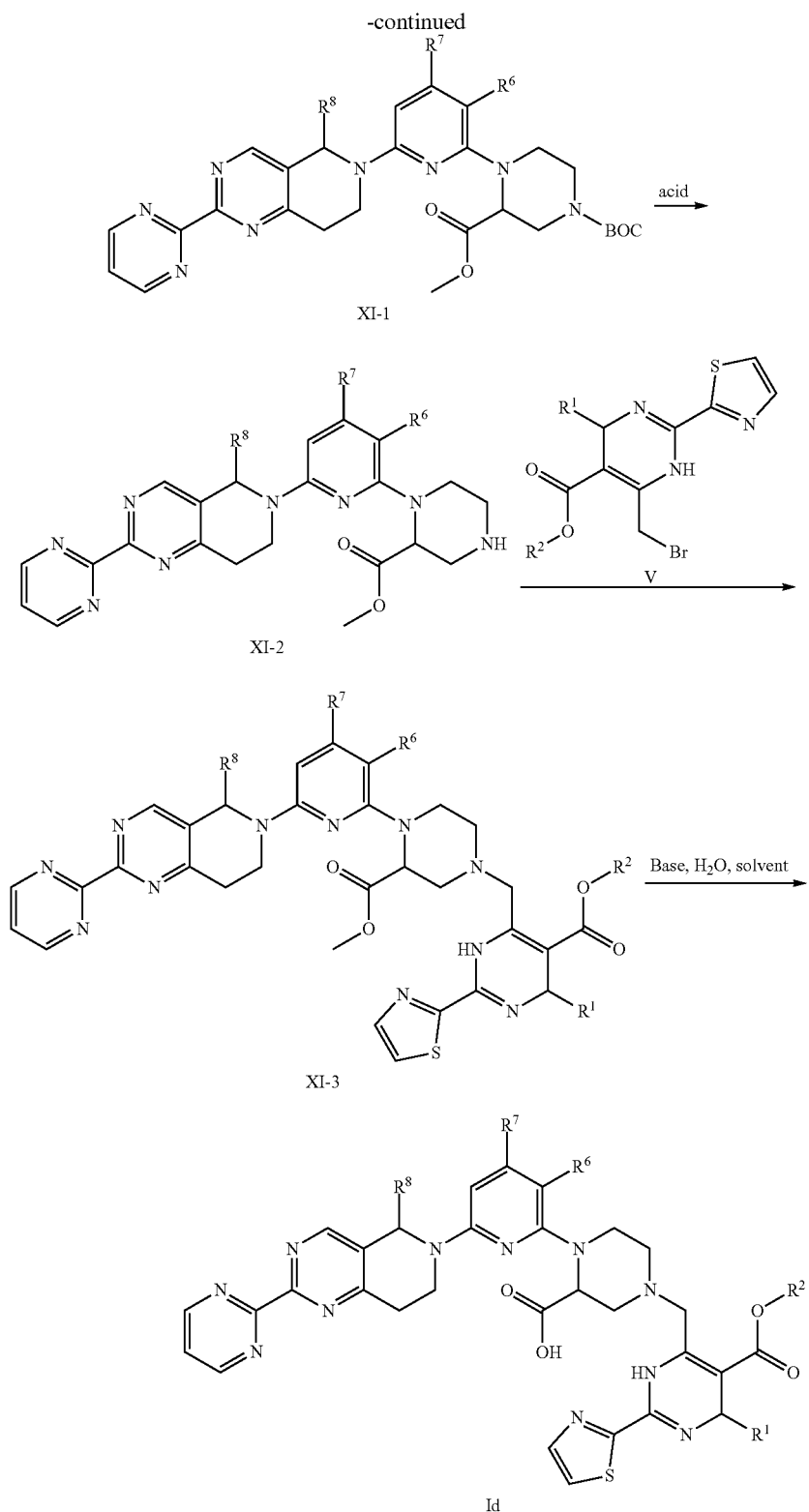

Compound of formula XI is heated with O1-tert-butyl O3-methyl piperazine-1,3-dicarboxylate in the presence of a base such as DIPEA, in a solvent such as DMSO, to give compound of formula XI-1, which is then treated with an acid such as TFA or concentrated HCl, to give compound XI-2. Compound of formula XI-2 reacts with bromide V in the presence of a base such as DIPEA, in a solvent such as DMF or DCM, to afford compound XI-3, which is hydrolyzed with a base such as LiOH or NaOH, in a suitable solvent such as THF/H$_2$O or MeOH/H$_2$O, to afford compound Id.

Scheme 5

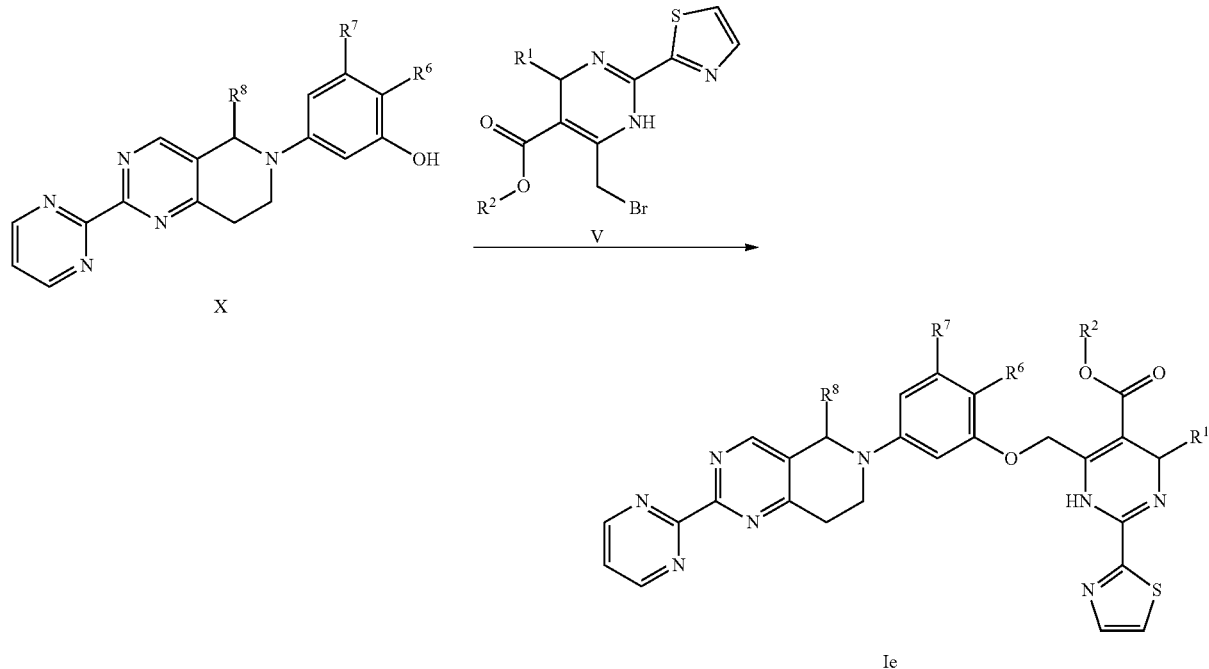

Phenol X reacts with bromide V in the presence of a base such as K$_2$CO$_3$, in a suitable solvent such as DMF, to give compound of formula Ie.

This invention also relates to a process for the preparation of a compound of formula I comprising one of the following steps:
(a) Hydrolysis of compound of formula (VI), (VI)

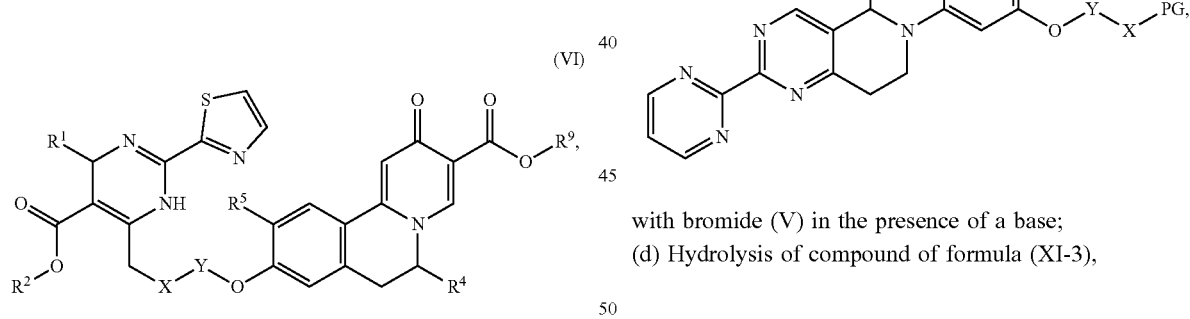

in the presence of a base;
(b) Hydrolysis of compound of formula (V-2), (V-2)

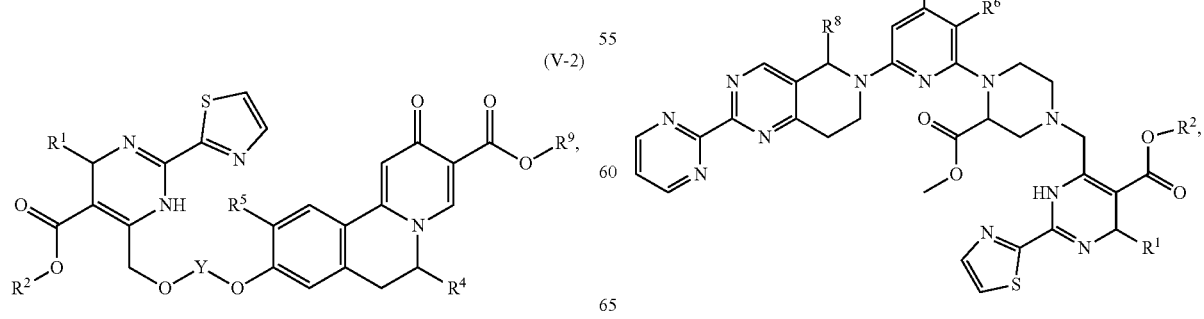

in the presence of a base;

(c) De-protection and Substitution of formula (X-2), (X-2)

with bromide (V) in the presence of a base;
(d) Hydrolysis of compound of formula (XI-3), (XI-3)

in the presence of a base;

(e) Substitution of formula (X),

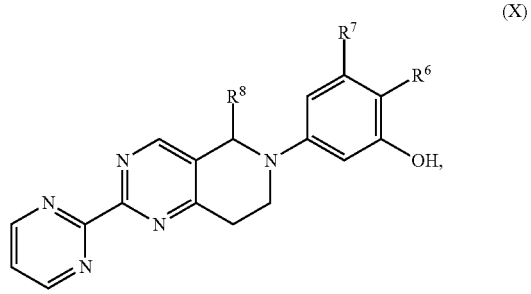

with bromide (V) in the presence of a base;
wherein $R^1$, $R^2$, $R^3$, $R^4$, $R^5$, $R^6$, $R^7$, $R^8$ are defined as above;
Z is Br or I; LG is halogen; PG is Boc; $R^9$ is $C_{1-6}$alkyl;
The base in step (a), (b) or (d), can be for example LiOH or NaOH;
The base in step (c), can be for example DIPEA;
The base in step (e), can be for example $K_2CO_3$;

A compound of formula I when manufactured according to the above process is also an object of the invention.

The compound of this invention also shows good safety and PK profile.

Pharmaceutical Compositions and Administration

The invention also relates to a compound of formula I for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit HBsAg. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.01 to 100 mg/kg of patient body weight per day, with the typical initial range of compound used being 0.3 to 15 mg/kg/day. In another embodiment, oral unit dosage forms, such as tablets and capsules, preferably contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 to 1000 mg of the compound of the invention compounded with about 0 to 2000 mg anhydrous lactose, about 0 to 2000 mg sodium croscarmellose, about 0 to 2000 mg polyvinylpyrrolidone (PVP) K30, and about 0 to 2000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.1 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

Indications and Methods of Treatment

The compounds of the invention can inhibit HBsAg production or secretion and inhibit HBV gene expression. Accordingly, the compounds of the invention are useful for the treatment or prophylaxis of HBV infection.

The invention relates to the use of a compound of formula I for the inhibition of HBsAg production or secretion.

The invention relates to the use of a compound of formula I for the inhibition of HBV DNA production.

The invention relates to the use of a compound of formula I for the inhibition of HBV gene expression.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method for the treatment or prophylaxis of HBV infection, which method comprises administering an effective amount of a compound of Formula I, a stereoisomer, tautomer, prodrug, conjugates or pharmaceutically acceptable salt thereof.

EXAMPLES

The invention will be more fully understood by reference to the following examples. They should not, however, be construed as limiting the scope of the invention.

Abbreviations used herein are as follows:
DIPEA: N,N-diisopropylethylamine
NBS N-bromosuccinimide
TEA triethylamine
THF tetrahydrofuran
DMAP 4-dimethylaminopyridine
HATU 0-(7-aza-1H-benzotriazole-1-yl)-N,N,N',N'-tetramethyluronium hexafluorophosphate
CDI N,N'-carbonyldiimidazole
DMF: dimethylformamide
DMSO-d6: deuterated dimethylsulfoxide
EtOAc: ethyl acetate
h: hour
$IC_{50}$: the half maximal inhibitory concentration
HPLC: high performance liquid chromatography
LC/MS: Liquid chromatography/mass spectrometry
MeOH: methanol
METHANOL-$d_4$: perdeuteromethanol
M: molarity
MHz: megahertz
min: minute
MS (ESI): mass spectroscopy (electron spray ionization)
NMR: nuclear magnetic resonance
obsd. Observed
rt: room temperature
prep-HPLC: preparative high performance liquid chromatography
TFA: trifluoroacetic acid
δ: chemical shift

General Experimental Conditions

Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column or SunFire™ Perp Cis (5 μm, OBD™ 30×100 mm) column.

LC/MS spectra were obtained using an Acquity Ultra Performance LC-3100 Mass Detector or Acquity Ultra Performance LC-SQ Detector. Standard LC/MS conditions were as follows (running time 3 minutes):

Acidic condition: A: 0.1% formic acid in $H_2O$; B: 0.1% formic acid in acetonitrile;

Basic condition: A: 0.05% $NH_3.H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(M+H)^+$.

The microwave assisted reactions were carried out in a Biotage Initiator Sixty or CEM Discover.

NMR Spectra were obtained using Bruker Avance 400 MHz.

All reactions involving air-sensitive reagents were performed under an argon atmosphere. Reagents were used as received from commercial suppliers without further purification unless otherwise noted.

PREPARATIVE EXAMPLES

The invention will be more fully understood by reference to the following examples. They should not, however, be construed as limiting the scope of the invention.

Intermediate I-1 ethyl 6-tert-butyl-9-hydroxy-10-methoxy-2-oxo-6,7-dihydrobenzo[a]quinolizine-3-carboxylate

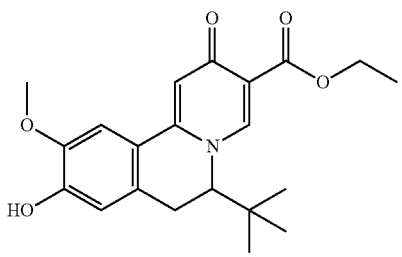

The intermediate I-1 was prepared according to procedure in US20150210682, Example 141.

Intermediate I-2 methyl (4R)-6-(bromomethyl)-4-(2-chloro-4-fluorophenyl)-2-thiazol-2-yl-1,4-dihydropyrimidine-5-carboxylate

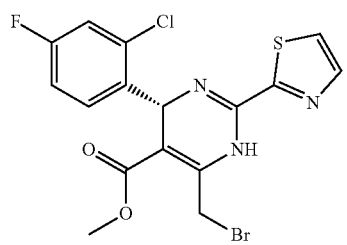

The title compound was prepared according to the following scheme:

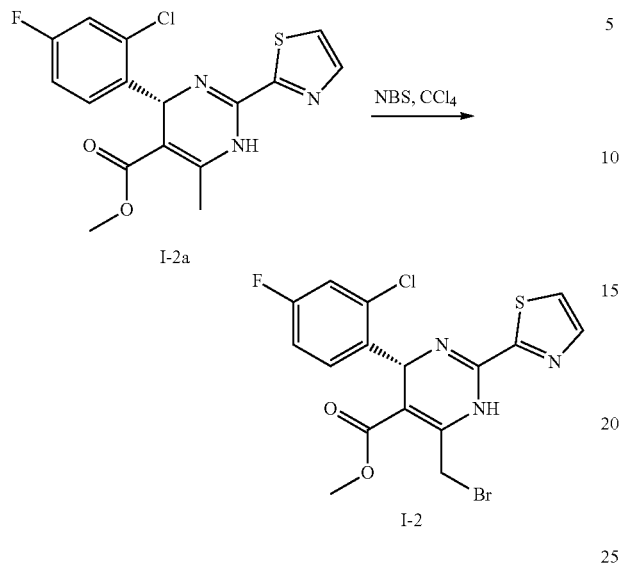

Preparation of methyl (4R)-6-(bromomethyl)-4-(2-chloro-4-fluoro-phenyl)-2-thiazol-2-yl-1,4-dihydropyrimidine-5-carboxylate (Intermediate I-2)

To a stirred solution of methyl (4R)-4-(2-chloro-4-fluorophenyl)-6-methyl-2-thiazol-2-yl-1,4-dihydropyrimidine-5-carboxylate (0.37 g, 1.0 mmol, prepared according to WO2016016196) in CCl$_4$ (5 mL) was added NBS (0.20 g, 1.1 mmol) in portions. After the reaction mixture was stirred at room temperature for 1 hour, the solvent was removed under reduced pressure and the residue was purified by column chromatography to give intermediate I-2 as a yellow solid. MS oms. (ESI$^+$) [(M+H)$^+$]: 444.

Intermediate I-3 tert-butyl 3-oxo-1,2,5,6,8,8a-hexahydroimidazo[1,5-a]pyrazine-7-carboxylate

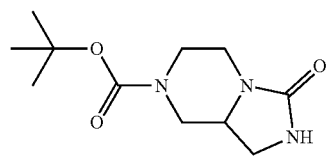

The title compound was prepared according to the following scheme:

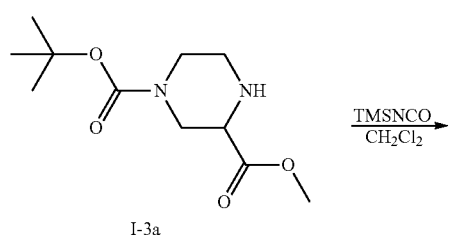

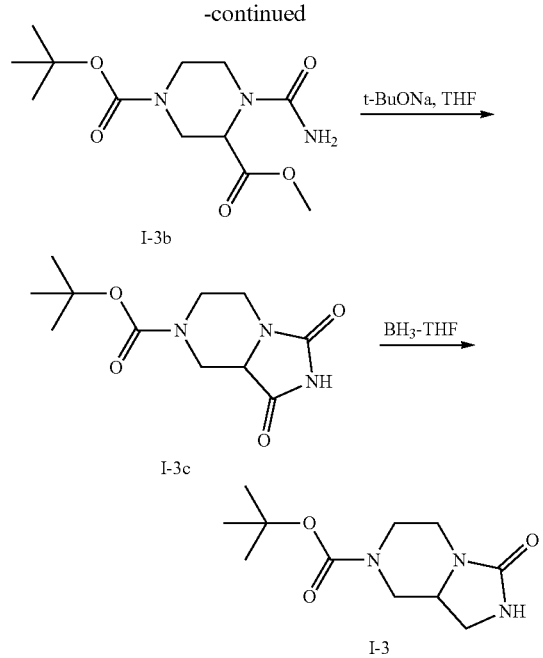

Step 1: Preparation of O1-tert-butyl O3-methyl 4-carbamoylpiperazine-1,3-dicarboxylate (Compound I-3b)

To a solution of 1-tert-butyl 3-methyl piperazine-1,3-dicarboxylate (compound I-3a, 1.22 g, 5 mmol) in anhydrous CH$_2$Cl$_2$ (15 mL) was added trimethylsilyl isocyanate (634 mg, 5.5 mmol).

The resulting mixture was stirred at room temperature for 64 h. The reaction mixture was directly concentrated under reduced pressure to afford crude O1-tert-butyl O3-methyl 4-carbamoylpiperazine-1,3-dicarboxylate (1.51 g) as a light-yellow foam which was directly used for next step without purification. MS obsd. (ESI$^+$) [(M+H)$^+$]: 288.

Step 2: Preparation of tert-butyl 1,3-dioxo-5,6,8,8a-tetrahydroimidazo[1,5-a]pyrazine-7-carboxylate (Compound I-3c)

To a solution of O1-tert-butyl O3-methyl 4-carbamoylpiperazine-1,3-dicarboxylate (compound I-3b, 1.51 g, 4.99 mmol) in THF (20 mL) was added sodium tert-butoxide (144 mg, 1.5 mmol). The resulting mixture was stirred at room temperature for 40 h. The reaction mixture was diluted with water and acidified by 1 M HCl to pH=4-5, and then extracted with EtOAc and CH$_2$Cl$_2$. The combined organic layer was washed with brine, dried over anhydrous Na$_2$SO$_4$, and concentrated under reduced pressure to afford tert-butyl 1,3-dioxo-5,6,8,8a-tetrahydroimidazo[1,5-a]pyrazine-7-carboxylate (1.23 g) as an off-white solid which was directly used for next step without purification. MS obsd. (ESI$^+$) [(M+H)$^+$]: 256.

Step 3: Preparation of tert-butyl 3-oxo-1,2,5,6,8,8a-hexahydroimidazo[1,5-a]pyrazine-7-carboxylate A mixture of tert-butyl 3-oxo-1,2,5,6,8,8a-hexahydroimidazo[1,5-a]pyrazine-7-carboxylate (1.23 g, 4.82 mmol) and borane tetrahydrofuran complex solution (24.1 mL, 24.1 mmol) was stirred at room temperature overnight. The reaction was quenched by methanol carefully, then aqueous NaOH was added and stirred at room temperature for 1 h, and then extracted with EtOAc for three times, combined organic layers were washed with brine, dried, concentrated to give some crude product. The crude product was purified by precipitation from EtOAc and hexane to give tert-butyl 3-oxo-1,2,5,6,8,8a-hexahydroimidazo[1,5-a]pyrazine-7-carboxylate (intermediate I-2, 512 mg) as a white solid, which was directly used for next without further purification. MS obsd. (ESI$^+$) [(M+H)$^+$]: 242.

Intermediate I-4 tert-butyl 4-(3-tert-butoxycarbonyl-6-chloro-hexyl)piperazine-1-carboxylate

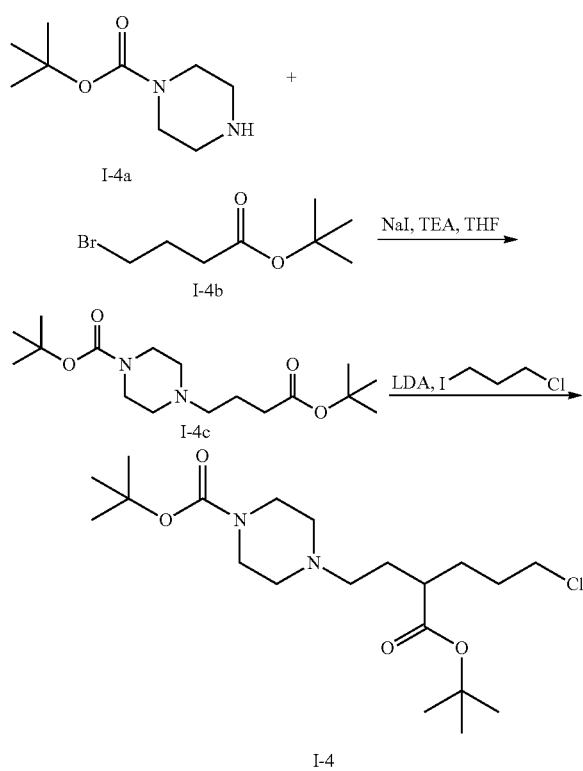

I-4

The title compound was prepared according to the following scheme:

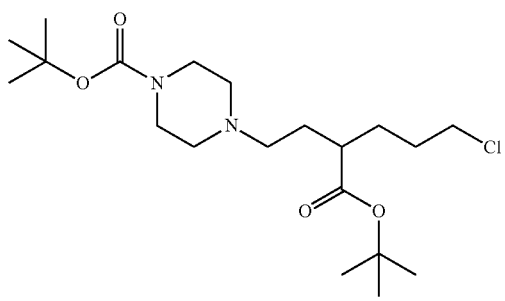

Step 1: Preparation of tert-butyl 4-(4-tert-butoxy-4-oxo-butyl)piperazine-1-carboxylate (Compound I-4c)

To a solution of tert-butyl piperazine-1-carboxylate (compound I-4a, 931 mg, 5 mmol) and TEA (607 mg, 6 mmol) in THF (5 mL) was added tert-butyl 4-bromobutanoate (compound I-4b, 1.34 g, 6 mmol) and sodium iodide (75 mg, 0.5 mmol). The reaction mixture was heated at 50° C. for 24 h. After cooling to room temperature, the reaction mixture was filtered, and the filtrate was concentrated under reduced pressure to afford crude tert-butyl 4-(4-tert-butoxy-4-oxo-butyl)piperazine-1-carboxylate (compound I-4c, 1.86 g) which was directly used for next step without purification. MS obsd. (ESI$^+$) [(M+H)$^+$]: 329.

Step 2: Preparation of tert-butyl 4-(3-tert-butoxy-carbonyl-6-chloro-hexyl)piperazine-1-carboxylate To a solution of tert-butyl 4-(4-tert-butoxy-4-oxo-butyl)piperazine-1-carboxylate (99 mg, 0.3 mmol) in THF (1 mL) was added LDA (0.3 mL, 0.6 mmol) dropwise at −78° C. and stirred at 0° C. for 1 h. The mixture was cooled to −78° C., and then 1-chloro-3-iodopropane (123 mg, 0.6 mmol) in THF (0.5 mL) was added dropwise at −78° C. The resulting mixture was stirred at −78° C. for 2 h, and then quenched by sat. NH$_4$Cl aqueous solution and extracted with CH$_2$Cl$_2$. The organic layer was washed with brine, dried and concentrated to give crude tert-butyl 4-(3-tert-butoxycarbonyl-6-chloro-hexyl)piperazine-1-carboxylate (intermediate I-4, 129 mg) as a yellow oil. MS obsd. (ESI$^+$) [(M+H)$^+$]: 405.

Intermediate I-5 ethyl 4-(6-chlorohexoxy)-3-oxo-butanoate

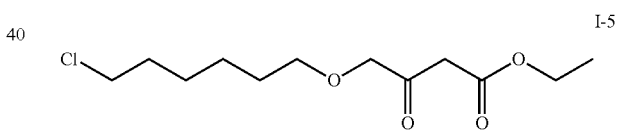

The title compound was prepared according to the following scheme:

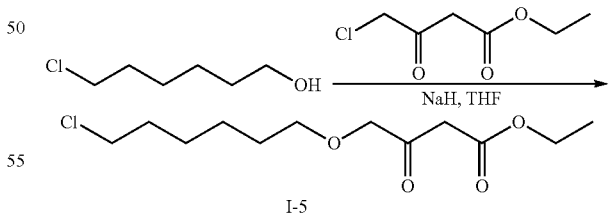

Preparation of ethyl 4-(6-chlorohexoxy)-3-oxo-butanoate (Intermediate I-5)

6-chlorohexan-1-ol (273 mg, 2 mmol) was added dropwise to a suspension of NaH (160 mg, 4 mmol) in THF (2 mL) cooling with an ice-bath. Then the ice-bath was removed and the mixture was stirred for 1 h. Then ethyl 4-chloro-3-oxobutanoate (165 mg, 1 mmol) was added and the resulting mixture was stirred at room temperature for 16 h. The reaction was quenched by water, and then the mixture was concentrated under reduced pressure. The residue was diluted with water. The resulting mixture was acidified by 1 M HCl and extracted with EtOAc. The organic layer was washed with brine, dried and concentrated to give ethyl 4-(6-chlorohexoxy)-3-oxo-butanoate (intermediate I-5, 452 mg) as a yellow oil. MS obsd. (ESI$^+$) [(M+H)$^+$]: 265.

Intermediate I-6 tert-butyl (3S)-3-formylmorpholine-4-carboxylate

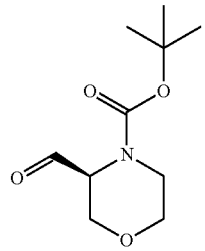

I-6

The title compound was prepared according to the following scheme:

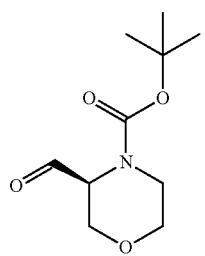

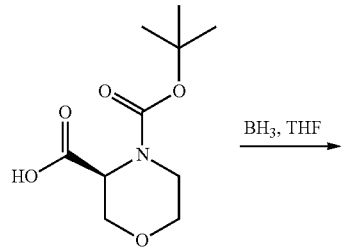

Step 1: Preparation of tert-butyl (3R)-3-(hydroxymethyl)morpholine-4-carboxylate To a solution of (S)-4-(tert-butoxycarbonyl)morpholine-3-carboxylic acid (3 g, 13 mmol) in THF (50 mL) was added borane-tetrahydrofuran complex (64.9 mL, 64.9 mmol) dropwise at 0° C. The mixture was warmed to room temperature and stirred for 16 hours. The reaction mixture was quenched with 2 M HCl solution, and then stirred for one hour at room temperature. The mixture was diluted with water and extracted in DCM. The organic layer was dried over anhydrous Na$_2$SO$_4$ and concentrated to give compound I-6a (2.82 g).

Step 2: Preparation of tert-butyl (3S)-3-formylmorpholine-4-carboxylate (Intermediate I-6)

To a solution of crude (R)-tert-butyl 3-(hydroxymethyl)morpholine-4-carboxylate (compound I-6a, 500 mg) in DCM (20 mL) was added Dess-Martin periodinane (1.46 g, 3.45 mmol) in portions at 0° C. The mixture was warmed to room temperature and stirred for 16 hours. The reaction was quenched with saturated aqueous NaHCO$_3$ and Na$_2$S$_2$O$_4$. The mixture was extracted with DCM. The organic layer was dried over anhydrous Na$_2$SO$_4$. The organic layer was concentrated to give tert-butyl (3S)-3-formylmorpholine-4-carboxylate (intermediate I-6, 495 mg).

Intermediate I-7

6-[2,3-difluoro-5-(5-methyl-2-pyrimidin-2-yl-7,8-dihydro-5H-pyrido[4,3-d]pyrimidin-6-yl)phenoxy] hexanal

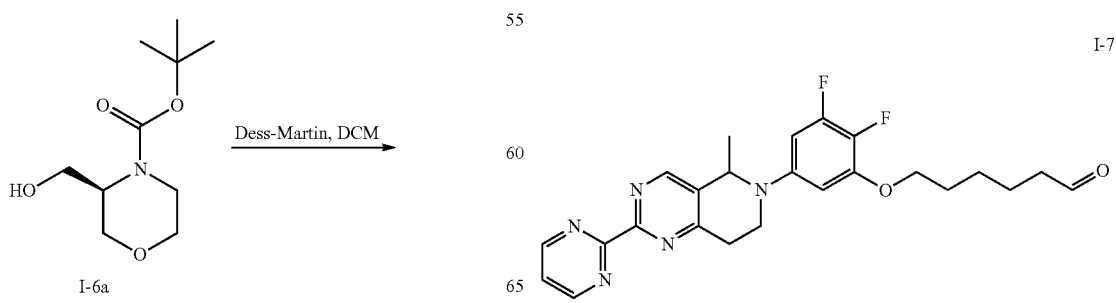

The title compound was prepared according to the following scheme:

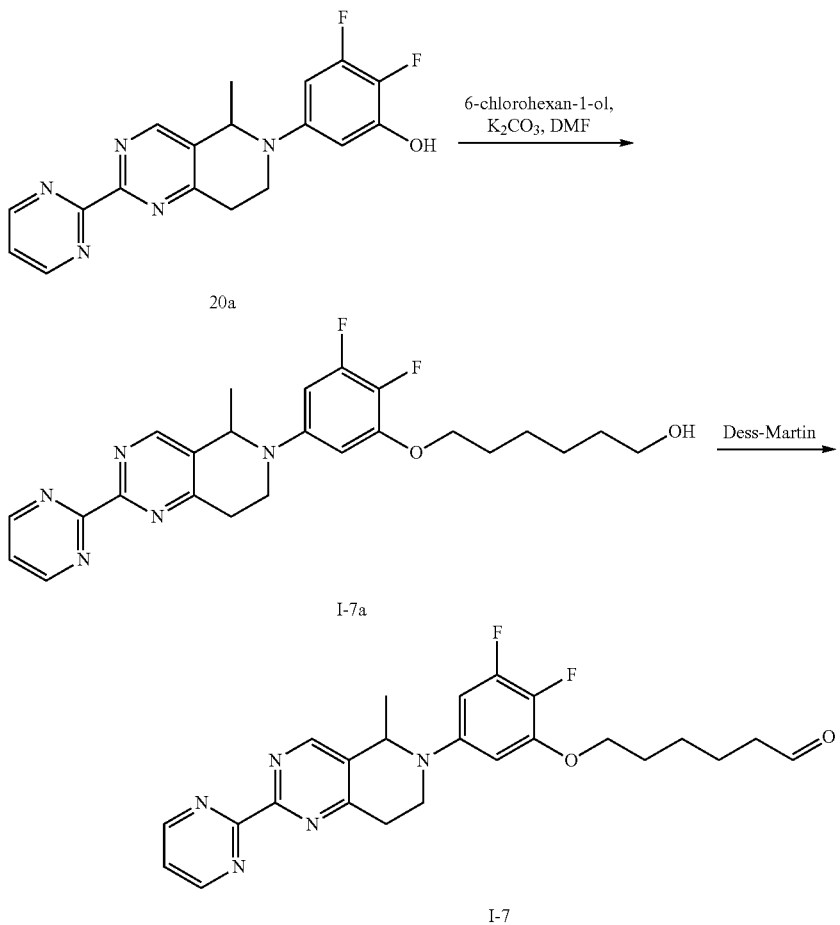

Step 1: Preparation of 6-[2,3-difluoro-5-(5-methyl-2-pyrimidin-2-yl-7,8-dihydro-5H-pyrido[4,3-d]pyrimidin-6-yl)phenoxy]hexan-1-ol To a solution of 2,3-difluoro-5-(5-methyl-2-(pyrimidin-2-yl)-7,8-dihydropyrido[4,3-d]pyrimidin-6(5H)-yl)phenol (compound 20a, 700 mg, 1.97 mmol) in DMF (10 mL) was added 6-chlorohexan-1-ol (350 mg, 2.56 mmol) and potassium carbonate (545 mg, 3.94 mmol). The mixture was stirred at 100° C. for 3 hours, and then cooled to room temperature and partitioned between DCM and brine. The organic layer was dried over anhydrous $Na_2SO_4$ and concentrated.

The residue was purified by column chromatography to give 6-[2,3-difluoro-5-(5-methyl-2-pyrimidin-2-yl-7,8-dihydro-5H-pyrido[4,3-d]pyrimidin-6-yl)phenoxy]hexan-1-ol (compound I-7a, 678 mg).

Step 2: Preparation of 6-[2,3-difluoro-5-(5-methyl-2-pyrimidin-2-yl-7,8-dihydro-5H-pyrido[4,3-d]pyrimidin-6-yl)phenoxy]hexanal To a solution of 6-(2,3-difluoro-5-(2-(pyrimidin-2-yl)-7,8-dihydropyrido[4,3-d]pyrimidin-6(5H)-yl)phenoxy)hexan-1-ol (compound I-7a, 200 mg, 453 μmol) in DCM (5 mL) was added Dess-Martin periodinane (288 mg, 680 μmol).

The mixture was stirred at room temperature for 15 hours, and then filtered. The filtrate was washed with saturated $NaHCO_3$ solution and $Na_2S_2O_3$ and solution, dried over anhydrous $Na_2SO_4$ and concentrated to give crude 6-[2,3-difluoro-5-(5-methyl-2-pyrimidin-2-yl-7,8-dihydro-5H-pyrido[4,3-d]pyrimidin-6-yl)phenoxy]hexanal (intermediate I-7, 172 mg).

Intermediate I-8

(2R)-2-(tert-butoxycarbonylamino)-4-oxo-butanoic Acid

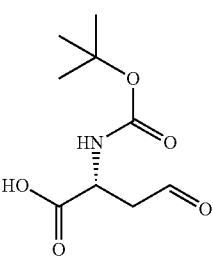

I-8

The title compound was prepared according to the following scheme:

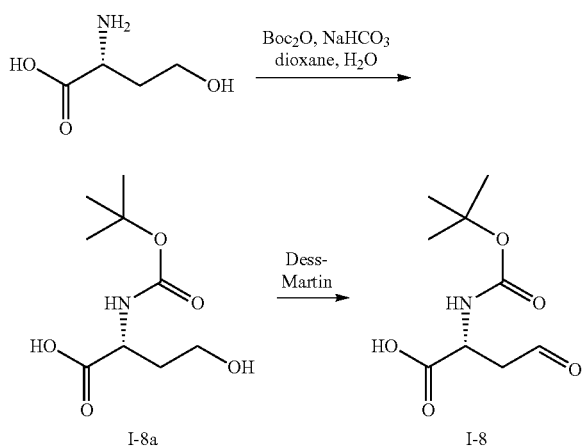

Step 1: Preparation of (2R)-2-(tert-butoxycarbonylamino)-4-hydroxy-butanoic Acid (Compound I-8a)

To a solution of (R)-2-amino-4-hydroxybutanoic acid (500 mg, 4.2 mmol) in dioxane (5 mL) and water (10 mL) was added sodium bicarbonate (705 mg, 8.39 mmol). The mixture was cooled to −10° C., and then a solution of Boc$_2$O (1.01 g, 4.62 mmol) in dioxane (5 mL) was added dropwise. The mixture was warmed to room temperature and stirred at room temperature for 16 hours, then acidified with 1 M HCl and extracted in EtOAc. The organic layer was dried over anhydrous Na$_2$SO$_4$ and concentrated under reduced pressure to give (2R)-2-(tert-butoxycarbonylamino)-4-hydroxy-butanoic acid (compound I-8a, 0.9 g).

Step 2: Preparation of (2R)-2-(tert-butoxycarbonylamino)-4-oxo-butanoic Acid (Intermediate I-8)

To a solution of (2R)-2-(tert-butoxycarbonylamino)-4-hydroxy-butanoic acid (compound I-8a, 500 mg, 2.28 mmol) in DCM (10 mL) was added Dess-Martin periodinane (1.45 g) in portions at 0° C. The mixture was warmed to room temperature and stirred for 15 hours. The mixture was filtered and the filtrate was concentrated under reduce pressure to give the crude intermediate I-8 (0.9 g) which was directly used without further purification.

Example 1

6-tert-butyl-9-[6-[4-[[(4R)-4-(2-chloro-4-fluorophenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylic Acid

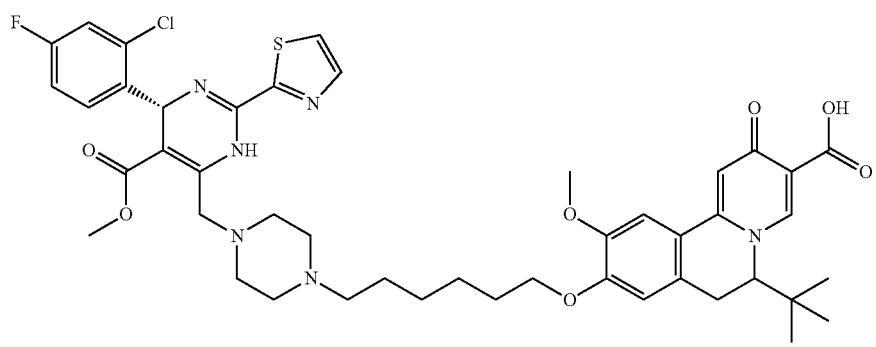

The title compound was prepared according to the following scheme:

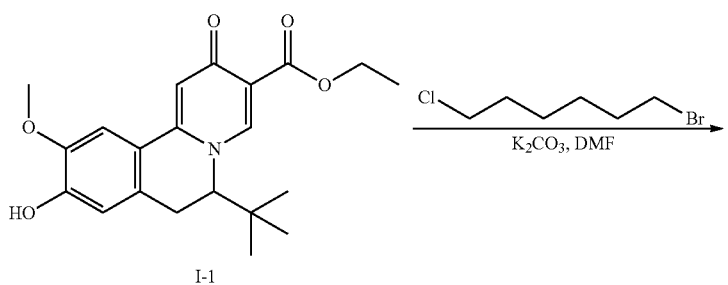

-continued
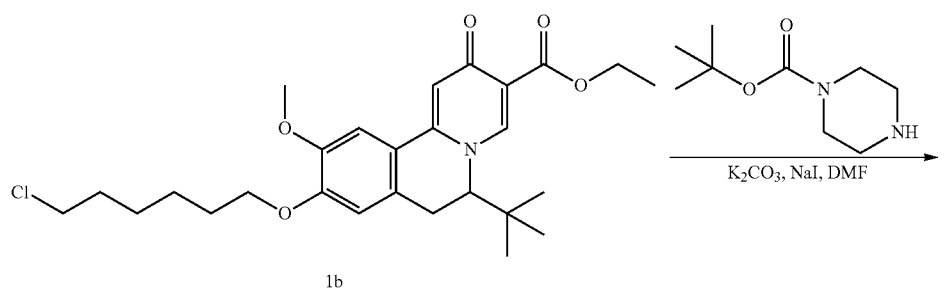
1b
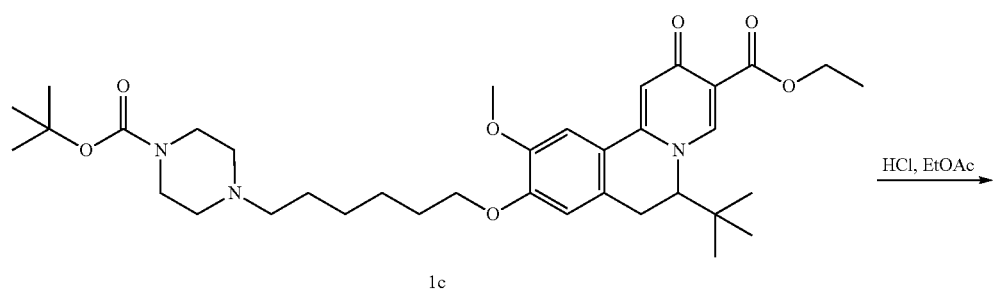
1c
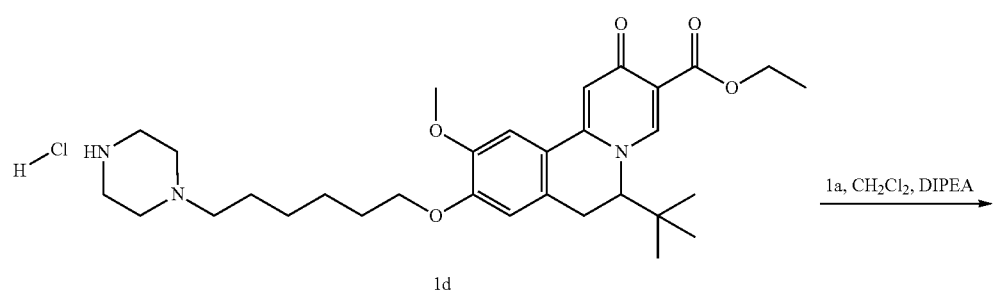
1d
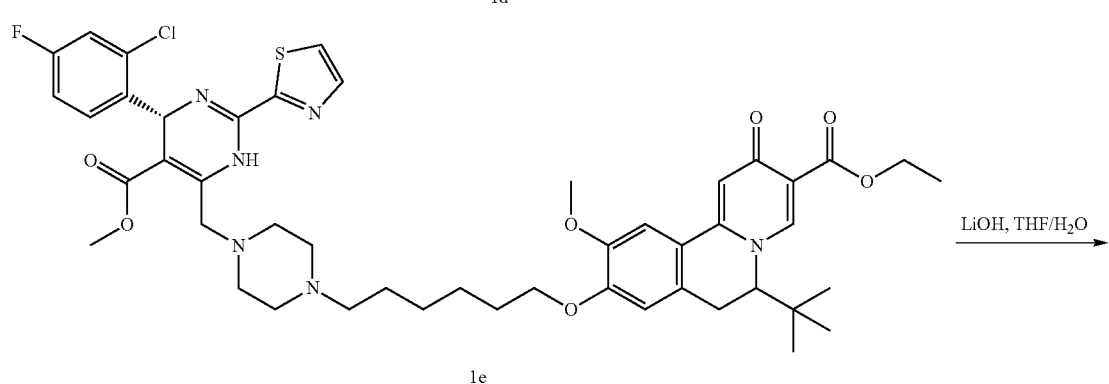
1e
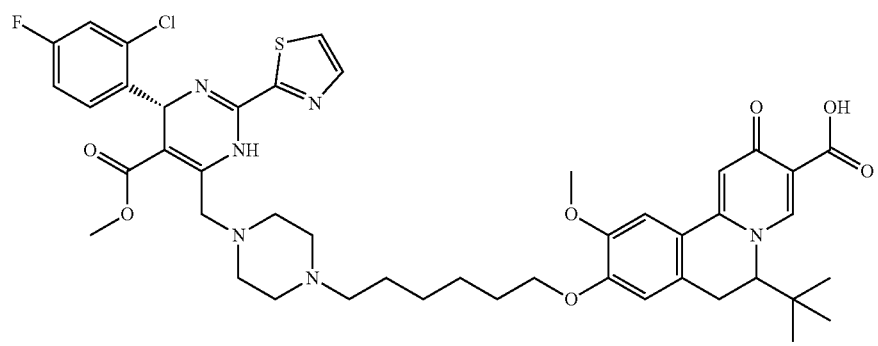 [SMILES: COC(=O)C1=C(CN2CCN(CCCCCCOc3cc4c(cc3OC)-c3cc(=O)c(C(=O)O)cn3C(C(C)(C)C)C4)CC2)NC(c2nccs2)=N[C@H]1c1ccc(F)cc1Cl]
1

Step 1: Preparation of ethyl 6-tert-butyl-9-(6-chlorohexoxy)-10-methoxy-2-oxo-6,7-dihydrobenzo[a]quinolizine-3-carboxylate (Compound 1b)

To a solution of ethyl 6-tert-butyl-9-hydroxy-10-methoxy-2-oxo-6,7-dihydrobenzo[a]quinolizine-3-carboxylate (intermediate I-1, 223 mg, 0.6 mmol, prepared according to US20150210682) in DMF (4 mL) was added potassium carbonate (166 mg, 1.2 mmol), the mixture was stirred at room temperature for 1 h. Then 1-bromo-6-chlorohexane (359 mg, 1.8 mmol) was added and stirred at 60° C. for 5 h. After cooling to room temperature, the mixture was diluted with EtOAc and water, and then extracted with EtOAc for three times. The combined organic layer was washed with brine, dried over anhydrous $Na_2SO_4$, and concentrated. The residue was washed with petroleum ether to give ethyl 6-tert-butyl-9-(6-chlorohexoxy)-10-methoxy-2-oxo-6,7-dihydrobenzo[a]quinolizine-3-carboxylate (compound 1b, 299 mg) as a dark solid, which was directly used for next step without further purification. MS obsd. (ESI$^+$) [(M+H)$^+$]: 490.

Step 2: Preparation of ethyl 9-[6-(4-tert-butoxycarbonylpiperazin-1-yl)hexoxy]-6-tert-butyl-10-methoxy-2-oxo-6,7-dihydrobenzo[a]quinolizine-3-carboxylate (Compound 1c)

To a solution of crude ethyl 6-tert-butyl-9-(6-chlorohexoxy)-10-methoxy-2-oxo-6,7-dihydrobenzo[a]quinolizine-3-carboxylate (299 mg, 0.61 mmol) and tert-butyl piperazine-1-carboxylate (114 mg, 0.61 mmol) in DMF (4 mL) was added sodium iodide (91.5 mg, 0.61 mmol), followed by potassium carbonate (169 mg, 1.22 mmol). The reaction mixture was heated at 80° C. for 16 h. After cooling to room temperature, the mixture was diluted with EtOAc and water. The aqueous layer was extracted with EtOAc for three times. The combined organic layer was washed with brine, dried over anhydrous $Na_2SO_4$, and concentrated to afford crude ethyl 9-[6-(4-tert-butoxycarbonylpiperazin-1-yl)hexoxy]-6-tert-butyl-10-methoxy-2-oxo-6,7-dihydrobenzo[a]quinolizine-3-carboxylate (compound 1c, 428 mg) as a dark oil, which was directly used for next step without further purification. MS obsd. (ESI$^+$) [(M+H)$^+$]: 640.

Step 3: Preparation of ethyl 6-tert-butyl-10-methoxy-2-oxo-9-(6-piperazin-1-ylhexoxy)-6,7-dihydrobenzo[a]quinolizine-3-carboxylate Hydrochloride (Compound 1d)

A solution of crude ethyl 9-[6-(4-tert-butoxycarbonylpiperazin-1-yl)hexoxy]-6-tert-butyl-10-methoxy-2-oxo-6,7-dihydrobenzo[a]quinolizine-3-carboxylate (428 mg, 0.6 mmol) and 1M hydrogen chloride in EtOAc (8 mL, 8 mmol) was stirred at room temperature for 1 h. After removing the excess solvent under reduced pressure, crude ethyl 6-tert-butyl-10-methoxy-2-oxo-9-(6-piperazin-1-ylhexoxy)-6,7-dihydrobenzo[a]quinolizine-3-carboxylate hydrochloride (compound 1d, 435 mg) was obtained as a brown solid, which was directly used for next step without purification. MS obsd. (ESI$^+$) [(M+H)$^+$]: 540.

Step 4: Preparation of ethyl 6-tert-butyl-9-[6-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylate (Compound 1e)

To a mixture of methyl (4R)-6-(bromomethyl)-4-(2-chloro-4-fluoro-phenyl)-2-thiazol-2-yl-1,4-dihydropyrimidine-5-carboxylate (269 mg, 0.6 mmol) and crude ethyl 6-tert-butyl-10-methoxy-2-oxo-9-(6-piperazin-1-ylhexoxy)-6,7-dihydrobenzo[a]quinolizine-3-carboxylate hydrochloride (435 mg, 0.6 mmol) in $CH_2Cl_2$ (8 mL) was added DIPEA (234 mg, 1.80 mmol). The reaction mixture was stirred at room temperature for 4 h. The mixture was diluted with water and $CH_2Cl_2$. The aqueous layer was extracted with $CH_2Cl_2$. The combined organic layer was washed with brine, dried over anhydrous $Na_2SO_4$, and concentrated to give crude ethyl 6-tert-butyl-9-[6-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylate (compound 1e, 508 mg) as a brown oil which was directly used for next step without purification. MS obsd. (ESI$^+$) [(M+H)$^+$]: 903.

Step 5: Preparation of 6-tert-butyl-9-[6-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylic Acid

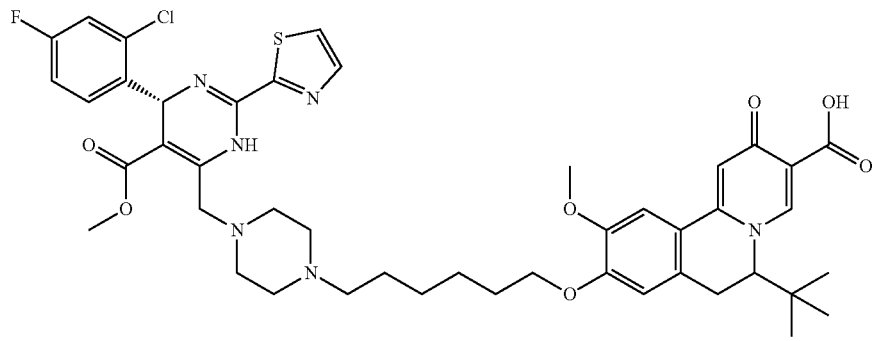 [SMILES: COC(=O)C1=C(CN2CCN(CCCCCCOc3cc4c(cc3OC)-c3cc(=O)c(C(=O)O)cn3C(C(C)(C)C)C4)CC2)NC(c2nccs2)=N[C@H]1c1ccc(F)cc1Cl]

A mixture of crude ethyl 6-tert-butyl-9-[6-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylate (508 mg, 0.56 mmol) and lithium hydroxide hydrate (189 mg, 4.5 mmol) in THF (8 mL) and $H_2O$ (2 mL) was stirred at room temperature for 3 h. The reaction mixture was diluted with water and acidified by acetic acid to pH-3, and then extracted with $CH_2Cl_2$ for three times. The combined organic layer was washed with water, dried over anhydrous $Na_2SO_4$, and concentrated. The residue was purified by flash chromatography to afford 6-tert-butyl-9-[6-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylic acid (Example 1, 70 mg) as a yellow solid. MS obsd. (ESI+) [(M+H)+]: 875. ¹H NMR (400 MHz, DMSO-d₆) δ=9.69 (s, 1H), 8.72 (s, 1H), 8.01 (d, 1H), 7.94 (d, 1H), 7.49-7.34 (m, 4H), 7.17 (dt, 1H), 7.06 (s, 1H), 6.04 (s, 1H), 4.56 (d, 1H), 4.11-3.99 (m, 2H), 3.96-3.81 (m, 5H), 3.52 (s, 3H), 3.42-3.21 (m, 2H), 2.53-2.49 (m, 6H), 1.82-1.70 (m, 2H), 1.51-1.22 (m, 8H), 0.73 (s, 9H)

Example 2

6-tert-butyl-9-[5-[4-[[(4R)-4-(2-chloro-4-fluorophenyl)-5-methoxycarbonyl-2-thiazol-2-yl-1,4-dihydropyrimidin-6-yl]methyl]piperazin-1-yl]pentoxy]-10-methoxy-2-oxo-6,7-dihydrobenzo[a]quinolizine-3-carboxylic Acid

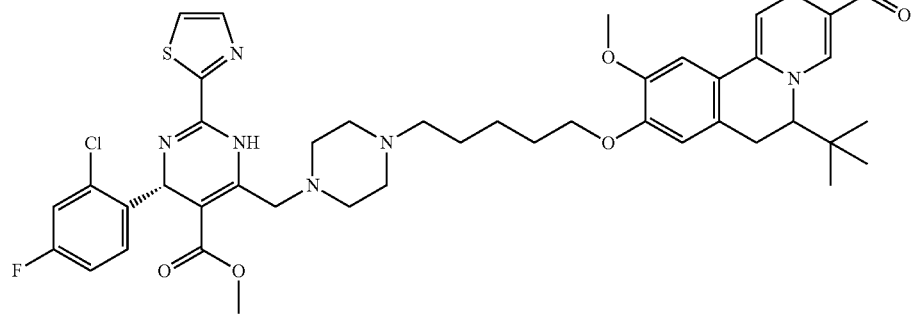

The title compound was prepared in analogy to the preparation of Example 1 by using 1,5-dibromopentane instead of 1-bromo-6-chlorohexane (Step 1, Example 1). Example 2 (59 mg) was obtained as a yellow solid. MS obsd. (ESI+) [(M+H)+]: 861. ¹H NMR (400 MHz, DMSO-d₆) δ=9.69 (s, 1H), 8.71 (s, 1H), 8.19 (s, 1H), 8.01 (d, 1H), 7.94 (d, 1H), 7.48-7.34 (m, 4H), 7.17 (dt, 1H), 7.06 (s, 1H), 6.03 (s, 1H), 4.56 (d, 1H), 4.14-3.98 (m, 2H), 3.95-3.80 (m, 5H), 3.52 (s, 3H), 3.42-3.20 (m, 2H), 2.60-2.39 (m, 6H), 2.33 (t, 2H), 1.84-1.71 (m, 2H), 1.57-1.39 (m, 4H), 1.31-1.20 (m, 2H), 0.72 (s, 9H)

Example 3

6-tert-butyl-9-[4-[4-[[(4R)-4-(2-chloro-4-fluorophenyl)-5-methoxycarbonyl-2-thiazol-2-yl-1,4-dihydropyrimidin-6-yl]methyl]piperazin-1-yl]butoxy]-10-methoxy-2-oxo-6,7-dihydrobenzo[a]quinolizine-3-carboxylic Acid

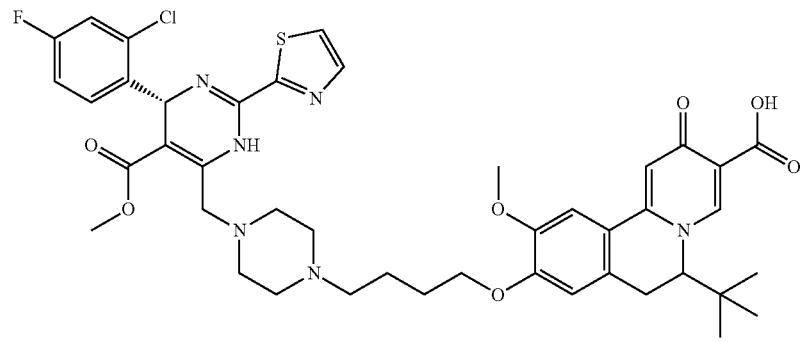 [SMILES: COC(=O)C1=C(CN2CCN(CCCCOc3cc4c(cc3OC)-c3cc(=O)c(C(=O)O)cn3C(C(C)(C)C)C4)CC2)NC(c2nccs2)=N[C@H]1c1ccc(F)cc1Cl]

The title compound was prepared in analogy to the preparation of Example 1 by using 1,4-dibromobutane instead of 1-bromo-6-chlorohexane (Step 1, Example 1). Example 3 (57 mg) was obtained as a yellow solid. MS obsd. (ESI$^+$) [(M+H)$^+$]: 847. $^1$H NMR (400 MHz, DMSO-d$_6$) δ=9.69 (br s, 1H), 8.71 (s, 1H), 8.18 (s, 1H), 8.01 (d, 1H), 7.94 (d, 1H), 7.50-7.33 (m, 4H), 7.17 (dt, 1H), 7.05 (s, 1H), 6.03 (s, 1H), 4.56 (d, 1H), 4.15-4.00 (m, 2H), 3.95-3.78 (m, 5H), 3.51 (s, 3H), 3.43-3.19 (m, 2H), 2.60-2.39 (m, 6H), 2.40 (t, 2H), 1.83-1.73 (m, 2H), 1.65-1.54 (m, 2H), 1.31-1.21 (m, 2H), 0.73 (s, 9H).

Example 4

6-tert-butyl-9-[3-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]propoxy]-10-methoxy-2-oxo-6,7-dihydrobenzo[a]quinolizine-3-carboxylic Acid

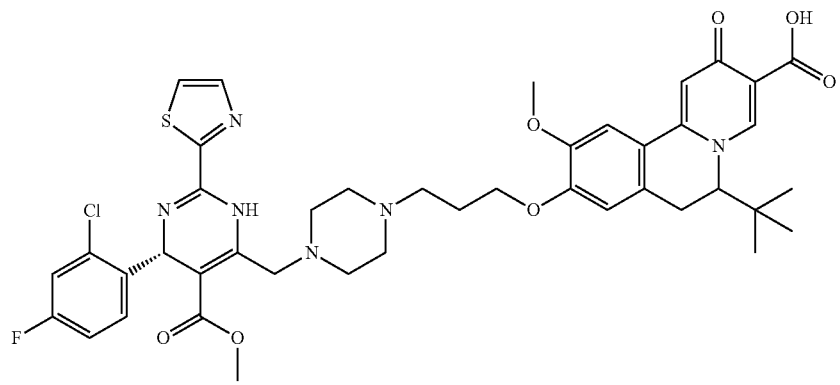 [SMILES: COC(=O)C1=C(CN2CCN(CCCOc3cc4c(cc3OC)-c3cc(=O)c(C(=O)O)cn3C(C(C)(C)C)C4)CC2)NC(c2nccs2)=N[C@H]1c1ccc(F)cc1Cl]

The title compound was prepared in analogy to the preparation of Example 1 by using 1-bromo-3-chloropropane instead of 1-bromo-6-chlorohexane (Step 1, Example 1). Example 4 (30 mg) was obtained as a yellow solid. MS obsd. (ESI$^+$) [(M+H)$^+$]: 833. $^1$H NMR (400 MHz, DMSO-d$_6$) δ=9.70 (br s, 1H), 8.71 (s, 1H), 8.29-7.90 (m, 3H), 7.51-7.35 (m, 4H), 7.23-7.05 (m, 2H), 6.03 (s, 1H), 4.56 (d, 1H), 4.15-4.05 (m, 2H), 3.97-3.81 (m, 5H), 3.51 (s, 3H), 3.31-3.22 (m, 2H), 2.65-2.30 (m, 8H), 1.99-1.89 (m, 2H), 1.33-1.19 (m, 2H), 0.73 (s, 9H)

Example 5

6-tert-butyl-9-[3-[2-carboxy-4-[[(4R)-4-(2-chloro-4-fluoro-phenyl)-5-methoxycarbonyl-2-thiazol-2-yl-1,4-dihydropyrimidin-6-yl]methyl]piperazin-1-yl]propoxy]-10-methoxy-2-oxo-6,7-dihydrobenzo[a]quinolizine-3-carboxylic Acid

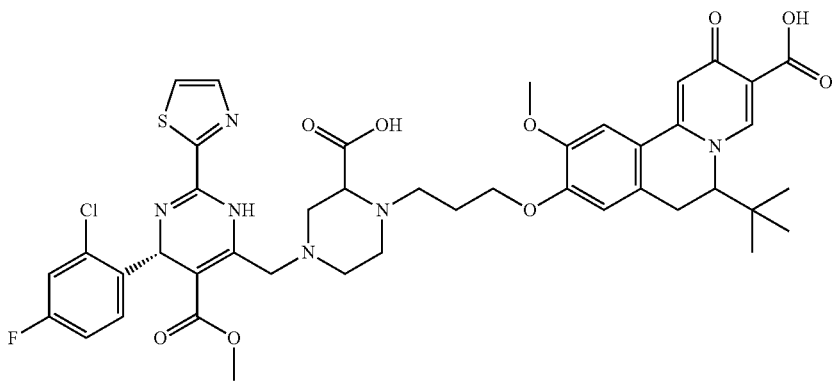 [SMILES: COC(=O)C1=C(CN2CCN(CCCOc3cc4c(cc3OC)-c3cc(=O)c(C(=O)O)cn3C(C(C)(C)C)C4)C(C(=O)O)C2)NC(c2nccs2)=N[C@H]1c1ccc(F)cc1Cl]

The title compound was prepared in analogy to the preparation of Example 1 by using 1-bromo-3-chloropropane instead of 1-bromo-6-chlorohexane (Step 1, Example 1), and 1-tert-butyl 3-methyl piperazine-1,3-dicarboxylate instead of tert-butyl piperazine-1-carboxylate (Step 2, Example 1). Example 5 (30 mg) was obtained as a yellow solid. MS obsd. (ESI+) [(M+H)+]: 877. $^1$H NMR (400 MHz, DMSO-d$_6$) δ=8.73 (s, 1H), 8.10-8.00 (m, 2H), 7.53-7.40 (m, 4H), 7.23-7.15 (m, 1H), 7.05 (s, 1H), 6.02 (s, 1H), 4.57 (d, 1H), 4.18-4.08 (m, 4H), 3.86 (s, 3H), 3.55 (s, 3H), 3.45-3.18 (m, 4H), 2.19-1.94 (m, 3H), 1.24 (br s, 3H), 0.73 (s, 9H).

Example 6

6-tert-butyl-9-[6-[3-carboxy-4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylic Acid

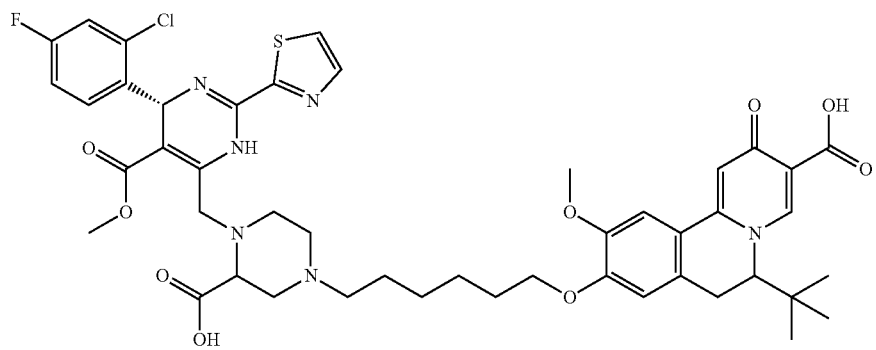 [SMILES: COC(=O)C1=C(CN2CCN(CCCCCCOc3cc4c(cc3OC)-c3cc(=O)c(C(=O)O)cn3C(C(C)(C)C)C4)CC2C(=O)O)NC(c2nccs2)=N[C@H]1c1ccc(F)cc1Cl]

The title compound was prepared in analogy to the preparation of Example 1 by using 1-tert-butyl 2-methyl piperazine-1,2-dicarboxylate instead of tert-butyl piperazine-1-carboxylate (Step 2, Example 1). Example 6 (22 mg) was obtained as a yellow solid. MS obsd. (ESI+) [(M+H)+]: 919. $^1$H NMR (400 MHz, DMSO-d$_6$) δ=9.69 (s, 1H), 8.72 (s, 1H), 8.05-7.90 (m, 2H), 7.54-7.31 (m, 4H), 7.24-7.02 (m, 3H), 6.04 (s, 1H), 4.57 (d, 1H), 4.21-4.01 (m, 2H), 3.87 (s, 3H), 3.52 (s, 3H), 3.30-3.05 (m, 7H), 1.78-1.65 (m, 3H), 1.53-1.33 (m, 4H), 1.30-1.21 (m, 2H), 0.73 (s, 9H).

Example 7

6-tert-butyl-9-[6-[2-carboxy-4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylic Acid

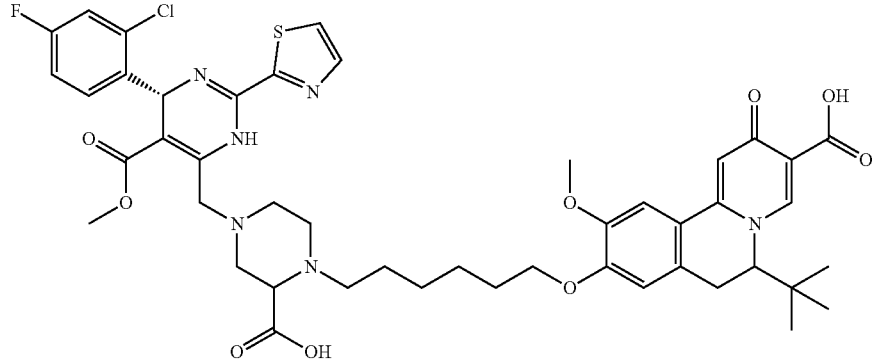 [SMILES: COC(=O)C1=C(CN2CCN(CCCCCCOc3cc4c(cc3OC)-c3cc(=O)c(C(=O)O)cn3C(C(C)(C)C)C4)C(C(=O)O)C2)NC(c2nccs2)=N[C@H]1c1ccc(F)cc1Cl]

The title compound was prepared in analogy to the preparation of Example 1 by using 1-tert-butyl 3-methyl piperazine-1,3-dicarboxylate instead of tert-butyl piperazine-1-carboxylate (Step 2, Example 1). Example 7 (130 mg) was obtained as a yellow solid. MS obsd. (ESI$^+$) [(M+H)$^+$]: 919. $^1$H NMR (400 MHz, DMSO-d$_6$) δ=8.73 (s, 1H), 8.07-7.98 (m, 2H), 7.50-7.39 (m, 4H), 7.23-7.14 (m, 1H), 7.06 (s, 1H), 6.03 (s, 1H), 4.57 (d, 1H), 4.25-3.99 (m, 4H), 3.86 (s, 3H), 3.54 (s, 3H), 3.42-3.21 (m, 5H), 1.83-1.59 (m, 4H), 1.50-1.33 (m, 4H), 0.73 (s, 9H).

Example 8

6-tert-butyl-9-[6-[7-[[(4R)-4-(2-chloro-4-fluorophenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]hexoxy]-10-methoxy-2-oxo-6,7-dihydrobenzo[a]quinolizine-3-carboxylic Acid

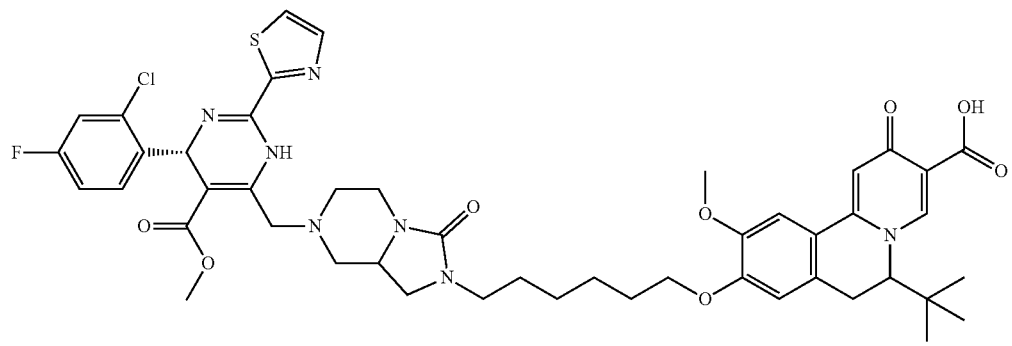 [SMILES: COC(=O)C1=C(CN2CCN3C(=O)N(CCCCCCOc4cc5c(cc4OC)-c4cc(=O)c(C(=O)O)cn4C(C(C)(C)C)C5)CC3C2)NC(c2nccs2)=N[C@H]1c1ccc(F)cc1Cl]

The title compound was prepared in analogy to the preparation of Example 1 by using intermediate I-2 instead of tert-butyl piperazine-1-carboxylate (Step 2, Example 1). Example 8 (130 mg) was obtained as a yellow solid. MS obsd. (ESI$^+$) [(M+H)$^+$]: 930. $^1$H NMR (400 MHz, DMSO-d$_6$) δ=8.72 (s, 1H), 8.15-8.02 (m, 2H), 7.54-7.41 (m, 4H), 7.29-7.17 (m, 1H), 7.06 (s, 1H), 6.02 (d, 1H), 4.62-4.39 (m, 3H), 4.15-3.95 (m, 2H), 3.86 (s, 3H), 3.57 (s, 3H), 3.50-3.05 (m, 4H), 1.76 (br s, 2H), 1.55-1.20 (m, 8H), 0.73 (s, 9H).

Example 9

6-tert-butyl-9-[6-[[(4R)-4-(2-chloro-4-fluorophenyl)-5-methoxycarbonyl-2-thiazol-2-yl-1,4-dihydropyrimidin-6-yl]methyl-methyl-amino]hexoxy]-10-methoxy-2-oxo-6,7-dihydrobenzo[a]quinolizine-3-carboxylic Acid

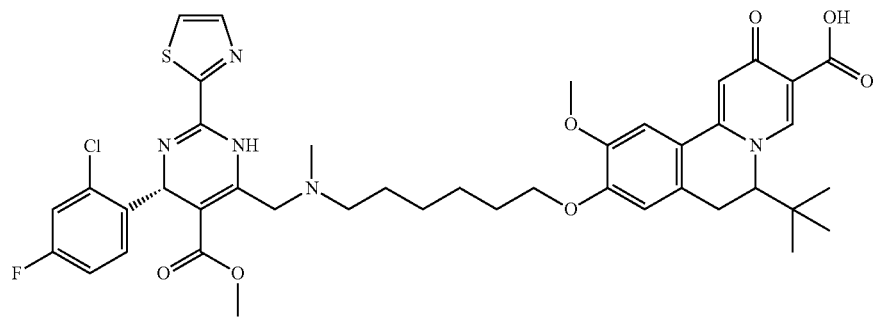 [SMILES: COC(=O)C1=C(CN(C)CCCCCCOc2cc3c(cc2OC)-c2cc(=O)c(C(=O)O)cn2C(C(C)(C)C)C3)NC(c2nccs2)=N[C@H]1c1ccc(F)cc1Cl]

The title compound was prepared according to the following scheme:
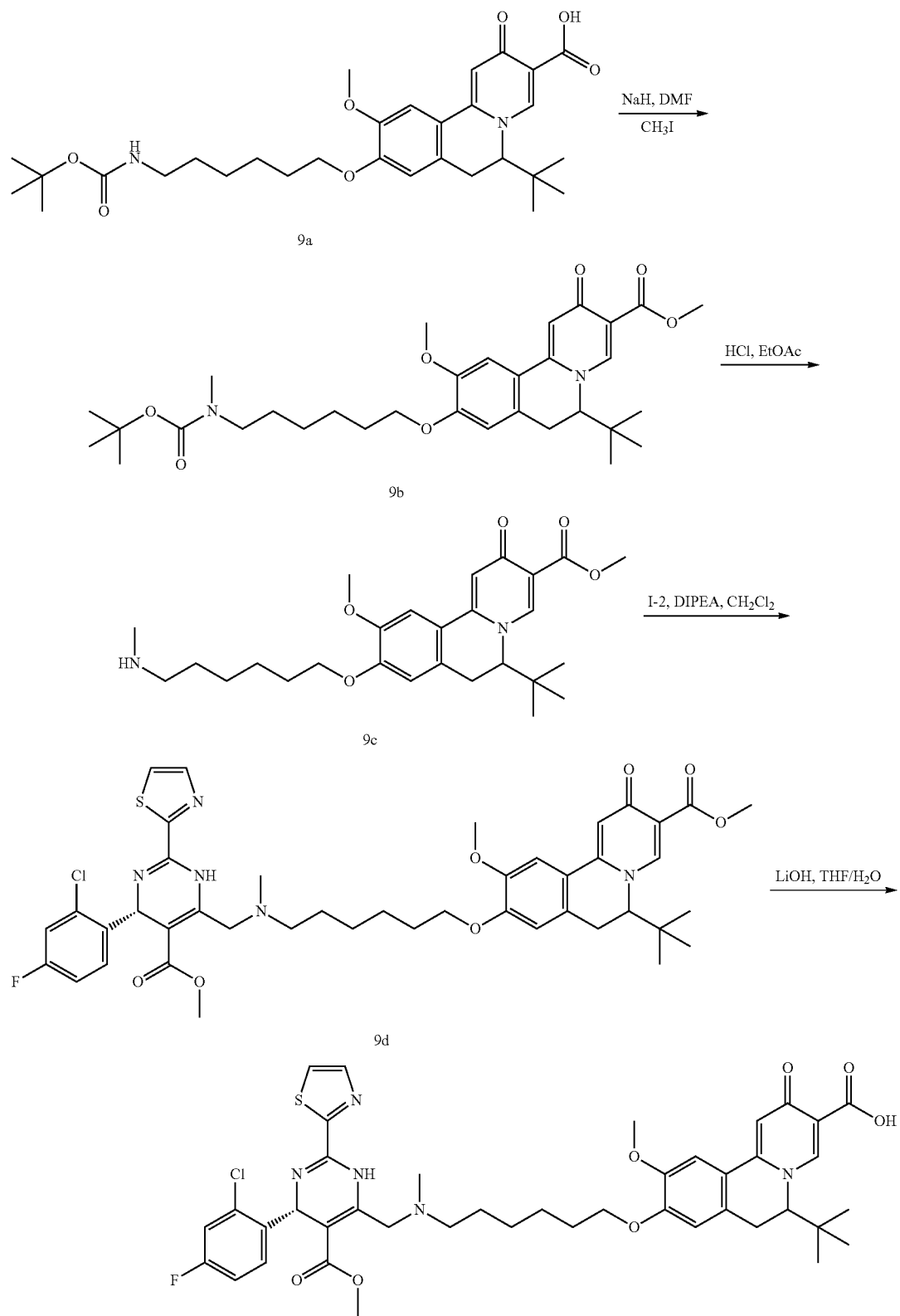

Step 1: Preparation of methyl 9-[6-[tert-butoxycarbonyl(methyl)amino]hexoxy]-6-tert-butyl-10-methoxy-2-oxo-6,7-dihydrobenzo[a]quinolizine-3-carboxylate (Compound 9b)

To a solution of 9-[6-(tert-butoxycarbonylamino)hexoxy]-6-tert-butyl-10-methoxy-2-oxo-6,7-dihydrobenzo[a]quinolizine-3-carboxylic acid (compound 9a, 71 mg, 0.1 mmol, prepared according to US20150210682) in DMF (1 mL) was added NaH (12 mg, 0.3 mmol) at 0° C. The mixture was stirred at 0° C. for 30 min, and then iodomethane (141 mg, 0.9 mmol) was added. The mixture was allowed to warm to rt and stirred overnight. The mixture was diluted with EtOAc and water, and then the aqueous layer was extracted with EtOAc for three times. The combined organic layer was washed with brine, dried over anhydrous $Na_2SO_4$ and concentrated to give crude methyl 9-[6-[tert-butoxycarbonyl(methyl)amino]hexoxy]-6-tert-butyl-10-methoxy-2-oxo-6,7-dihydrobenzo[a]quinolizine-3-carboxylate (79 mg) as a yellow oil, which was directly used for next step without purification. MS obsd. (ESI) [(M+H)]: 571.

Step 2: Preparation of methyl 6-tert-butyl-10-methoxy-9-[6-(methylamino)hexoxy]-2-oxo-6,7-dihydrobenzo[a]quinolizine-3-carboxylate Hydrochloride (Compound 9c)

A mixture of crude methyl 9-[6-[tert-butoxycarbonyl(methyl)amino]hexoxy]-6-tert-butyl-10-methoxy-2-oxo-6,7-dihydrobenzo[a]quinolizine-3-carboxylate (compound 9b, 79 mg, 0.097 mmol) and 1M hydrogen chloride in EtOAc (5 mL, 5 mmol) was stirred at room temperature for 2 h. After removing excess solvent under reduced pressure, crude methyl 6-tert-butyl-10-methoxy-9-[6-(methylamino)hexoxy]-2-oxo-6,7-dihydrobenzo[a]quinolizine-3-carboxylate hydrochloride (66 mg) was obtained as a yellow oil, which was directly used for next step without purification. MS obsd. (ESI$^+$) [(M+H)$^+$]: 471.

Step 3: Preparation of methyl 6-tert-butyl-9-[6-[[(4R)-4-(2-chloro-4-fluoro-phenyl)-5-methoxycarbonyl-2-thiazol-2-yl-1,4-dihydropyrimidin-6-yl]methyl-methyl-amino]hexoxy]-10-methoxy-2-oxo-6,7-dihydrobenzo[a]quinolizine-3-carboxylate (Compound 9d)

To a mixture of crude methyl (4R)-6-(bromomethyl)-4-(2-chloro-4-fluoro-phenyl)-2-thiazol-2-yl-1,4-dihydropyrimidine-5-carboxylate (intermediate I-2, 43 mg, 0.098 mmol) and methyl 6-tert-butyl-10-methoxy-9-[6-(methylamino)hexoxy]-2-oxo-6,7-dihydrobenzo[a]quinolizine-3-carboxylate hydrochloride (compound 9c, 66 mg, 0.098 mmol) in $CH_2Cl_2$ (3 mL) was added DIEA (75.7 mg, 0.59 mmol). The resulting mixture was stirred at room temperature overnight, then diluted with water and extracted with $CH_2Cl_2$ for three times. The combined organic layer was washed with brine, dried over anhydrous $Na_2SO_4$ and concentrated under reduced pressure to afford crude methyl 6-tert-butyl-9-[6-[[(4R)-4-(2-chloro-4-fluoro-phenyl)-5-methoxycarbonyl-2-thiazol-2-yl-1,4-dihydropyrimidin-6-yl]methyl-methyl-amino]hexoxy]-10-methoxy-2-oxo-6,7-dihydrobenzo[a]quinolizine-3-carboxylate (91 mg) as a yellow oil, which was directly used for next step without purification. MS obsd. (ESI$^+$) [(M+H)$^+$]: 834.

Step 4: Preparation of 6-tert-butyl-9-[6-[[(4R)-4-(2-chloro-4-fluoro-phenyl)-5-methoxycarbonyl-2-thiazol-2-yl-1,4-dihydropyrimidin-6-yl]methyl-methyl-amino]hexoxy]-10-methoxy-2-oxo-6,7-dihydrobenzo[a]quinolizine-3-carboxylic Acid (Example 9)

To a solution of crude methyl 6-tert-butyl-9-[6-[[(4R)-4-(2-chloro-4-fluoro-phenyl)-5-methoxycarbonyl-2-thiazol-2-yl-1,4-dihydropyrimidin-6-yl]methyl-methyl-amino]hexoxy]-10-methoxy-2-oxo-6,7-dihydrobenzo[a]quinolizine-3-carboxylate (compound 9d, 91 mg, 0.09 mmol) in THF (2 mL) and $H_2O$ (0.5 mL) was added lithium hydroxide hydrate (31 mg, 0.74 mmol). The resulting mixture was stirred at room temperature for 3 h. The reaction mixture was diluted with water and acidified by HOAc to pH-3. The resulting mixture was extracted with $CH_2Cl_2$ for three times. The combined organic layer was washed with brine, dried and concentrated. The residue was purified by preparative HPLC to afford 6-tert-butyl-9-[6-[[(4R)-4-(2-chloro-4-fluoro-phenyl)-5-methoxycarbonyl-2-thiazol-2-yl-1,4-dihydropyrimidin-6-yl]methyl-methyl-amino]hexoxy]-10-methoxy-2-oxo-6,7-dihydrobenzo[a]quinolizine-3-carboxylic acid (Example 9, 18 mg) as a yellow solid. MS obsd. (ESI$^+$) [(M+H)$^+$]: 820. $^1$H NMR (400 MHz, DMSO-$d_6$) δ=9.69 (s, 1H), 8.71 (s, 1H), 8.03-7.86 (m, 2H), 7.49-7.31 (m, 4H), 7.16 (dt, 1H), 6.99 (s, 1H), 6.03 (s, 1H), 4.55 (d, 1H), 4.06-3.77 (m, 7H), 3.51 (s, 3H), 3.25-3.15 (m, 1H), 2.48-2.44 (m, 1H), 2.32 (s, 3H), 1.76-1.18 (m, 10H), 0.71 (s, 9H).

Example 10

6-tert-butyl-9-[2-[2-[2-[[(3S)-4-[[(4R)-4-(2-chloro-4-fluoro-phenyl)-5-methoxycarbonyl-2-thiazol-2-yl-1,4-dihydropyrimidin-6-yl]methyl]morpholine-3-carbonyl]amino]ethoxy]ethoxy]ethoxy]-10-methoxy-2-oxo-6,7-dihydrobenzo[a]quinolizine-3-carboxylic Acid

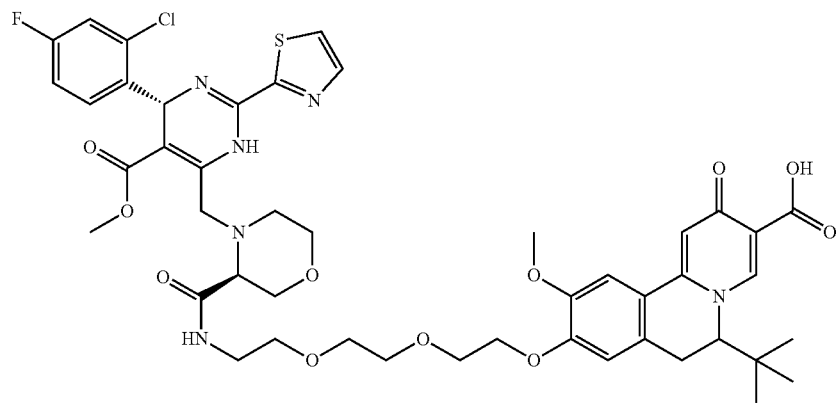 [SMILES: COC(=O)C1=C(CN2CCOC[C@H]2C(=O)NCCOCCOCCOc2cc3c(cc2OC)-c2cc(=O)c(C(=O)O)cn2C(C(C)(C)C)C3)NC(c2nccs2)=N[C@H]1c1ccc(F)cc1Cl]

The title compound was prepared according to the following scheme:
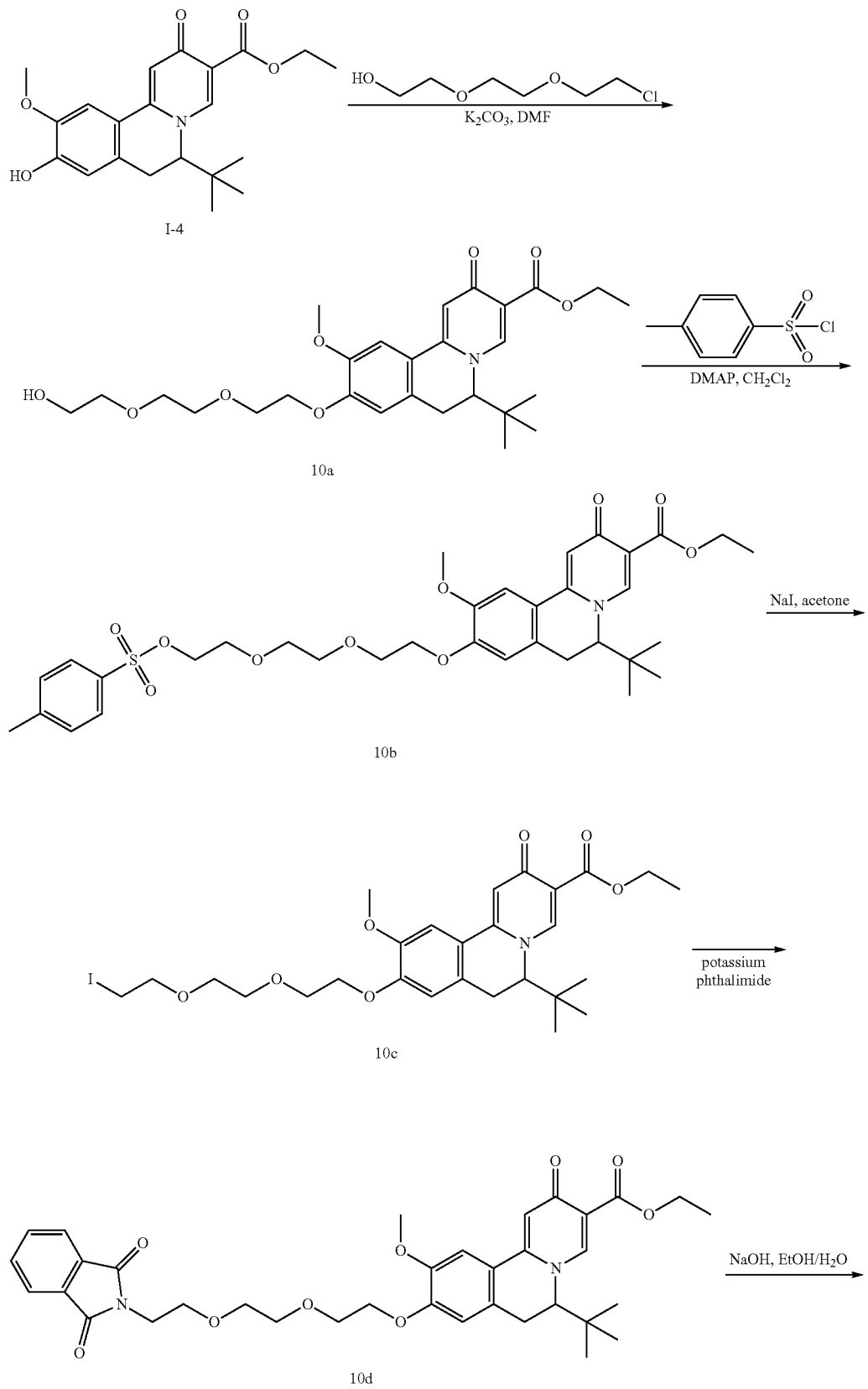

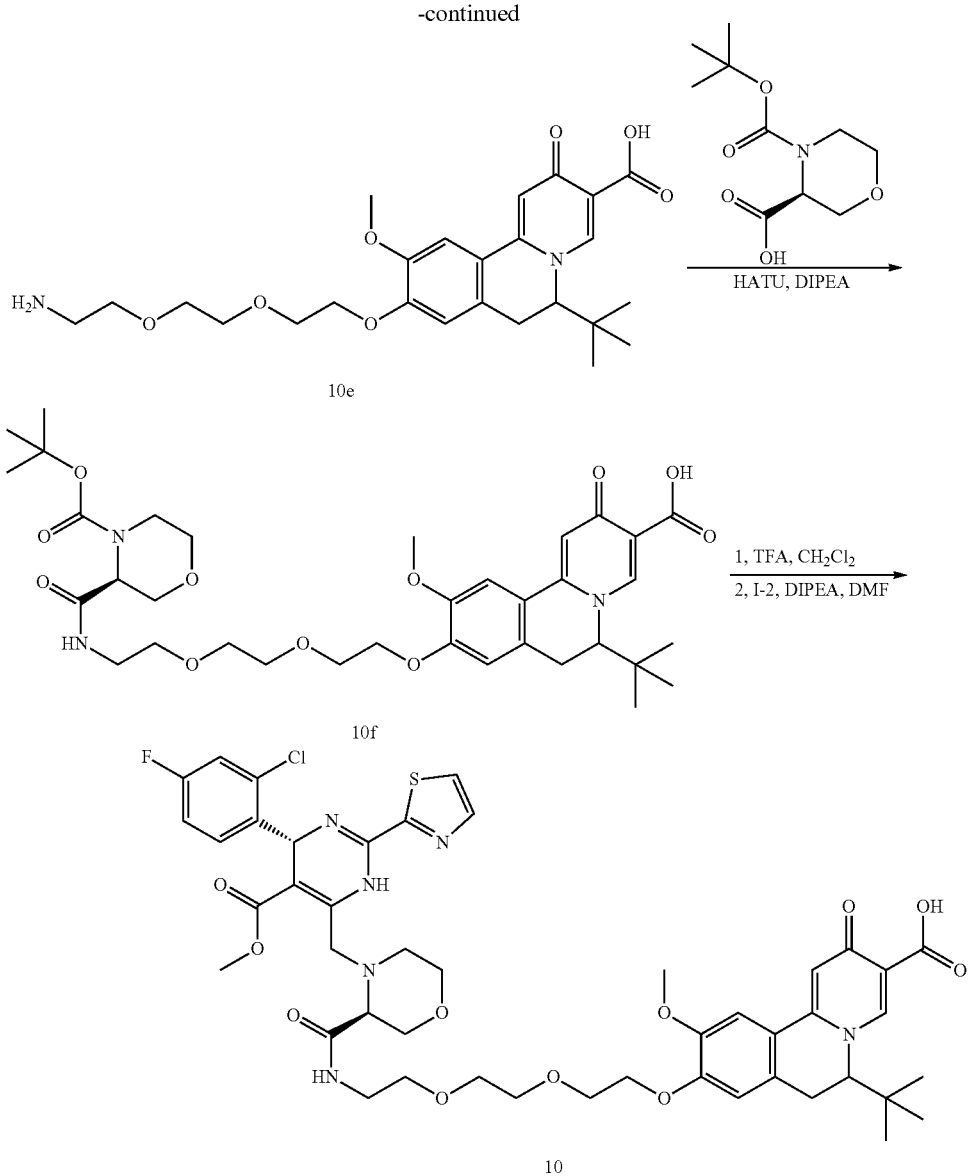

Step 1: Preparation of ethyl 6-tert-butyl-9-[2-[2-(2-hydroxyethoxy)ethoxy]ethoxy]-10-methoxy-2-oxo-6,7-dihydrobenzo[a]quinolizine-3-carboxylate (Compound 10a)

A mixture of ethyl 6-tert-butyl-9-hydroxy-10-methoxy-2-oxo-6,7-dihydrobenzo[a]quinolizine-3-carboxylate (intermediate I-1, 743 mg, 2 mmol), 2-(2-(2-chloroethoxy)ethoxy)ethanol (405 mg, 2.4 mmol), potassium carbonate (553 mg, 4 mmol) and sodium iodide (300 mg, 2 mmol) in DMF (10 mL) was heated to 110° C. for 24 h. After cooling to room temperature, the reaction mixture was partitioned between $CH_2Cl_2$ and water. The separated aqueous layer was extracted with $CH_2Cl_2$ for three times. The combined organic layer was washed with brine, dried and concentrated to give crude ethyl 6-tert-butyl-9-[2-[2-(2-hydroxyethoxy)ethoxy]ethoxy]-10-methoxy-2-oxo-6,7-dihydrobenzo[a]quinolizine-3-carboxylate (compound 10a, 0.99 g) as a brown oil, which was directly used for next step without purification. MS obsd. (ESI$^+$) [(M+H)$^+$]: 503.

Step 2: Preparation of ethyl 6-tert-butyl-10-methoxy-2-oxo-9-[2-[2-[2-(p-tolylsulfonyloxy)ethoxy]ethoxy]ethoxy]-6,7-dihydrobenzo[a]quinolizine-3-carboxylate (Compound 10b)

To a mixture of crude ethyl 6-tert-butyl-9-[2-[2-(2-hydroxyethoxy)ethoxy]ethoxy]-10-methoxy-2-oxo-6,7-dihydrobenzo[a]quinolizine-3-carboxylate (0.91 g, 1.81 mmol), triethylamine (549 mg, 5.42 mmol) and DMAP (22.1 mg, 0.181 mmol) in $CH_2Cl_2$ (8 mL) was added 4-methylbenzene-1-sulfonyl chloride (517 mg, 2.71 mmol) in $CH_2Cl_2$ (5 mL) dropwise at 0° C. under argon. The mixture was allowed to warm to rt and stirred at rt overnight. The reaction mixture was partitioned between $CH_2Cl_2$ and water, and the separated aqueous layer was extracted with $CH_2Cl_2$. The combined organic layer was washed with brine, dried and concentrated. The residue was purified by flash chromatography to afford crude ethyl 6-tert-butyl-10-methoxy-2-oxo-9-[2-[2-[2-(p-tolylsulfonyloxy)ethoxy]ethoxy]ethoxy]-6,7-dihydrobenzo[a]quinolizine-3-carboxylate (compound 10b, 620 mg) as a brown oil, which was directly used for next step without further purification. MS obsd. (ESI$^+$) [(M+H)$^+$]: 658.

Step 3: Preparation of ethyl 6-tert-butyl-9-[2-[2-(2-iodoethoxy)ethoxy]ethoxy]-10-methoxy-2-oxo-6,7-dihydrobenzo[a]quinolizine-3-carboxylate (Compound 10c)

A mixture of ethyl 6-tert-butyl-10-methoxy-2-oxo-9-[2-[2-[2-(p-tolylsulfonyloxy)ethoxy]ethoxy]ethoxy]-6,7-dihydrobenzo[a]quinolizine-3-carboxylate (554 mg, 0.84 mmol) and sodium iodide (1.26 g, 8.4 mmol) in acetone (10 mL) was refluxed for 20 h. After cooling to room temperature, the reaction mixture was partitioned between EtOAc and water, and then extracted with EtOAc for three times. The combined organic layer was washed with sat. NaHCO$_3$ aqueous solution and brine, dried and concentrated to give crude ethyl 6-tert-butyl-9-[2-[2-(2-iodoethoxy)ethoxy]ethoxy]-10-methoxy-2-oxo-6,7-dihydrobenzo[a]quinolizine-3-carboxylate (compound 10c, 512 mg) as a brown oil, which was directly used for next step without purification. MS obsd. (ESI$^+$) [(M+H)$^+$]: 614.

Step 4: Preparation of ethyl 6-tert-butyl-9-[2-[2-[2-(1,3-dioxoisoindolin-2-yl)ethoxy]ethoxy]ethoxy]-10-methoxy-2-oxo-6,7-dihydrobenzo[a]quinolizine-3-carboxylate (Compound 10d)

A mixture of crude ethyl 6-tert-butyl-9-[2-[2-(2-iodoethoxy)ethoxy]ethoxy]-10-methoxy-2-oxo-6,7-dihydrobenzo[a]quinolizine-3-carboxylate (123 mg, 0.2 mmol) and potassium phthalimide (45 mg, 0.24 mmol) in DMF (1 mL) was heated at 90° C. for 16 h. After cooling to room temperature, the reaction mixture was partitioned between EtOAc and water, and then extracted with EtOAc for three times. The combined organic layer was washed with brine, dried and concentrated to give crude ethyl 6-tert-butyl-9-[2-[2-[2-(1,3-dioxoisoindolin-2-yl)ethoxy]ethoxy]ethoxy]-10-methoxy-2-oxo-6,7-dihydrobenzo[a]quinolizine-3-carboxylate (compound 10d, 135 mg) as a brown oil, which was directly used for next step without purification. MS obsd. (ESI$^+$) [(M+H)$^+$]: 633.

Step 5: Preparation of 9-[2-[2-(2-aminoethoxy)ethoxy]ethoxy]-6-tert-butyl-10-methoxy-2-oxo-6,7-dihydrobenzo[a]quinolizine-3-carboxylic Acid (Compound 10e)

To a solution of crude ethyl 6-tert-butyl-9-[2-[2-[2-(1,3-dioxoisoindolin-2-yl)ethoxy]ethoxy]ethoxy]-10-methoxy-2-oxo-6,7-dihydrobenzo[a]quinolizine-3-carboxylate (135 mg, 0.19 mmol) in EtOH (1 mL) was added 10 M aqueous NaOH (0.58 mL, 5.8 mmol). The resulting mixture was heated at 110° C. for 72 h. After cooling to room temperature, the reaction mixture was acidified by HOAc, and then partitioned between CH$_2$Cl$_2$ and water. The separated aqueous layer was extracted with CH$_2$Cl$_2$. The combined organic layer was washed with brine, dried and concentrated to give crude 9-[2-[2-(2-aminoethoxy)ethoxy]ethoxy]-6-tert-butyl-10-methoxy-2-oxo-6,7-dihydrobenzo[a]quinolizine-3-carboxylic acid (compound 10e, 62 mg) as a brown oil, which was directly used for next step without purification. MS obsd. (ESI$^+$) [(M+H)$^+$]: 475.

Step 6: Preparation of 9-[2-[2-[2-[[(3S)-4-tert-butoxycarbonylmorpholine-3-carbonyl]amino]ethoxy]ethoxy]ethoxy]-6-tert-butyl-10-methoxy-2-oxo-6,7-dihydrobenzo[a]quinolizine-3-carboxylic Acid (Compound 10f)

A mixture of crude (3S)-4-tert-butoxycarbonylmorpholine-3-carboxylic acid (23 mg, 0.1 mmol), HATU (38 mg, 0.1 mmol) and DIPEA (64 mg, 0.5 mmol) in CH$_2$Cl$_2$ (1 mL) was stirred at room temperature for 1 h. Then crude 9-[2-[2-(2-aminoethoxy)ethoxy]ethoxy]-6-tert-butyl-10-methoxy-2-oxo-6,7-dihydrobenzo[a]quinolizine-3-carboxylic acid (47 mg, 0.1 mmol) in CH$_2$Cl$_2$ (1 mL) was added and stirred at room temperature for 5 h. The resulting mixture was partitioned between CH$_2$Cl$_2$ and water. The separated aqueous layer was extracted with CH$_2$Cl$_2$ for three times. The combined organic layer was washed with brine, dried and concentrated to give crude 9-[2-[2-[2-[[(3S)-4-tert-butoxycarbonylmorpholine-3-carbonyl]amino]ethoxy]ethoxy]ethoxy]-6-tert-butyl-10-methoxy-2-oxo-6,7-dihydrobenzo[a]quinolizine-3-carboxylic acid (compound 10f, 59 mg) as a brown oil, which was directly used for next step without purification. MS obsd. (ESI$^+$) [(M+H)$^+$]: 688.

Step 7: Preparation of 6-tert-butyl-9-[2-[2-[2-[[(3S)-4-[[(4R)-4-(2-chloro-4-fluoro-phenyl)-5-methoxycarbonyl-2-thiazol-2-yl-1,4-dihydropyrimidin-6-yl]methyl]morpholine-3-carbonyl]amino]ethoxy]ethoxy]ethoxy]-10-methoxy-2-oxo-6,7-dihydrobenzo[a]quinolizine-3-carboxylic Acid (Example 10)

A mixture of crude 9-[2-[2-[2-[[(3S)-4-tert-butoxycarbonylmorpholine-3-carbonyl]amino]ethoxy]ethoxy]ethoxy]-6-tert-butyl-10-methoxy-2-oxo-6,7-dihydrobenzo[a]quinolizine-3-carboxylic acid (59 mg, 85.8 µmol) and TFA (0.3 mL) in CH$_2$Cl$_2$ (3 mL) was stirred at room temperature for 2 h. After removing the excess solvent under reduced pressure, the residue was dissolved in DMF (2 mL). To the resulting solution was added sodium iodide (12 mg, 0.81 mmol), DIPEA (105 mg, 8.1 mmol) and methyl (4R)-6-(bromomethyl)-4-(2-chloro-4-fluoro-phenyl)-2-thiazol-2-yl-1,4-dihydropyrimidine-5-carboxylate (intermediate I-2, 36 mg, 0.81 mmol). The resulting mixture was stirred at 55° C. for 2 h. After cooling to room temperature, the reaction mixture was partitioned between CH$_2$Cl$_2$ and water, the separated aqueous layer was extracted with CH$_2$Cl$_2$ for three times. The combined organic layer was washed with brine, dried, concentrated to give some crude product, the crude product was purified by preparative HPLC to afford 6-tert-butyl-9-[2-[2-[2-[[(3S)-4-[[(4R)-4-(2-chloro-4-fluoro-phenyl)-5-methoxycarbonyl-2-thiazol-2-yl-1,4-dihydropyrimidin-6-yl]methyl]morpholine-3-carbonyl]amino]ethoxy]ethoxy]ethoxy]-10-methoxy-2-oxo-6,7-dihydrobenzo[a]quinolizine-3-carboxylic acid (Example 10, 13 mg) as a yellow solid. MS obsd. (ESI$^+$) [(M+H)$^+$]: 951. $^1$H NMR (400 MHz, CDCl$_3$) δ=8.40 (br s, 1H), 7.87 (br s, 2H), 7.54 (br s, 1H), 7.34-7.24 (m, 1H), 7.07 (d, 3H), 6.90 (s, 1H), 6.70 (s, 1H), 6.12 (br s, 1H), 4.38 (d, 1H), 4.26-4.06 (m, 3H), 4.02-3.89 (m, 2H), 3.84 (s, 3H), 3.80-3.70 (m, 2H), 3.69-3.59 (m, 2H), 3.51 (s, 3H), 3.50-3.41 (m, 3H), 3.39-2.91 (m, 4H), 0.74 (br s, 9H)

Example 11
6-tert-butyl-9-[2-[2-[2-[2-carboxy-4-[[(4R)-4-(2-chloro-4-fluoro-phenyl)-5-methoxycarbonyl-2-thiazol-2-yl-1,4-dihydropyrimidin-6-yl]methyl]piperazin-1-yl]ethoxy]ethoxy]ethoxy]-10-methoxy-2-oxo-6,7-dihydrobenzo[a]quinolizine-3-carboxylic Acid
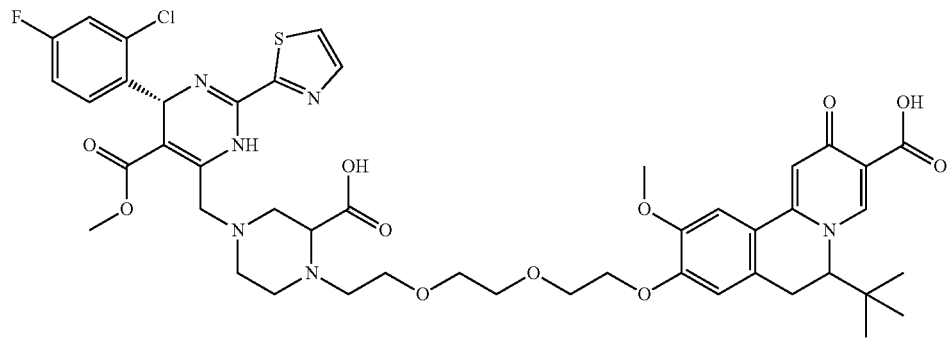
The title compound was prepared according to the following scheme:
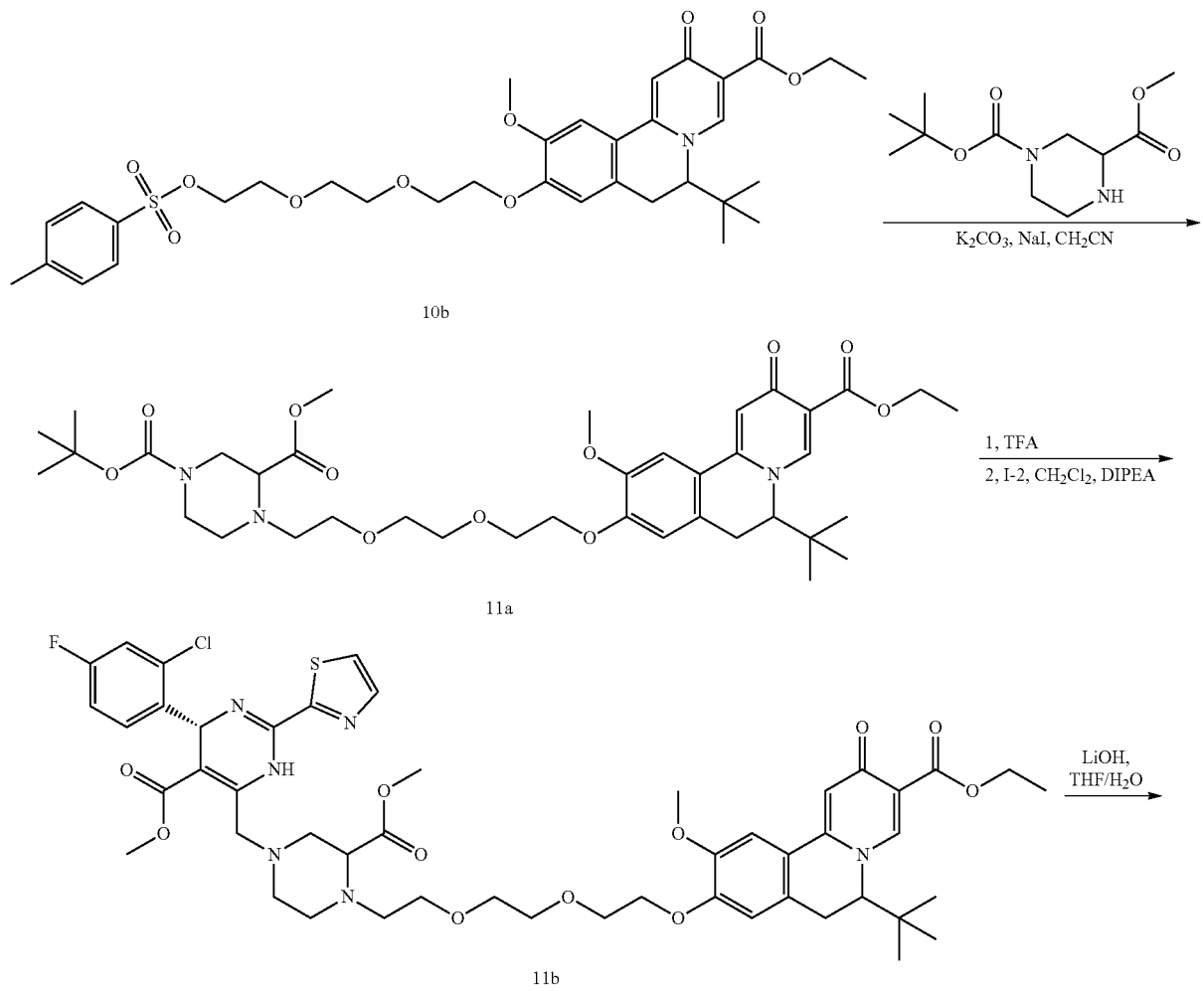

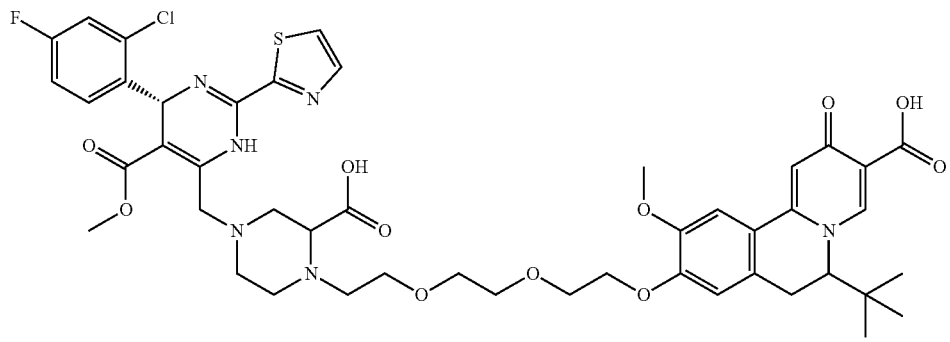 [SMILES: COC(=O)C1=C(CN2CCN(CCOCCOCCOc3cc4c(cc3OC)-c3cc(=O)c(C(=O)O)cn3C(C(C)(C)C)C4)C(C(=O)O)C2)NC(c2nccs2)=N[C@H]1c1ccc(F)cc1Cl]

11

Step 1: Preparation of O1-tert-butyl O3-methyl 4-[2-[2-[2-[(6-tert-butyl-3-ethoxycarbonyl-10-methoxy-2-oxo-6,7-dihydrobenzo[a]quinolizin-9-yl)oxy]ethoxy]ethoxy]ethyl]piperazine-1,3-dicarboxylate (Compound 11a)

A mixture of crude ethyl 6-tert-butyl-10-methoxy-2-oxo-9-[2-[2-[2-(p-tolylsulfonyloxy)ethoxy]ethoxy]ethoxy]-6,7-dihydrobenzo[a]quinolizine-3-carboxylate (compound 10b, 65.8 mg, 0.1 mmol), 1-tert-butyl 3-methyl piperazine-1,3-dicarboxylate (29 mg, 0.12 mmol), potassium carbonate (28 mg, 0.2 mmol) and sodium iodide (15 mg, 0.1 mmol) in acetonitrile (1 mL) was heated at 90° C. for 20 h. After cooling to room temperature, the reaction mixture was partitioned between CH$_2$Cl$_2$ and water, and then extracted with CH$_2$Cl$_2$ for three times. The combined organic layer was washed with brine, dried and concentrated to give crude O1-tert-butyl O3-methyl 4-[2-[2-[2-[(6-tert-butyl-3-ethoxycarbonyl-10-methoxy-2-oxo-6,7-dihydrobenzo[a]quinolizin-9-yl)oxy]ethoxy]ethoxy]ethyl]piperazine-1,3-dicarboxylate (compound 11a, 85 mg) as a brown oil, which was directly used for next step without further purification. MS obsd. (ESI$^+$) [(M+H)$^+$]: 730.

Step 2: Preparation of ethyl 6-tert-butyl-9-[2-[2-[2-[4-[[(4R)-4-(2-chloro-4-fluoro-phenyl)-5-methoxycarbonyl-2-thiazol-2-yl-1,4-dihydropyrimidin-6-yl]methyl]-2-methoxycarbonyl-piperazin-1-yl]ethoxy]ethoxy]ethoxy]-10-methoxy-2-oxo-6,7-dihydrobenzo[a]quinolizine-3-carboxylate (Compound 11b)

To a solution of crude O1-tert-butyl O3-methyl 4-[2-[2-[2-[(6-tert-butyl-3-ethoxycarbonyl-10-methoxy-2-oxo-6,7-dihydrobenzo[a]quinolizin-9-yl)oxy]ethoxy]ethoxy]ethyl]piperazine-1,3-dicarboxylate (85 mg, 0.093 mmol) in CH$_2$Cl$_2$ (3 mL) was added TFA (0.5 mL). The resulting mixture was stirred at room temperature for 3 h, and then concentrated under reduced pressure. The residue was dissolved in CH$_2$Cl$_2$ (3 mL). To the solution was added DIPEA (109 mg, 0.085 mmol) and methyl (4R)-6-(bromomethyl)-4-(2-chloro-4-fluoro-phenyl)-2-thiazol-2-yl-1,4-dihydropyrimidine-5-carboxylate (intermediate I-2, 38 mg, 0.085 mmol). The resulting mixture was stirred at room temperature for 16 h, and then partitioned between CH$_2$Cl$_2$ and water. The separated aqueous layer was extracted with CH$_2$Cl$_2$ for three times. The combined organic layer was washed with brine, dried and concentrated to give crude ethyl 6-tert-butyl-9-[2-[2-[2-[4-[[(4R)-4-(2-chloro-4-fluoro-phenyl)-5-methoxycarbonyl-2-thiazol-2-yl-1,4-dihydropyrimidin-6-yl]methyl]-2-methoxycarbonyl-piperazin-1-yl]ethoxy]ethoxy]ethoxy]-10-methoxy-2-oxo-6,7-dihydrobenzo[a]quinolizine-3-carboxylate (compound 11b, 97 mg) as a yellow oil which was directly used for next step without purification. MS obsd. (ESI$^+$) [(M+H)$^+$]: 993.

Step 3: Preparation of 6-tert-butyl-9-[2-[2-[2-[2-carboxy-4-[[(4R)-4-(2-chloro-4-fluoro-phenyl)-5-methoxycarbonyl-2-thiazol-2-yl-1,4-dihydropyrimidin-6-yl]methyl]piperazin-1-yl]ethoxy]ethoxy]ethoxy]-10-methoxy-2-oxo-6,7-dihydrobenzo[a]quinolizine-3-carboxylic Acid (Example 11)

To a solution of crude ethyl 6-tert-butyl-9-[2-[2-[2-[4-[[(4R)-4-(2-chloro-4-fluoro-phenyl)-5-methoxycarbonyl-2-thiazol-2-yl-1,4-dihydropyrimidin-6-yl]methyl]-2-methoxycarbonyl-piperazin-1-yl]ethoxy]ethoxy]ethoxy]-10-methoxy-2-oxo-6,7-dihydrobenzo[a]quinolizine-3-carboxylate (97 mg, 0.078 mmol) in THF (3 mL) and H$_2$O (1 mL) was added lithium hydroxide hydrate (66 mg, 1.56 mmol). The resulting mixture was stirred at room temperature overnight. The reaction mixture was acidified by HOAc, and then partitioned between CH$_2$Cl$_2$ and water. The separated aqueous layer was extracted with CH$_2$Cl$_2$ for three times. The combined organic layer was washed with brine, dried and concentrated. The residue was purified by preparative HPLC to afford 6-tert-butyl-9-[2-[2-[2-[2-carboxy-4-[[(4R)-4-(2-chloro-4-fluoro-phenyl)-5-methoxycarbonyl-2-thiazol-2-yl-1,4-dihydropyrimidin-6-yl]methyl]piperazin-1-yl]ethoxy]ethoxy]ethoxy]-10-methoxy-2-oxo-6,7-dihydrobenzo[a]quinolizine-3-carboxylic acid (Example 11, 18 mg) as a yellow powder. MS obsd. (ESI$^+$) [(M+H)$^+$]: 951.
$^1$H NMR (400 MHz, CDCl$_3$) δ=8.40 (s, 1H), 7.78 (s, 1H), 7.50 (s, 1H), 7.28-7.19 (m, 1H), 7.10-6.98 (m, 3H), 6.93-6.82 (m, 2H), 6.70 (s, 1H), 6.06 (d, 1H), 4.39-4.08 (m, 4H), 4.04-3.94 (br s, 1H), 3.88-3.05 (m, 21H), 0.71 (s, 9H)

Example 12
6-tert-butyl-9-[4-carboxy-6-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylic Acid
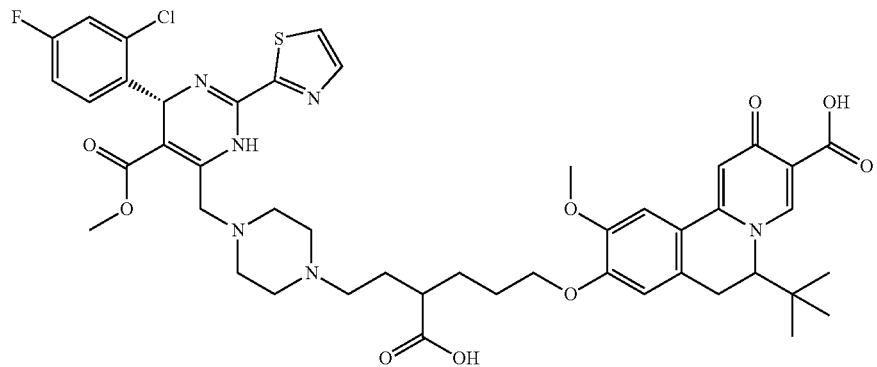 [SMILES: COC(=O)C1=C(CN2CCN(CCC(CCCOc3cc4c(cc3OC)-c3cc(=O)c(C(=O)O)cn3C(C(C)(C)C)C4)C(=O)O)CC2)NC(c2nccs2)=N[C@H]1c1ccc(F)cc1Cl]
The title compound was prepared according to the following scheme:
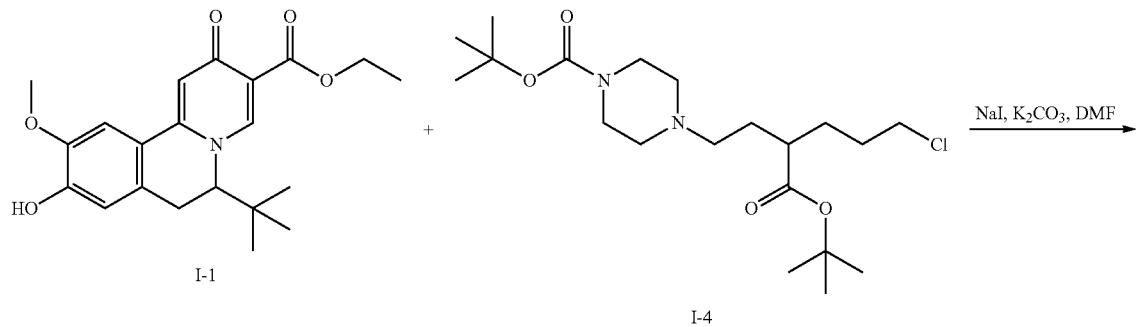
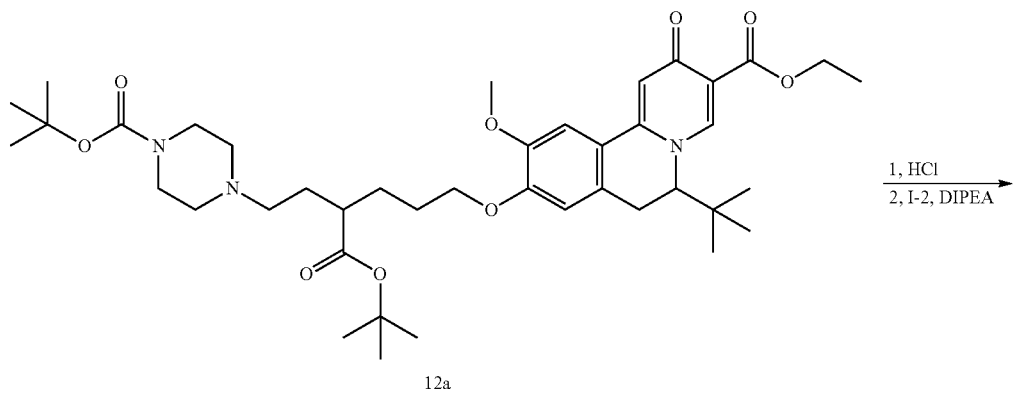

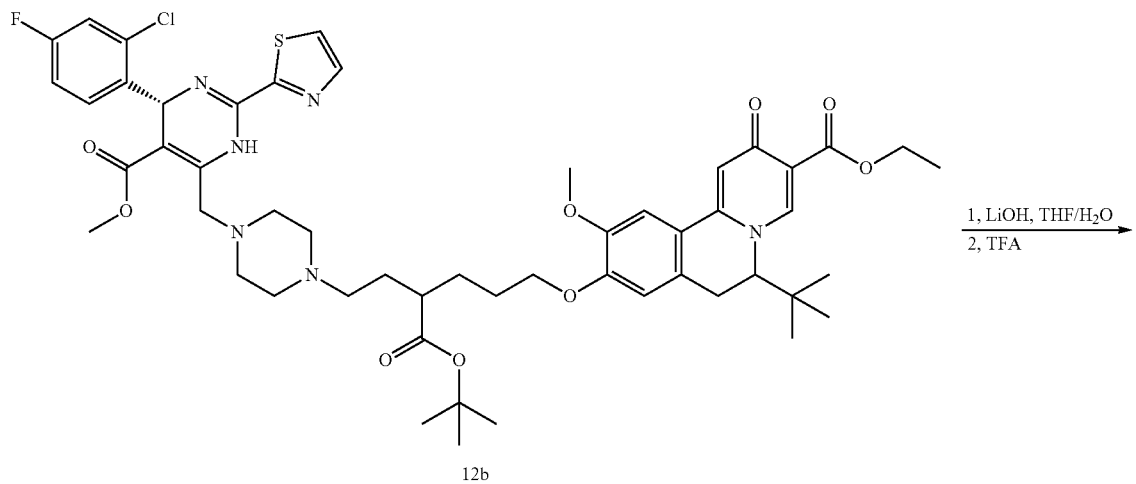

12b

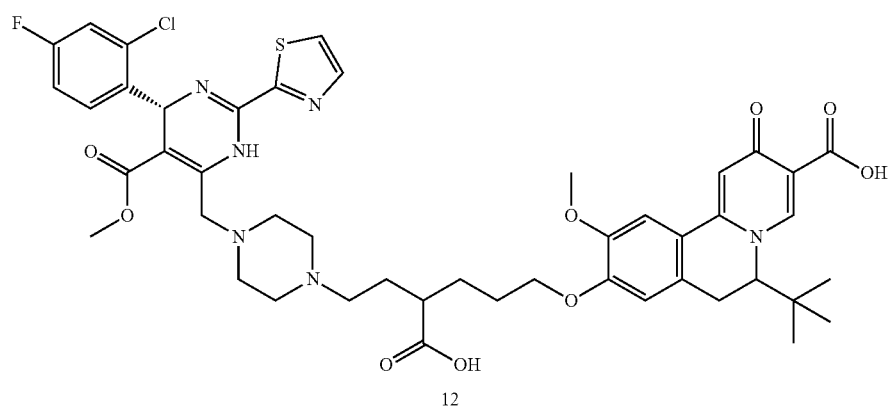

12

Step 1: Preparation of ethyl 9-[4-tert-butoxycarbonyl-6-(4-tert-butoxycarbonylpiperazin-1-yl)hexoxy]-6-tert-butyl-10-methoxy-2-oxo-6,7-dihydrobenzo[a]quinolizine-3-carboxylate (Compound 12a)

To a mixture of ethyl 6-tert-butyl-9-hydroxy-10-methoxy-2-oxo-6,7-dihydrobenzo[a]quinolizine-3-carboxylate (intermediate I-1, 106 mg, 0.29 mmol) and tert-butyl 4-(3-tert-butoxycarbonyl-6-chloro-hexyl)piperazine-1-carboxylate (intermediate I-4, 129 mg, 0.29 mmol) in DMF (2 mL) was added potassium carbonate (119 mg, 0.87 mmol) and sodium iodide (43 mg, 0.29 mmol). The mixture was heated at 60° C. for 16 h, and then partitioned with EtOAc and water. The separated aqueous layer was extracted with EtOAc for three times. The combined organic layer was washed with brine, dried and concentrated to give crude ethyl 9-[4-tert-butoxycarbonyl-6-(4-tert-butoxycarbonylpiperazin-1-yl)hexoxy]-6-tert-butyl-10-methoxy-2-oxo-6,7-dihydrobenzo[a]quinolizine-3-carboxylate (compound 12a, 151 mg) as a brown oil which was directly used for next step without purification. MS obsd. (ESI$^+$) [(M+H)$^+$]: 740.

Step 2: Preparation of ethyl 9-[4-tert-butoxycarbonyl-6-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-6-tert-butyl-10-methoxy-2-oxo-6,7-dihydrobenzo[a]quinolizine-3-carboxylate (Compound 12b)

A mixture of ethyl 9-[4-tert-butoxycarbonyl-6-(4-tert-butoxycarbonylpiperazin-1-yl)hexoxy]-6-tert-butyl-10-methoxy-2-oxo-6,7-dihydrobenzo[a]quinolizine-3-carboxylate (compound 12a, 151 mg, 0.2 mmol) and 1 M hydrogen chloride in ethyl acetate (5 mL, 5 mmol) was stirred at room temperature for 2 h. After removing the excess solvent under reduced pressure, the residue was dissolved in in DMF (2 mL). To the solution was added DIPEA (121 mg, 0.94 mmol) and methyl (4R)-6-(bromomethyl)-4-(2-chloro-4-fluoro-phenyl)-2-thiazol-2-yl-1,4-dihydropyrimidine-5-carboxylate (intermediate I-2, 83 mg, 0.19 mmol). The mixture was stirred at room temperature for 20 h. Additional methyl (4R)-6-(bromomethyl)-4-(2-chloro-4-fluoro-phenyl)-2-thiazol-2-yl-1,4-dihydropyrimidine-5-carboxylate (83 mg, 0.19 mmol) and sodium iodide (28 mg, 0.19 mmol) was added to the reaction mixture. The resulting mixture was heated at 50° C. for 5 h, and then diluted with CH$_2$Cl$_2$ and water. The aqueous layer was extracted with CH$_2$Cl$_2$ for three times. The combined organic layer was washed with water and brine, dried and concentrated to give crude ethyl 9-[4-tert-butoxycarbonyl-6-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-6-tert-butyl-10-methoxy-2-oxo-6,7-dihydrobenzo[a]quinolizine-3-carboxylate (compound 12b, 303 mg) as a brown oil, which was directly used for next step without purification. MS obsd. (ESI$^+$) [(M+H)$^+$]: 1003.

Step 3: Preparation of 6-tert-butyl-9-[4-carboxy-6-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylic Acid (Example 12)

A mixture of crude ethyl 9-[4-tert-butoxycarbonyl-6-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-6-tert-butyl-10-methoxy-2-oxo-6,7-dihydrobenzo[a]quinolizine-3-carboxylate (compound 12b, 303 mg, 0.3 mmol) and lithium hydroxide hydrate (127 mg, 3 mmol) in THF (3 mL) and H$_2$O (1 mL) was stirred at room temperature for 1 h. The reaction mixture was acidified by HOAc, partitioned with CH$_2$Cl$_2$ and water, then extracted with CH$_2$Cl$_2$ for three times. The combined organic layer was washed with brine, dried and concentrated. To the residue was added TFA (3 mL), and then the resulting mixture was stirred at room temperature for 1 h. After removing the excess solvent under reduced pressure, the residue was purified by preparative HPLC to afford 6-tert-butyl-9-[4-carboxy-6-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylic acid (Example 12, 15 mg) as a yellow solid. MS obsd. (ESI$^+$) [(M+H)$^+$]: 919. $^1$H NMR (400 MHz, DMSO-d$_6$) δ=9.68 (s, 1H), 8.71 (s, 1H), 8.06-7.89 (m, 2H), 7.50-7.32 (m, 4H), 7.23-6.98 (m, 3H), 6.80-6.70 (m, 1H), 6.03 (s, 1H), 4.56 (d, 1H), 4.13-3.98 (m, 2H), 3.95-3.80 (m, 6H), 3.51 (s, 3H), 3.42-3.18 (m, 2H), 2.35 (br d, J=6.8 Hz, 2H), 1.83-1.53 (m, 6H), 0.72 (s, 9H)

Example 13

6-tert-butyl-9-[6-[[(3S)-4-[[(4R)-4-(2-chloro-4-fluoro-phenyl)-5-methoxycarbonyl-2-thiazol-2-yl-1,4-dihydropyrimidin-6-yl]methyl]morpholine-3-carbonyl]amino]hexoxy]-10-methoxy-2-oxo-6,7-dihydrobenzo[a]quinolizine-3-carboxylic Acid

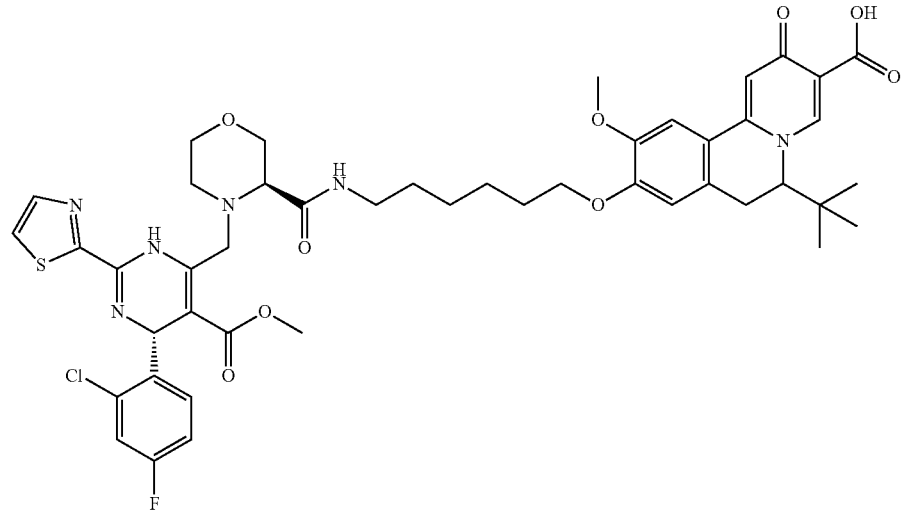 [SMILES: COC(=O)C1=C(CN2CCOC[C@H]2C(=O)NCCCCCCOc2cc3c(cc2OC)-c2cc(=O)c(C(=O)O)cn2C(C(C)(C)C)C3)NC(c2nccs2)=N[C@H]1c1ccc(F)cc1Cl]

The title compound was prepare according to the following scheme:

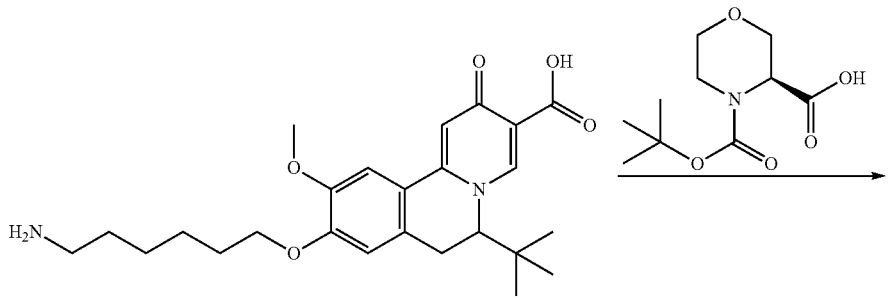

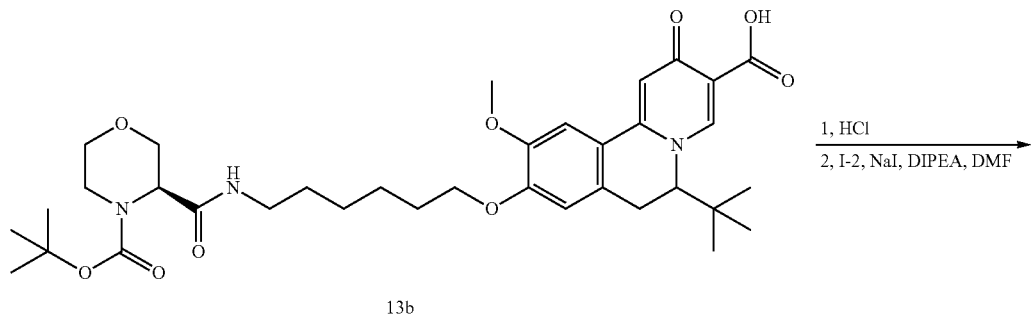

13b

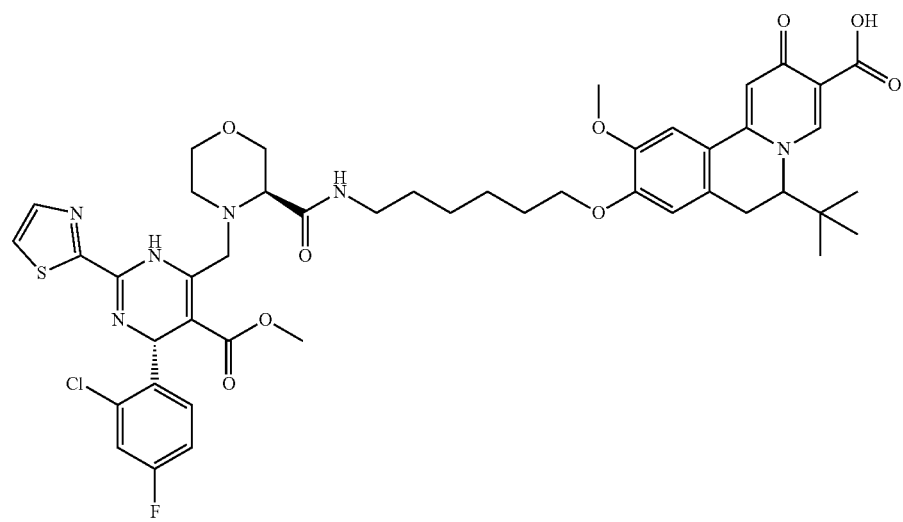

13

Step 1: Preparation of 9-[6-[[(3S)-4-tert-butoxycarbonylmorpholine-3-carbonyl]amino]hexoxy]-6-tert-butyl-10-methoxy-2-oxo-6,7-dihydrobenzo[a]quinolizine-3-carboxylic Acid (Compound 13b)

A solution of (3S)-4-tert-butoxycarbonylmorpholine-3-carboxylic acid (23 mg, 0.1 mmol), 9-(6-aminohexoxy)-6-tert-butyl-10-methoxy-2-oxo-6,7-dihydrobenzo[a]quinolizine-3-carboxylic acid hydrochloride (compound 13a, 48 mg, 0.1 mmol, prepared according to US20150210682), HATU (38 mg, 0.1 mmol) and DIPEA (52 mg, 0.4 mmol) in DMF (1 mL) was stirred at room temperature for 1 h. The mixture was diluted with water and extracted with CH$_2$Cl$_2$ for three times. The combined organic layer was washed with brine, dried and concentrated to afford crude 9-[6-[[(3S)-4-tert-butoxycarbonylmorpholine-3-carbonyl]amino]hexoxy]-6-tert-butyl-10-methoxy-2-oxo-6,7-dihydrobenzo[a]quinolizine-3-carboxylic acid ((compound 13b, 62 mg) as a yellow oil which was directly used for next step without purification. MS obsd. (ESI$^+$) [(M+H)$^+$]: 656.

Step 2: Preparation of 6-tert-butyl-9-[6-[[(3S)-4-[[(4R)-4-(2-chloro-4-fluoro-phenyl)-5-methoxycarbonyl-2-thiazol-2-yl-1,4-dihydropyrimidin-6-yl]methyl]morpholine-3-carbonyl]amino]hexoxy]-10-methoxy-2-oxo-6,7-dihydrobenzo[a]quinolizine-3-carboxylic Acid (Example 13)

A mixture of crude 9-[6-[[(3S)-4-tert-butoxycarbonylmorpholine-3-carbonyl]amino]hexoxy]-6-tert-butyl-10-methoxy-2-oxo-6,7-dihydrobenzo[a]quinolizine-3-carboxylic acid (62 mg, 0.95 mmol) and 1M hydrogen chloride in EtOAc (5 mL, 5 mmol) was stirred at room temperature for 2 h. After removing the excess solvent under reduced pressure, the residue was dissolved in DMF (2 mL). To the solution was added methyl (4R)-6-(bromomethyl)-4-(2-chloro-4-fluoro-phenyl)-2-thiazol-2-yl-1,4-dihydropyrimidine-5-carboxylate (intermediate I-2, 57.8 mg, 0.13 mmol), DIPEA (84 mg, 0.65 mmol) and sodium iodide (29 mg, 0.19 mmol). The mixture was heated at 55° C. for 2 h, and then diluted with water and extracted with CH$_2$Cl$_2$ for three times. The combined organic layer was washed with brine, dried and concentrated. The residue was purified by preparative HPLC to afford 6-tert-butyl-9-[6-[[(3S)-4-[[(4R)-4-(2-chloro-4-fluoro-phenyl)-5-methoxycarbonyl-2-thiazol-2-yl-1,4-dihydropyrimidin-6-yl]methyl]morpholine-3-carbonyl]amino]hexoxy]-10-methoxy-2-oxo-6,7-dihydrobenzo[a]quinolizine-3-carboxylic acid (Example 13, 17 mg) as a yellow solid. MS obsd. (ESI+) [(M+H)+]: 919. $^1$H NMR (400 MHz, METHANOL-d$_4$) δ=8.69 (s, 1H), 7.98 (d, 1H), 7.74 (d, 1H), 7.45-7.38 (m, 2H), 7.29 (s, 1H), 7.22 (dd, 1H), 7.05 (dt, 1H), 6.98 (s, 1H), 6.11 (s, 1H), 4.43 (d, 1H), 4.16-4.03 (m, 3H), 3.98-3.69 (m, 8H), 3.58 (s, 3H), 3.51-3.42 (m, 1H), 3.30-3.18 (m, 3H), 3.07-2.98 (m, 1H), 2.64-2.55 (m, 1H), 1.86-1.76 (m, 2H), 1.59-1.45 (m, 4H), 1.44-1.28 (m, 3H), 0.84 (s, 9H)

Example 14

6-tert-butyl-9-[6-[[4-(2-chloro-4-fluoro-phenyl)-5-ethoxycarbonyl-2-thiazol-2-yl-1,4-dihydropyrimidin-6-yl]methoxy]hexoxy]-10-methoxy-2-oxo-6,7-dihydrobenzo[a]quinolizine-3-carboxylic Acid

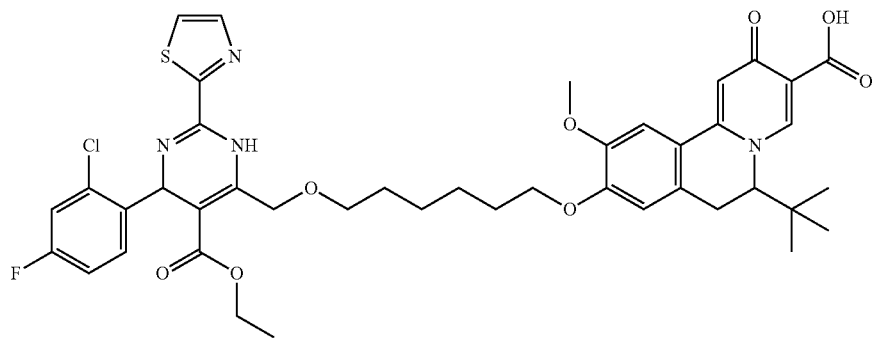 [SMILES: CCOC(=O)C1=C(COCCCCCCOc2cc3c(cc2OC)-c2cc(=O)c(C(=O)O)cn2C(C(C)(C)C)C3)NC(c2nccs2)=NC1c1ccc(F)cc1Cl]

The title compound was prepared according to the following scheme:

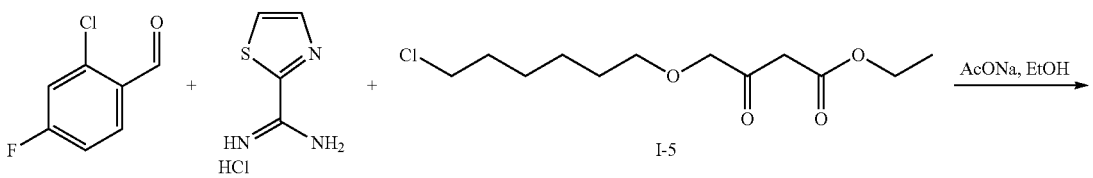

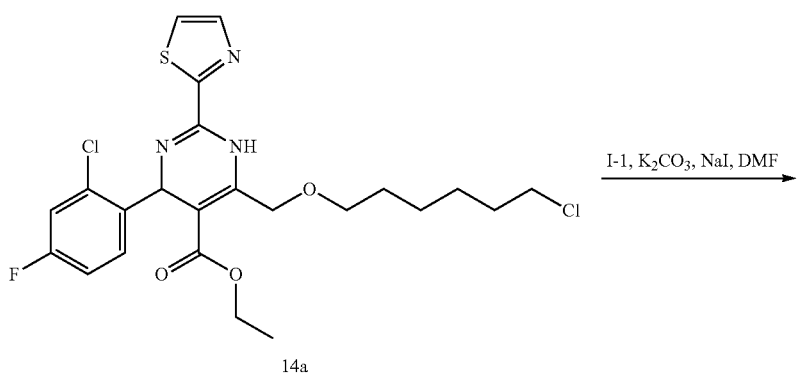

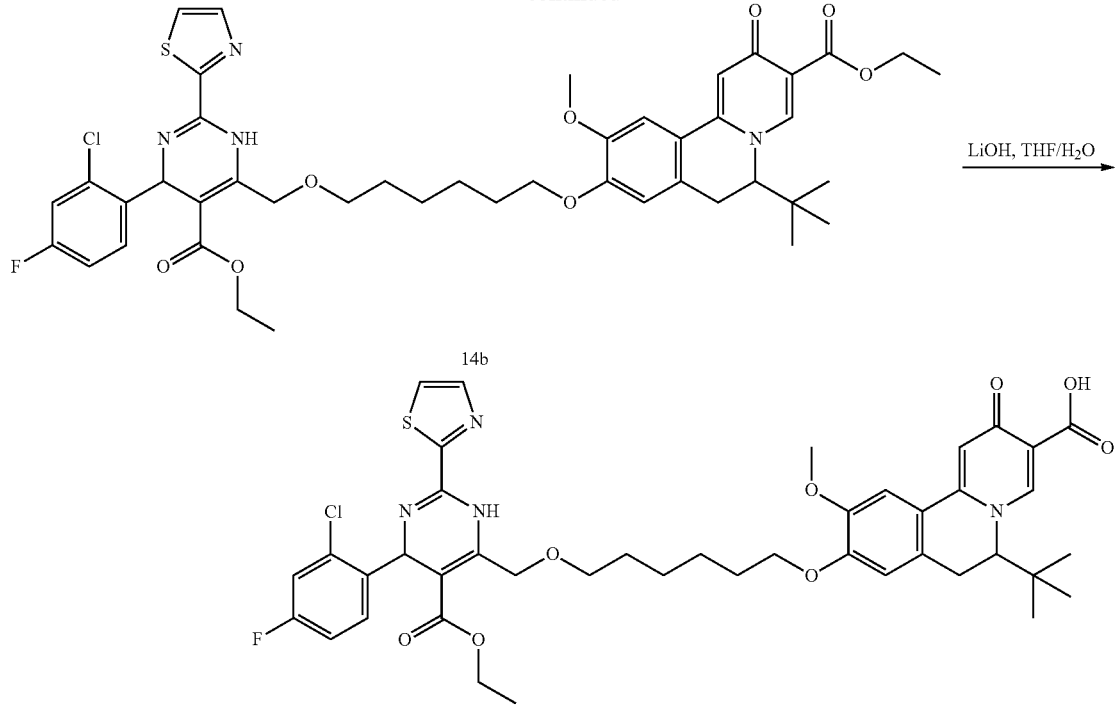

Step 1: Preparation of ethyl 4-(2-chloro-4-fluoro-phenyl)-6-(6-chlorohexoxymethyl)-2-thiazol-2-yl-1,4-dihydropyrimidine-5-carboxylate (Compound 14a)

A mixture of 2-chloro-4-fluorobenzaldehyde (157 mg, 0.99 mmol), ethyl 4-(6-chlorohexoxy)-3-oxo-butanoate (intermediate I-5, 452 mg, 0.99 mmol), thiazole-2-carboximidamide hydrochloride (162 mg, 0.99 mmol) and sodium acetate (162 mg, 1.98 mmol) in EtOH (5 mL) was heated at 80° C. for 40 h. After cooling to room temperature, the mixture was diluted with water and extracted with EtOAc for three times. The combined organic layer was washed with brine, dried and concentrated to afford ethyl 4-(2-chloro-4-fluoro-phenyl)-6-(6-chlorohexoxymethyl)-2-thiazol-2-yl-1,4-dihydropyrimidine-5-carboxylate (compound 14a, 692 mg) as a yellow oil. MS obsd. (ESI$^+$) [(M+H)$^+$]: 514.

Step 2: Preparation of ethyl 6-tert-butyl-9-[6-[[4-(2-chloro-4-fluoro-phenyl)-5-ethoxycarbonyl-2-thiazol-2-yl-1,4-dihydropyrimidin-6-yl]methoxy]hexoxy]-10-methoxy-2-oxo-6,7-dihydrobenzo[a]quinolizine-3-carboxylate (Compound 14b)

A mixture of ethyl 6-tert-butyl-9-hydroxy-10-methoxy-2-oxo-6,7-dihydrobenzo[a]quinolizine-3-carboxylate (intermediate I-1, 581 mg, 1.56 mmol) and potassium carbonate (432 mg, 3.13 mmol) in DMF (3 mL) was stirred at 80° C. for 30 min. Then ethyl 4-(2-chloro-4-fluoro-phenyl)-6-(6-chlorohexoxymethyl)-2-thiazol-2-yl-1,4-dihydropyrimidine-5-carboxylate (compound 14a, 551 mg, 0.78 mmol) in DMF (3 mL) was added to the reaction mixture, followed by sodium iodide (234 mg, 1.56 mmol). The resulting mixture was stirred at 80° C. for 16 h. After cooling to room temperature, the reaction mixture was diluted with water, extracted with EtOAc for three times. The combined organic layer was washed with brine, dried and concentrated to afford crude ethyl 6-tert-butyl-9-[6-[[4-(2-chloro-4-fluoro-phenyl)-5-ethoxycarbonyl-2-thiazol-2-yl-1,4-dihydropyrimidin-6-yl]methoxy]hexoxy]-10-methoxy-2-oxo-6,7-dihydrobenzo[a]quinolizine-3-carboxylate (compound 14b, 1.05 g) as a brown oil, which was directly used for next step without purification. MS obsd. (ESI$^+$) [(M+H)$^+$]: 849.

Step 3: Preparation of 6-tert-butyl-9-[6-[[4-(2-chloro-4-fluoro-phenyl)-5-ethoxycarbonyl-2-thiazol-2-yl-1,4-dihydropyrimidin-6-yl]methoxy]hexoxy]-10-methoxy-2-oxo-6,7-dihydrobenzo[a]quinolizine-3-carboxylic Acid (Example 14)

A mixture of crude ethyl 6-tert-butyl-9-[6-[[4-(2-chloro-4-fluoro-phenyl)-5-ethoxycarbonyl-2-thiazol-2-yl-1,4-dihydropyrimidin-6-yl]methoxy]hexoxy]-10-methoxy-2-oxo-6,7-dihydrobenzo[a]quinolizine-3-carboxylate (compound 14b, 1.05 g, 1.24 mmol), lithium hydroxide hydrate (415 mg, 9.89 mmol) in THF (6 mL) and H$_2$O (2 mL) was stirred at room temperature for 2 h. The reaction mixture was diluted with water, acidified by 1 M HCl to pH-3 and extracted with CH$_2$Cl$_2$ for three times. The combined organic layer was washed with brine, dried and concentrated. The residue was purified by preparative HPLC to afford 6-tert-butyl-9-[6-[[4-(2-chloro-4-fluoro-phenyl)-5-ethoxycarbonyl-2-thiazol-2-yl-1,4-dihydropyrimidin-6-yl]methoxy]hexoxy]-10-methoxy-2-oxo-6,7-dihydrobenzo[a]quinolizine-3-carboxylic acid (Example 14, 90 mg) as a yellow solid. MS obsd. (ESI$^+$) [(M+H)$^+$]: 821. $^1$H NMR (400 MHz, DMSO-d$_6$) δ=9.11 (s, 1H), 8.71 (s, 1H), 8.01-7.89 (m, 2H), 7.49-7.38 (m, 4H), 7.18 (dt, 1H), 7.01 (d, 1H), 6.03 (d, 1H), 4.88-4.72 (m, 2H), 4.55 (d, 1H), 4.11-3.91 (m, 4H), 3.86 (s, 3H), 3.68-3.55 (m, 2H), 3.40-3.33 (m, 1H), 3.26-3.15 (m, 1H), 1.84-1.24 (m, 6H), 1.04 (t, J=7.1 Hz, 3H), 0.71 (s, 9H)

Example 15
9-[6-[[3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoyl]amino]hexoxy]-6-tert-butyl-10-methoxy-2-oxo-6,7-dihydrobenzo[a]quinolizine-3-carboxylic Acid
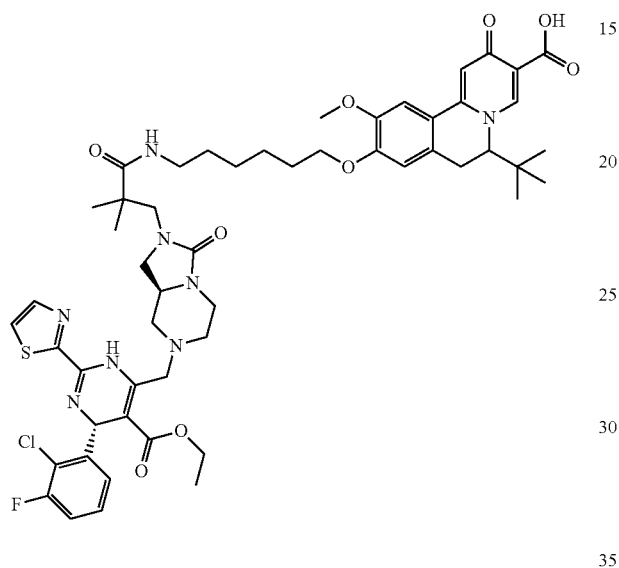
The title compound was prepared according to the following scheme:
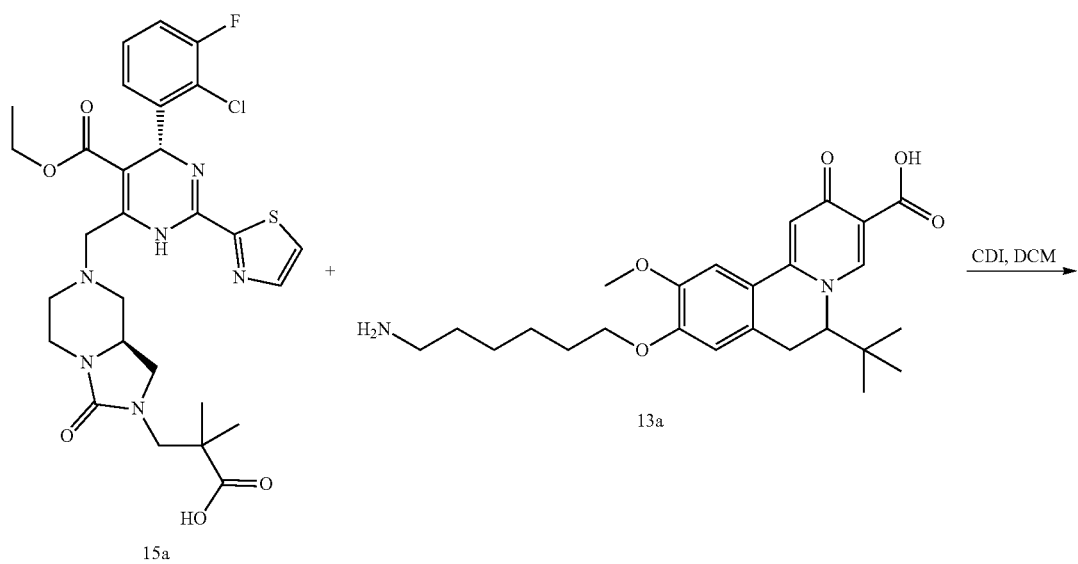

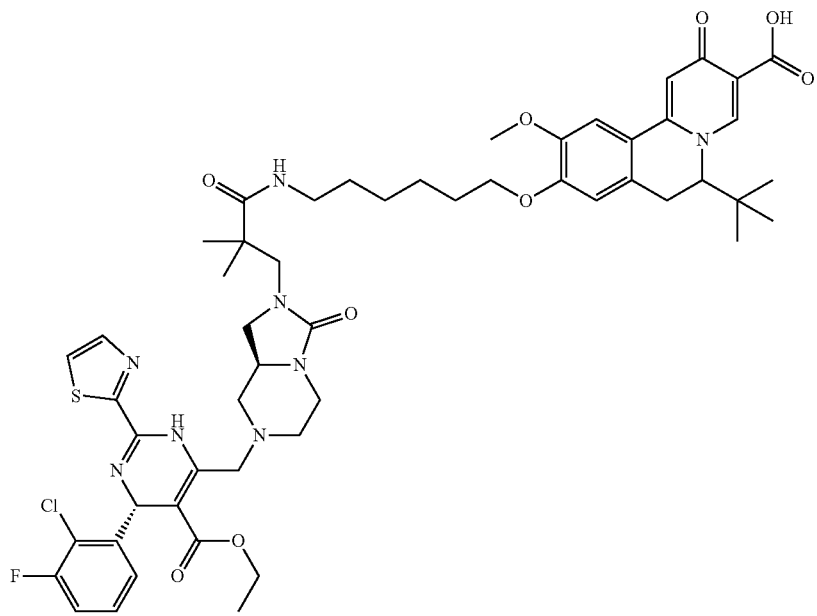

15

To a solution of 3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoic acid (compound 15a, 30 mg, 48.5 μmol, prepared according to the procedure in US20160083383, Example 19) in DCM (2 mL) was added CDI (9.43 mg, 58.1 μmol) at 0° C. The mixture was stirred for one hour, then triethylamine (14.7 mg, 20.3 μL, 145 μmol) and 9-((6-aminohexyl)oxy)-6-(tert-butyl)-10-methoxy-2-oxo-6,7-dihydro-2H-pyrido[2,1-a]isoquinoline-3-carboxylic acid hydrochloride (compound 13a, 23.2 mg, 48.5 μmol) was added. The reaction mixture was warmed to room temperature and stirred for 16 hours. The reaction mixture was concentrated under reduced pressure. The residue was purified by Preparative HPLC to give 9-[6-[[3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoyl]amino]hexoxy]-6-tert-butyl-10-methoxy-2-oxo-6,7-dihydrobenzo[a]quinolizine-3-carboxylic acid (Example 15, 17 mg). MS obsd. (ESI$^+$) [(M+H)$^+$]: 1043. $^1$H NMR (400 MHz, DMSO-$d_6$) δ=9.65 (s, 1H), 8.72 (s, 1H), 8.37 (s, 1H), 8.03 (d, 1H), 7.95 (d, 1H), 7.66-7.58 (m, 1H), 7.43-7.22 (m, 4H), 7.02 (s, 1H), 6.04 (s, 1H), 4.61-4.50 (m, 1H), 4.06-3.88 (m, 6H), 3.83 (s, 3H), 3.75-3.56 (m, 3H), 3.26-3.09 (m, 5H), 3.05-2.73 (m, 6H), 2.18-2.09 (m, 1H), 2.07-1.97 (m, 1H), 1.77-1.68 (m, 2H), 1.34-1.22 (m, 6H), 1.10-0.96 (m, 9H), 0.72 (s, 9H).

Example 16
9-[6-[[4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoyl]amino]hexoxy]-6-tert-butyl-10-methoxy-2-oxo-6,7-dihydrobenzo[a]quinolizine-3-carboxylic Acid
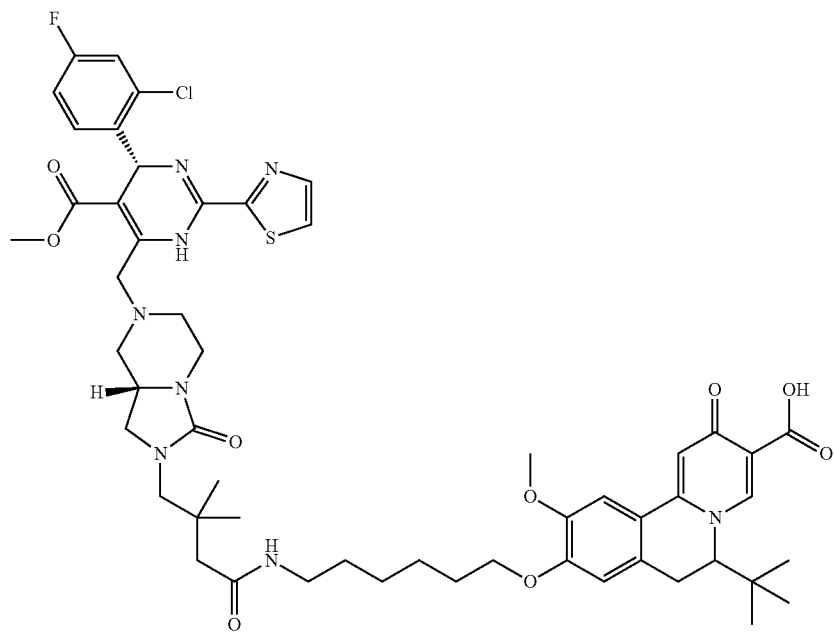
The title compound was prepared according to the following scheme:
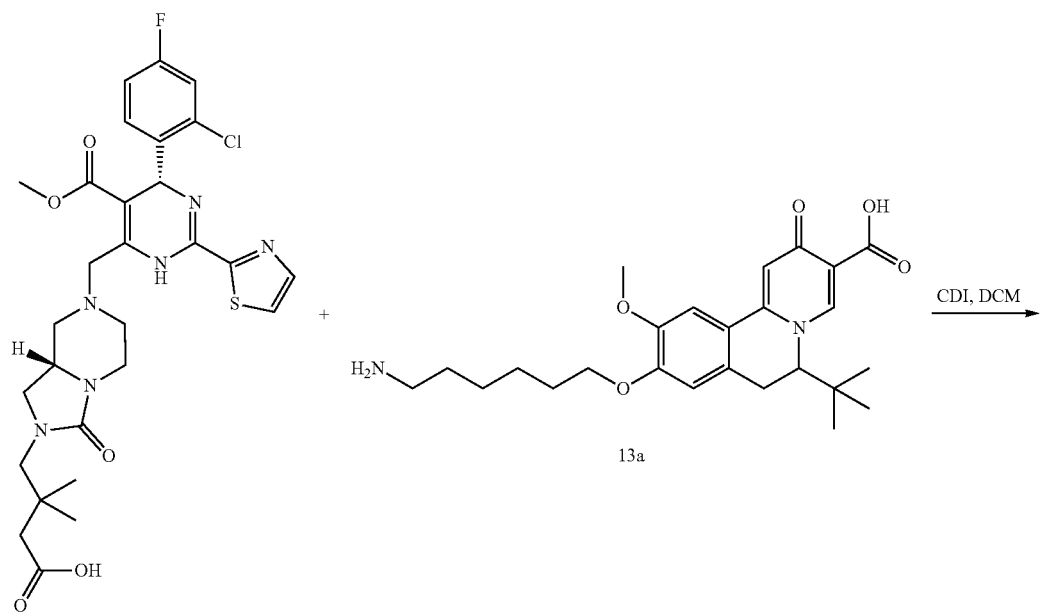

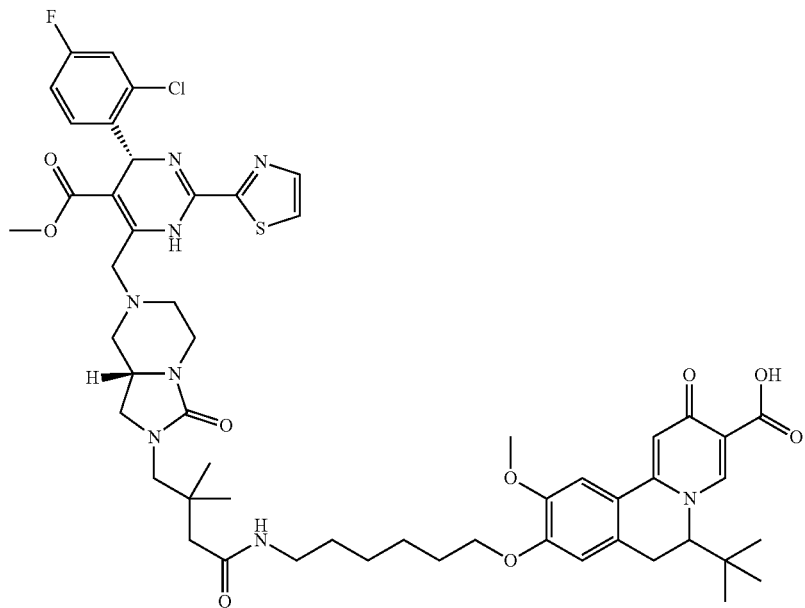 [SMILES: COC(=O)C1=C(CN2CCN3C(=O)N(CC(C)(C)CC(=O)NCCCCCCOc4cc5c(cc4OC)-c4cc(=O)c(C(=O)O)cn4C(C(C)(C)C)C5)C[C@@H]3C2)NC(c2nccs2)=N[C@H]1c1ccc(F)cc1Cl]

16

To a solution of 4-[(8aS)-7-[[(4R)-4-(2-chloro-4-fluorophenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid (compound 16a, 30 mg, 48.5 μmol, prepared according to the procedure in US20160083383, Example 55) in DCM (2 mL) was added CDI (9.43 mg, 58.1 μmol) at 0° C. The mixture was stirred for one hour, then triethylamine (14.7 mg, 20.3 μL, 145 μmol) and 9-((6-aminohexyl)oxy)-6-(tert-butyl)-10-methoxy-2-oxo-6,7-dihydro-2H-pyrido[2,1-a]isoquinoline-3-carboxylic acid hydrochloride (compound 13a, 23.2 mg, 48.5 μmol) was added to the solution. The mixture was warmed to room temperature and stirred for 16 hours. The reaction mixture was concentrated under reduced pressure. The residue was purified by Preparative HPLC to give 9-[6-[[4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoyl]amino]hexoxy]-6-tert-butyl-10-methoxy-2-oxo-6,7-dihydrobenzo[a]quinolizine-3-carboxylic acid (Example 16, 14 mg). MS obsd. (ESI$^+$) [(M+H)$^+$]: 1043. $^1$H NMR (400 MHz, DMSO-d$_6$) δ=9.71 (s, 1H), 8.72 (s, 1H), 8.03 (d, 1H), 7.96 (d, 2H), 7.48-7.37 (m, 4H), 7.23-7.13 (m, 1H), 7.05 (s, 1H), 6.04 (s, 1H), 4.61-4.52 (m, 1H), 4.08-3.98 (m, 3H), 3.95-3.88 (m, 2H), 3.86 (s, 3H), 3.76-3.68 (m, 1H), 3.69-3.62 (m, 1H), 3.52 (s, 3H), 3.53-3.50 (m, 1H), 3.46-3.36 (m, 2H), 3.28-3.22 (m, 1H), 3.11-2.94 (m, 4H), 2.90-2.78 (m, 3H), 2.24-2.13 (m, 1H), 2.13-2.05 (m, 1H), 2.01-1.93 (m, 2H), 1.79-1.70 (m, 2H), 1.46-1.20 (m, 6H), 0.91 (d, 6H), 0.73 (s, 9H).

Example 17
methyl (4R)-6-[[[(8aS)-2-[4-[6-[2,3-difluoro-5-[5-methyl-2-pyrimidin-2-yl-7,8-dihydro-5H-pyrido[4,3-d]pyrimidin-6-yl]phenoxy]hexylamino]-2,2-dimethyl-4-oxo-butyl]-3-oxo-5,6,8,8a-tetrahydro-1H-imidazo[1,5-a]pyrazin-7-yl]methyl]-4-(2-chloro-4-fluoro-phenyl)-2-thiazol-2-yl-1,4-dihydropyrimidine-5-carboxylate
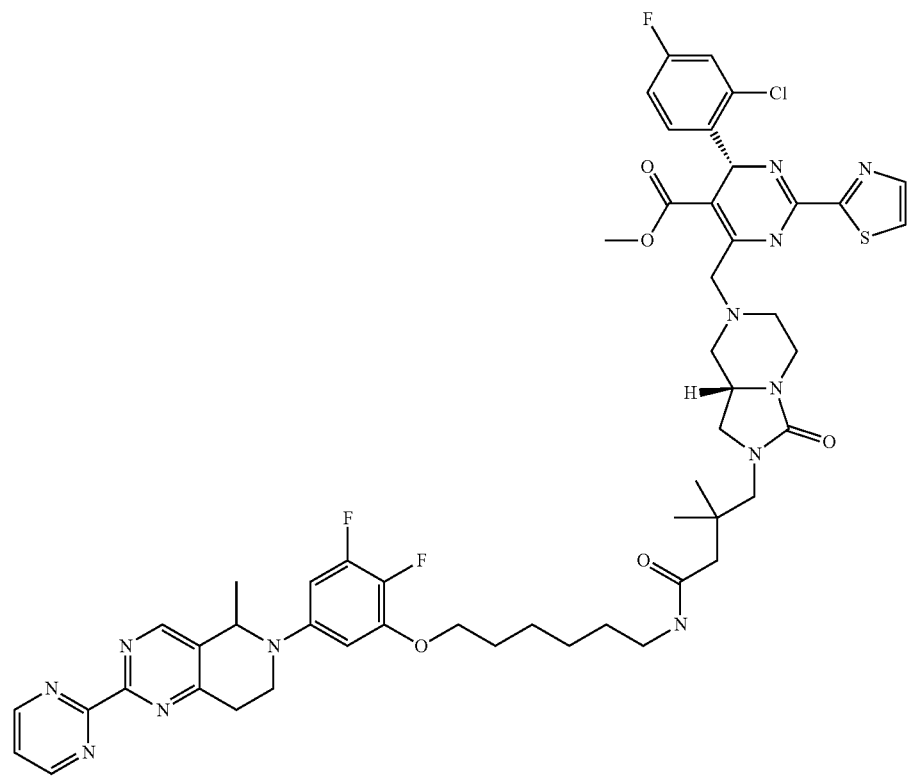

The title compound was prepared according to the following scheme:

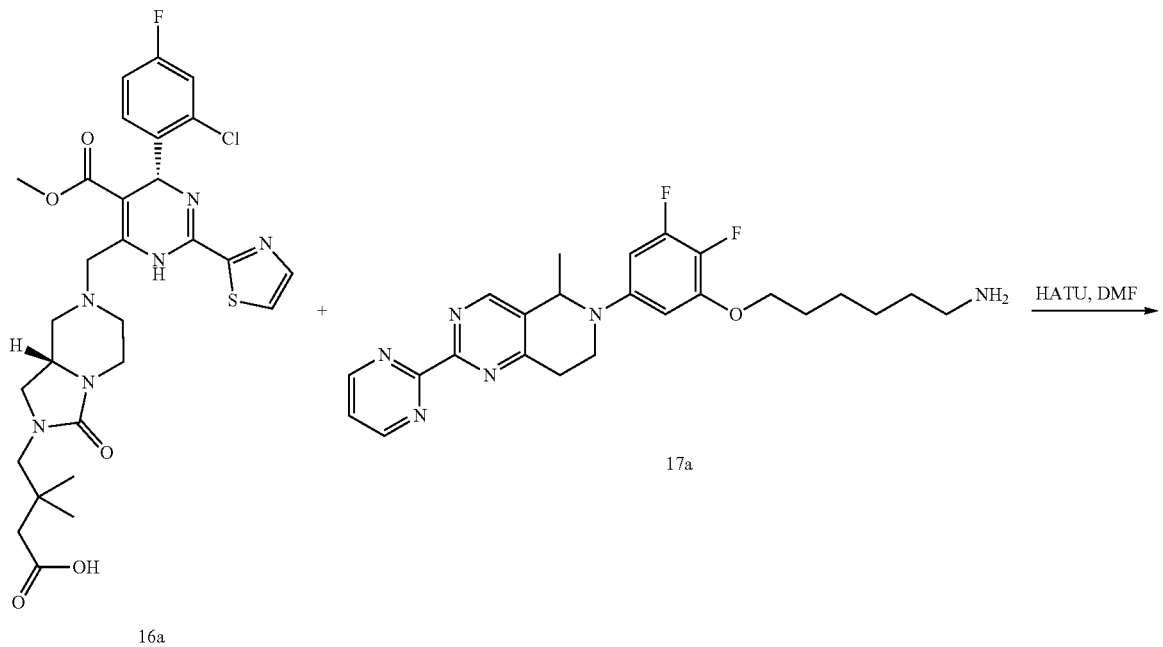

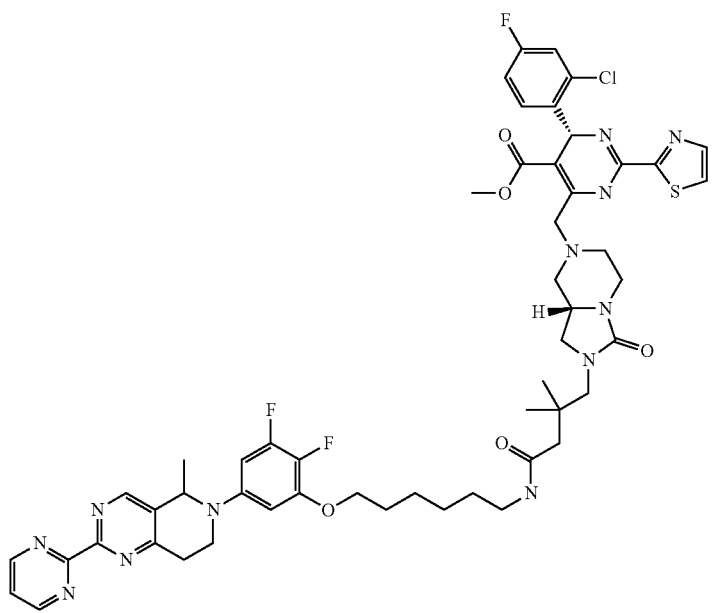

To a solution of 4-[(8aS)-7-[[(4R)-4-(2-chloro-4-fluorophenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoic acid (compound 16a, 60 mg, 96.9 μmol) in DMF (3 mL) was added triethylamine (19.6 mg, 27 μL, 194 μmol) and HATU (55.3 mg, 145 μmol). The mixture was stirred for ten minutes at room temperature, then 6-(2,3-difluoro-5-(5-methyl-2-(pyrimidin-2-yl)-7,8-dihydropyrido[4,3-d]pyrimidin-6(5H)-yl)phenoxy)hexan-1-amine (compound 17a, 44 mg, 96.9 μmol, prepared according to WO2016177655, Example 59) was added. The mixture was stirred for 14 hours at room temperature, and then purified by Preparative HPLC to give methyl (4R)-6-[[(8aS)-2-[4-[6-[2,3-difluoro-5-[5-methyl-2-pyrimidin-2-yl-7,8-dihydro-5H-pyrido[4,3-d]pyrimidin-6-yl]phenoxy]hexylamino]-2,2-dimethyl-4-oxo-butyl]-3-oxo-5,6,8,8a-tetrahydro-1H-imidazo[1,5-a]pyrazin-7-yl]methyl]-4-(2-chloro-4-fluoro-phenyl)-2-thiazol-2-yl-1,4-dihydropyrimidine-5-carboxylate (Example 17, 70 mg). MS obsd. (ESI$^+$) [(M+H)$^+$]: 1055. $^1$H NMR (400 MHz, DMSO-d$_6$) δ=9.70 (s, 1H), 8.99 (d, 2H), 8.84 (s, 1H), 8.02 (d, 1H), 7.95-7.94 (m, 2H), 7.63 (t, 1H), 7.46-7.37 (m, 2H), 7.21-7.11 (m, 1H), 6.65-6.57 (m, 2H), 6.03 (s, 1H), 5.33-5.23 (m, 1H), 4.09 (t, 2H), 3.98-3.86 (m, 3H), 3.73-3.67 (m, 1H), 3.67-3.61 (m, 1H), 3.51 (s, 3H), 3.48-3.40 (m, 3H), 3.3 (s, 2H), 3.15-2.94 (m, 5H), 2.89-2.78 (m, 4H), 2.23-2.15 (m, 1H), 2.12-2.04 (m, 1H), 2.01-1.90 (m, 2H), 1.78-1.69 (m, 2H), 1.47-1.29 (m, 7H), 0.90 (d, 6H).

Example 18
methyl (4R)-4-(2-chloro-4-fluoro-phenyl)-6-[[(3S)-3-[6-[2,3-difluoro-5-(5-methyl-2-pyrimidin-2-yl-7,8-dihydro-5H-pyrido[4,3-d]pyrimidin-6-yl)phenoxy]hexylcarbamoyl]morpholin-4-yl]methyl]-2-thiazol-2-yl-1,4-dihydropyrimidine-5-carboxylate
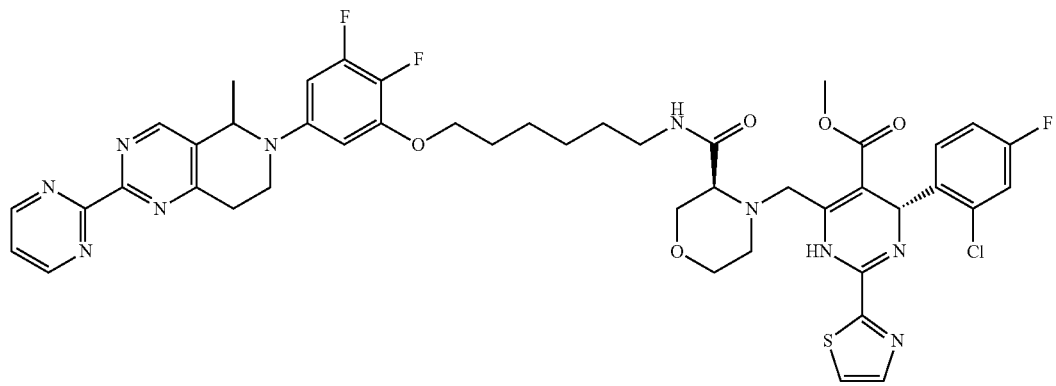 [SMILES: COC(=O)C1=C(CN2CCOC[C@H]2C(=O)NCCCCCCOc2cc(N3CCc4nc(-c5ncccn5)ncc4C3C)cc(F)c2F)NC(c2nccs2)=N[C@H]1c1ccc(F)cc1Cl]
The title compound was prepared according to the following scheme:
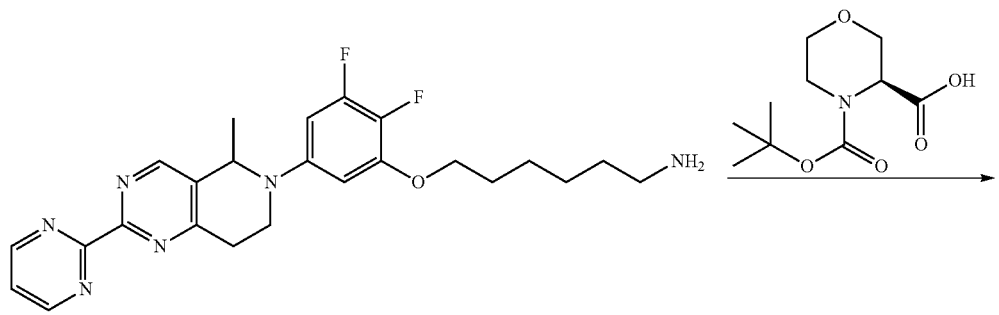
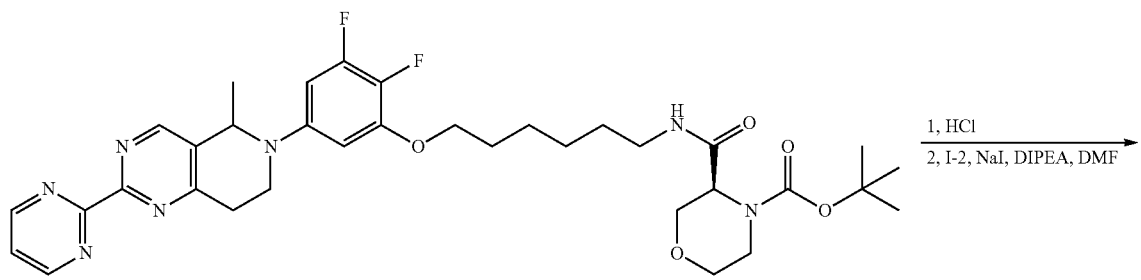

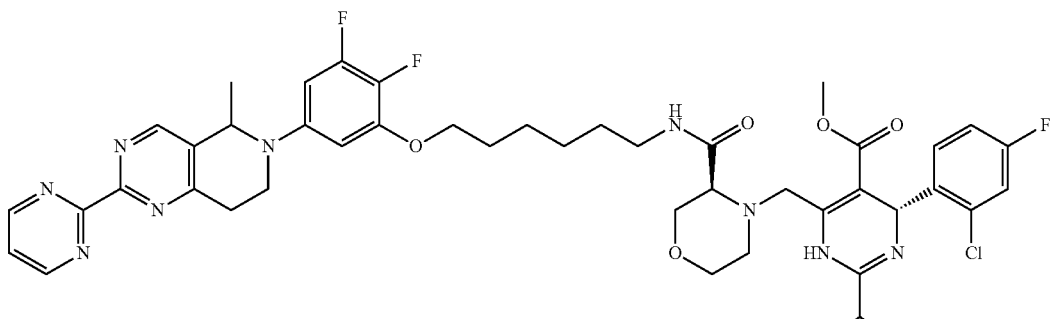

18

The title compound was prepared in analogy to the preparation of Example 13 by using compound 17a instead of compound 13a. Example 18 (115 mg) was obtained as a solid. MS obsd. (ESI⁺) [(M+H)⁺]: 931. ¹H NMR (400 MHz, DMSO-d₆) δ=9.96 (s, 1H), 8.99 (d, 2H), 8.83 (d, 1H), 8.17-8.09 (m, 1H), 8.02 (d, 1H), 7.91 (d, 1H), 7.64 (t, 1H), 7.44-7.34 (m, 2H), 7.20-7.12 (m, 1H), 6.65-6.57 (m, 2H), 5.99 (s, 1H), 5.33-5.25 (m, 1H), 4.07 (t, 2H), 4.03-3.68 (m, 5H), 3.61-3.52 (m, 2H), 3.48 (s, 3H), 3.45-3.39 (m, 1H), 3.27-3.24 (m, 1H), 3.16-3.01 (m, 2H), 3.01-2.92 (m, 2H), 1.76-1.66 (m, 2H), 1.45-1.24 (m, 11H).

Example 19 methyl (4R)-4-(2-chloro-4-fluoro-phenyl)-6-[[(3R)-3-[[6-[2,3-difluoro-5-(5-methyl-2-pyrimidin-2-yl-7,8-dihydro-5H-pyrido[4,3-d]pyrimidin-6-yl)phenoxy]hexyl-methyl-amino]methyl]morpholin-4-yl]methyl]-2-thiazol-2-yl-1,4-dihydropyrimidine-5-carboxylate

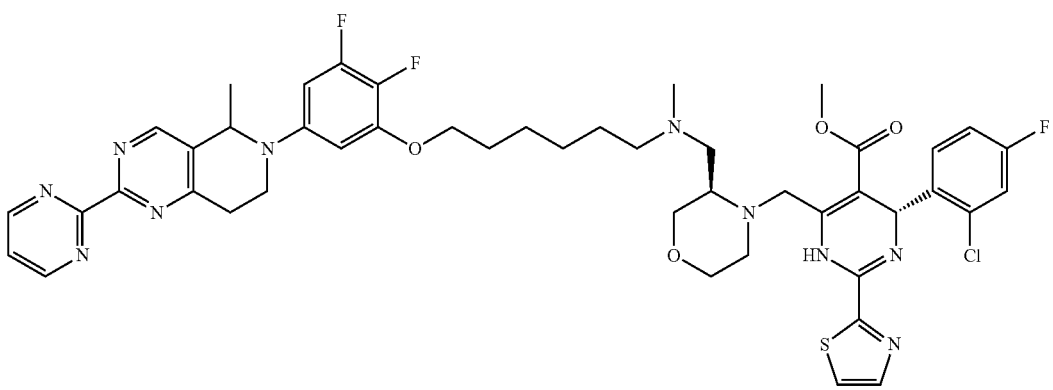

The title compound was prepared according to the following scheme:

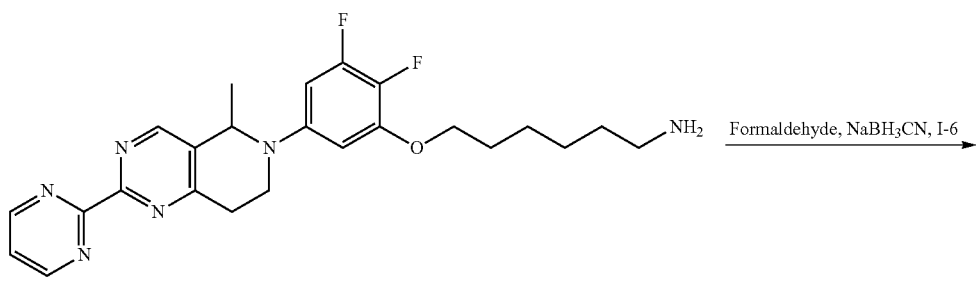

17a

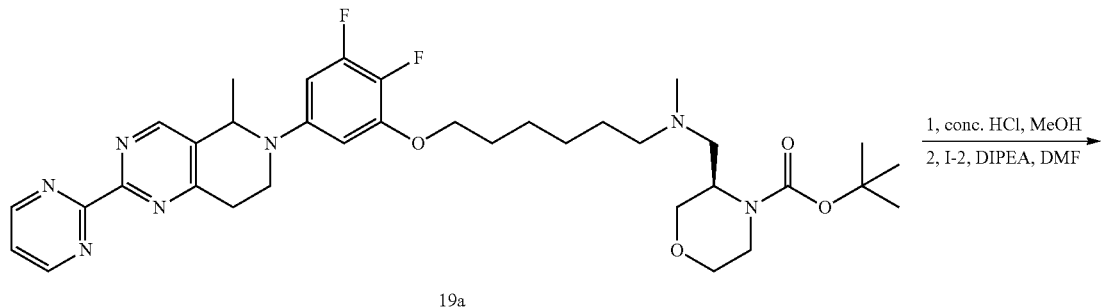

19a

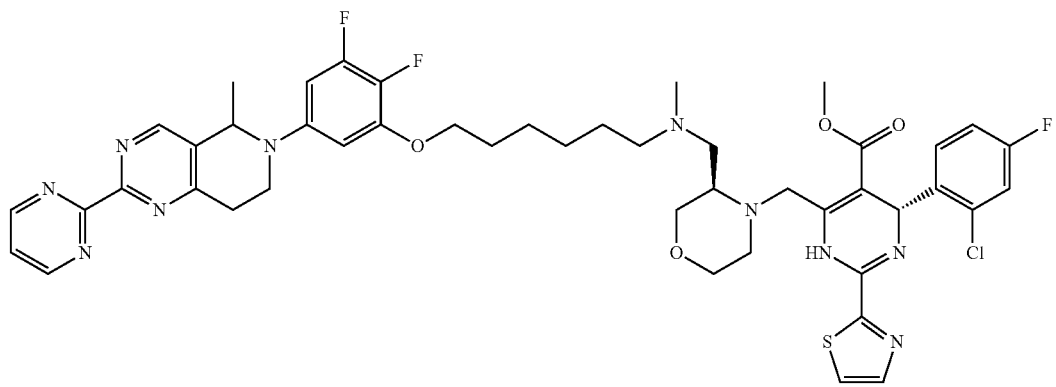 [SMILES: COC(=O)C1=C(CN2CCOC[C@H]2CN(C)CCCCCCOc2cc(N3CCc4nc(-c5ncccn5)ncc4C3C)cc(F)c2F)NC(c2nccs2)=N[C@H]1c1ccc(F)cc1Cl]

19

Step 1: Preparation of tert-butyl (3R)-3-[[6-[2,3-difluoro-5-(5-methyl-2-pyrimidin-2-yl-7,8-dihydro-5H-pyrido[4,3-d]pyrimidin-6-yl)phenoxy]hexyl-methyl-amino]methyl]morpholine-4-carboxylate To a solution of 6-(2,3-difluoro-5-(5-methyl-2-(pyrimidin-2-yl)-7,8-dihydropyrido[4,3-d]pyrimidin-6(5H)-yl)phenoxy)hexan-1-amine (compound 17a, 300 mg, 660 μmol) in MeOH (5 mL) was added formaldehyde (19.8 mg, 660 μmol). The mixture was stirred for 5 hours at room temperature, then sodium cyanoborohydride (124 mg, 1.98 mmol) was added. The mixture was stirred for at room temperature 12 hours, then crude (S)-tert-butyl 3-formylmorpholine-4-carboxylate (intermediate I-6, 284 mg) was added. The resulting mixture was stirred for another 12 hours, then quenched with aqueous 2 M NaOH solution. The mixture was diluted with water and extracted with DCM. The organic layer was concentrated to give compound 19a (470 mg), which was directly used for the next step without further purification.

Step 2: Preparation of methyl (4R)-4-(2-chloro-4-fluoro-phenyl)-6-[[(3R)-3-[[6-[2,3-difluoro-5-(5-methyl-2-pyrimidin-2-yl-7,8-dihydro-5H-pyrido[4,3-d]pyrimidin-6-yl)phenoxy]hexyl-methyl-amino]methyl]morpholin-4-yl]methyl]-2-thiazol-2-yl-1,4-dihydropyrimidine-5-carboxylate To a solution of tert-butyl (3R)-3-[[6-[2,3-difluoro-5-(5-methyl-2-pyrimidin-2-yl-7,8-dihydro-5H-pyrido[4,3-d]pyrimidin-6-yl)phenoxy]hexyl-methyl-amino]methyl]morpholine-4-carboxylate (compound 19a, 470 mg) in MeOH (5 mL) was added concentrated hydrochloride (3 mL). The mixture was stirred at room temperature for 5 hours and then basified with aqueous $NaHCO_3$. The resulting mixture was extracted with DCM. The organic layer was dried over anhydrous $Na_2SO_4$ and concentrated. The residue was dissolved in DMF (3 mL), followed by addition of DIPEA (45.5 mg, 61.5 μL), potassium iodide (29.2 mg, 176 μmol) and (R)-methyl 6-(bromomethyl)-4-(2-chloro-4-fluorophenyl)-2-(thiazol-2-yl)-1,4-dihydropyrimidine-5-carboxylate (intermediate I-2, 150 mg). The mixture was stirred at 50° C.

for 3 hours, and then purified by Preparative HPLC to give methyl (4R)-4-(2-chloro-4-fluoro-phenyl)-6-[[(3R)-3-[[6-[2,3-difluoro-5-(5-methyl-2-pyrimidin-2-yl-7,8-dihydro-5H-pyrido[4,3-d]pyrimidin-6-yl)phenoxy]hexyl-methyl-amino]methyl]morpholin-4-yl]methyl]-2-thiazol-2-yl-1,4-dihydropyrimidine-5-carboxylate (Example 19, 37 mg). MS obsd. (ESI+) [(M+H)+]: 931. ¹H NMR (400 MHz, DMSO-d6) δ=8.99 (d, 2H), 8.83 (s, 1H), 8.07 (s, 1H), 8.02 (t, 1H), 7.97-7.92 (m, 1H), 7.64 (t, 1H), 7.45-7.36 (m, 2H), 7.17-7.12 (m, 1H), 6.67-6.57 (m, 2H), 6.04 (s, 1H), 5.35-5.26 (m, 1H), 4.15-4.01 (m, 3H), 3.95-3.60 (m, 5H), 3.52 (s, 3H), 3.49-3.40 (m, 2H), 3.22-2.93 (m, 5H), 2.92-2.77 (m, 2H), 2.54 (s, 3H), 1.83-1.60 (m, 4H), 1.58-1.16 (m, 9H).

Example 20 methyl (4R)-4-(2-chloro-4-fluoro-phenyl)-6-[[2,3-difluoro-5-(5-methyl-2-pyrimidin-2-yl-7,8-dihydro-5H-pyrido[4,3-d]pyrimidin-6-yl)phenoxy]methyl]-2-thiazol-2-yl-1,4-dihydropyrimidine-5-carboxylate

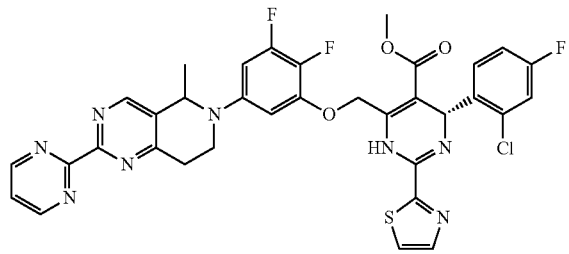 [SMILES: COC(=O)C1=C(COc2cc(N3CCc4nc(-c5ncccn5)ncc4C3C)cc(F)c2F)NC(c2nccs2)=N[C@H]1c1ccc(F)cc1Cl]

The title compound was prepared according to the following scheme:

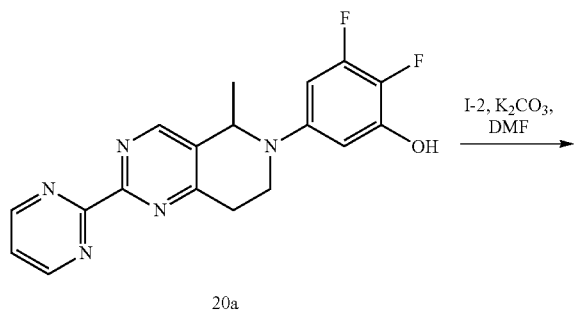

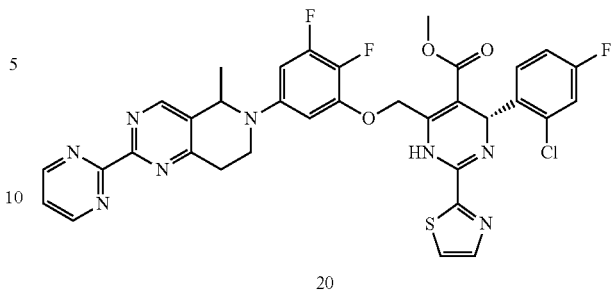

To a solution of 2,3-difluoro-5-(5-methyl-2-(pyrimidin-2-yl)-7,8-dihydropyrido[4,3-d]pyrimidin-6(5H)-yl)phenol (compound 20a, 24 mg, 67.5 µmol, prepared according to WO2016177655, example 44) in DMF was added potassium carbonate (18.7 mg, 135 µmol). The mixture was stirred at 80° C. for one hour. Then the mixture was cooled to room temperature and (R)-methyl 6-(bromomethyl)-4-(2-chloro-4-fluorophenyl)-2-(thiazol-2-yl)-1,4-dihydropyrimidine-5-carboxylate (30 mg, 67.5 µmol) was added. The mixture was stirred at 55° C. for two hours. The mixture was cooled to room temperature and filtered. The filtrate was purified by Preparative HPLC to give methyl (4R)-4-(2-chloro-4-fluoro-phenyl)-6-[[2,3-difluoro-5-(5-methyl-2-pyrimidin-2-yl-7,8-dihydro-5H-pyrido[4,3-d]pyrimidin-6-yl)phenoxy]methyl]-2-thiazol-2-yl-1,4-dihydropyrimidine-5-carboxylate (Example 20, 32 mg). MS obsd. (ESI+) [(M+H)+]: 719. ¹H NMR (400 MHz, DMSO-d6) δ=9.81 (s, 1H), 8.99 (d, 2H), 8.72 (s, 1H), 7.96-7.79 (m, 2H), 7.64 (t, 1H), 7.33 (dd, 2H), 7.00 (s, 1H), 6.80 (s, 1H), 6.75-6.56 (m, 1H), 6.00 (s, 1H), 5.50-5.25 (m, 2H), 5.23-5.12 (m, 1H), 3.92-3.78 (m, 1H), 3.53 (s, 3H), 3.47-3.37 (m, 1H), 3.13-2.96 (m, 2H), 1.34 (d, 3H).

Example 21

(2R)-4-[4-[[[(4R)-4-(2-chloro-4-fluoro-phenyl)-5-methoxycarbonyl-2-thiazol-2-yl-1,4-dihydropyrimidin-6-yl]methyl]piperazin-1-yl]-2-[6-[2,3-difluoro-5-(5-methyl-2-pyrimidin-2-yl-7,8-dihydro-5H-pyrido[4,3-d]pyrimidin-6-yl)phenoxy]hexylamino]butanoic Acid

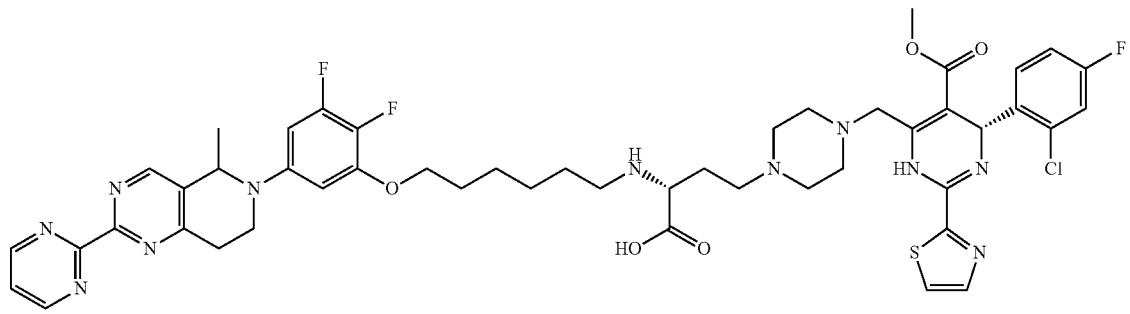 [SMILES: COC(=O)C1=C(CN2CCN(CC[C@@H](NCCCCCCOc3cc(N4CCc5nc(-c6ncccn6)ncc5C4C)cc(F)c3F)C(=O)O)CC2)NC(c2nccs2)=N[C@H]1c1ccc(F)cc1Cl]

The title compound was prepared according to the following scheme:
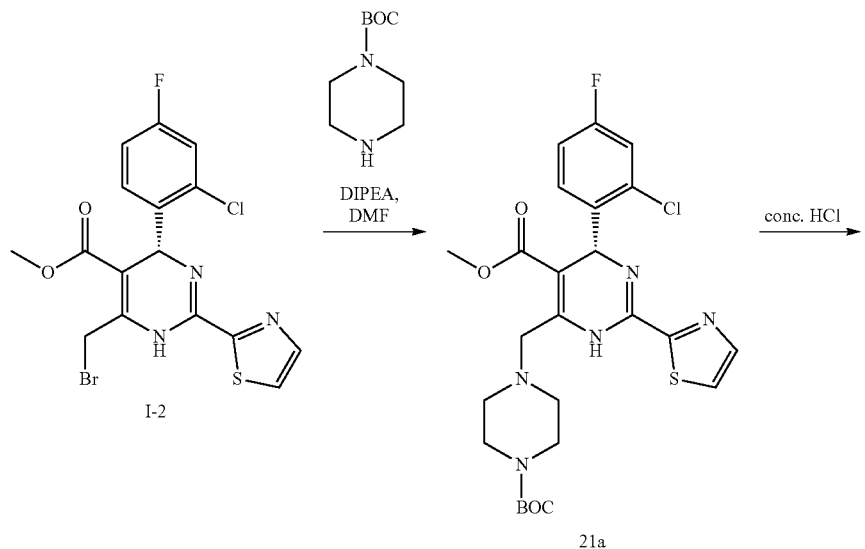
21a
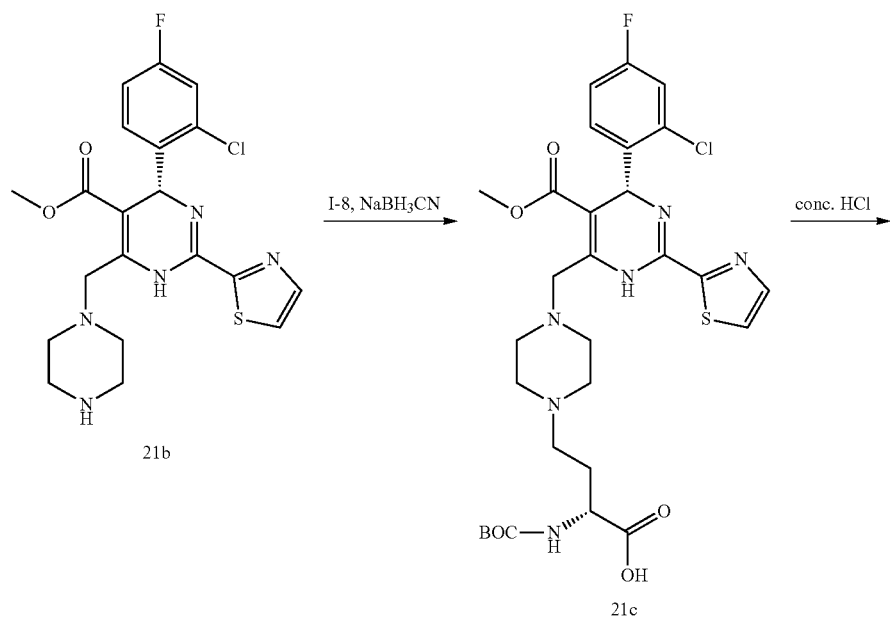

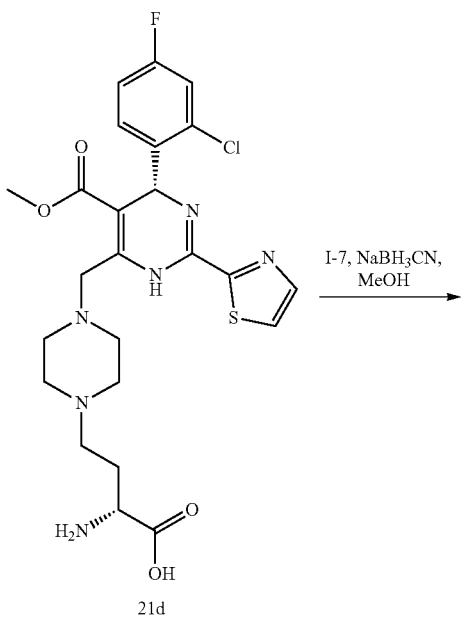

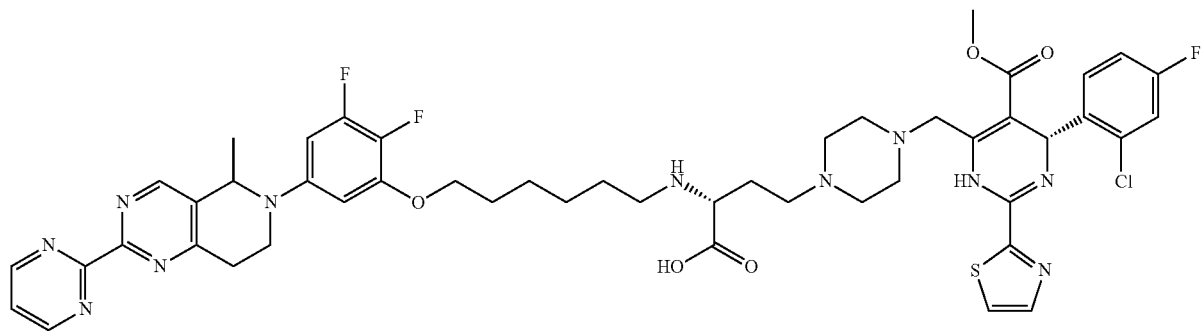

21

Step 1: Preparation of methyl (4R)-6-[(4-tert-butoxycarbonylpiperazin-1-yl)methyl]-4-(2-chloro-4-fluoro-phenyl)-2-thiazol-2-yl-1,4-dihydropyrimidine-5-carboxylate (Compound 21a)

To a solution of (R)-methyl 6-(bromomethyl)-4-(2-chloro-4-fluorophenyl)-2-(thiazol-2-yl)-1,4-dihydropyrimidine-5-carboxylate (intermediate I-2, 100 mg, 225 μmol) in DMF (1 mL) was added tert-butyl piperazine-1-carboxylate (41.9 mg, 225 μmol), DIPEA (78.5 μl, 450 μmol) and potassium iodide (74.7 mg, 450 μmol). The mixture was stirred at 50° C. for 3 hours, and then cooled to room temperature and concentrated under reduced pressure. The residue was purified by column chromatography to give compound 21a (97 mg).

Step 2: Preparation of methyl (4R)-4-(2-chloro-4-fluoro-phenyl)-6-(piperazin-1-ylmethyl)-2-thiazol-2-yl-1,4-dihydropyrimidine-5-carboxylate (Compound 21b)

To a solution of methyl (4R)-6-[(4-tert-butoxycarbonylpiperazin-1-yl)methyl]-4-(2-chloro-4-fluoro-phenyl)-2-thiazol-2-yl-1,4-dihydropyrimidine-5-carboxylate (compound 21a, 97 mg, 176 μmol) in MeOH (5 mL) was added concentrated hydrochloride (2 mL). The mixture was stirred at room temperature for one hour, and then basified with saturated aqueous sodium bicarbonate. The mixture was extracted with DCM. The organic layer was dried over anhydrous $Na_2SO_4$ and concentrated to give methyl (4R)-4-(2-chloro-4-fluoro-phenyl)-6-(piperazin-1-ylmethyl)-2-thiazol-2-yl-1,4-dihydropyrimidine-5-carboxylate (compound 21b, 75 mg).

Step 3: Preparation of (2R)-2-(tert-butoxycarbonylamino)-4-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]butanoic Acid (Compound 21c)

To a solution of methyl (4R)-6-[(4-tert-butoxycarbonylpiperazin-1-yl)methyl]-4-(2-chloro-4-fluoro-phenyl)-2-thiazol-2-yl-1,4-dihydropyrimidine-5-carboxylate (compound 21b, 80 mg, 178 μmol) in MeOH (5 mL) was added crude (2R)-2-(tert-butoxycarbonylamino)-4-oxo-butanoic acid (intermediate I-8, 129 mg). The mixture was stirred at room temperature for two hours, then sodium cyanoborohydride (22.3 mg, 356 μmol) was added. The resulting mixture was stirred at room temperature for 16 hours, then partitioned between aqueous K₂CO₃ solution and DCM. The organic layer was concentrated under reduced pressure. The residue was purified by column chromatography to give (2R)-2-(tert-butoxycarbonylamino)-4-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]butanoic acid (compound 21c, 128 mg).

Step 4: Preparation of (2R)-2-amino-4-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]butanoic acid (compound 21d)

To a solution of (2R)-2-(tert-butoxycarbonylamino)-4-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]butanoic acid (compound 21c, 128 mg, 197 μmol) in MeOH (5 mL) was added concentrated hydrochloride (2 mL). The mixture was stirred at room temperature for 5 hours, then basified with aqueous ammonia and extracted with DCM. The organic layer was concentrated under reduced pressure to give (2R)-2-amino-4-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]butanoic acid (compound 21d, 112 mg).

Step 5: Preparation of (2R)-4-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]-2-[6-[2,3-difluoro-5-(5-methyl-2-pyrimidin-2-yl-7,8-dihydro-5H-pyrido[4,3-d]pyrimidin-6-yl)phenoxy]hexylamino]butanoic Acid (Example 21)

To a solution of (2R)-2-amino-4-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]butanoic acid (compound 21d, 80 mg, 116 μmol) in MeOH (5 mL) was added crude 6-[2,3-difluoro-5-(5-methyl-2-pyrimidin-2-yl-7,8-dihydro-5H-pyrido[4,3-d]pyrimidin-6-yl)phenoxy]hexanal (intermediate I-7, 55 mg). The mixture was stirred at room temperature for 6 hours, then sodium cyanoborohydride (14.6 mg, 232 μmol) was added. The resulting mixture was stirred at room temperature for 15 hours, then purified by Preparative HPLC to give (2R)-4-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]-2-[6-[2,3-difluoro-5-(5-methyl-2-pyrimidin-2-yl-7,8-dihydro-5H-pyrido[4,3-d]pyrimidin-6-yl)phenoxy]hexylamino]butanoic acid (Example 21, 4.5 mg). MS obsd. (ESI⁺) [(M+H)⁺]: 988. ¹H NMR (400 MHz, DMSO-d₆) δ=9.66 (s, 1H), 8.99 (d, 2H), 8.84 (s, 1H), 8.01 (s, 1H), 7.94 (s, 1H), 7.63 (m, 1H), 7.43-7.34 (m, 2H), 7.23-7.12 (m, 1H), 6.61 (d, 2H), 6.02 (s, 1H), 5.35-5.25 (m, 1H), 4.14-4.05 (m, 2H), 3.98-3.78 (m, 3H), 3.49 (s, 3H), 3.14-2.73 (m, 7H), 2.63-2.52 (m, 8H), 1.96-1.52 (m, 8H), 1.50-1.16 (m, 7H).

Example 22

4-[[(4R)-4-(2-chloro-4-fluoro-phenyl)-5-methoxycarbonyl-2-thiazol-2-yl-1,4-dihydropyrimidin-6-yl]methyl]-1-[4-fluoro-6-[5-methyl-2-pyrimidin-2-yl-7,8-dihydro-5H-pyrido[4,3-d]pyrimidin-6-yl]-2-pyridyl]piperazine-2-carboxylic Acid

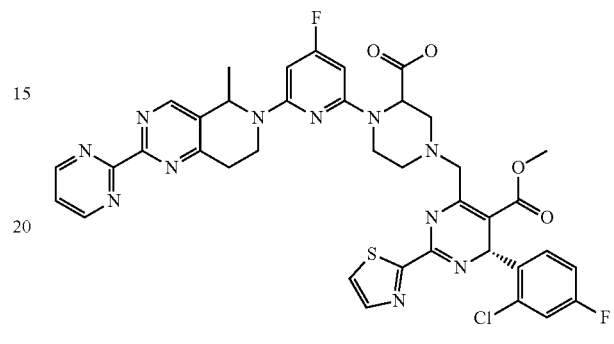

The title compound was prepared according to the following scheme:

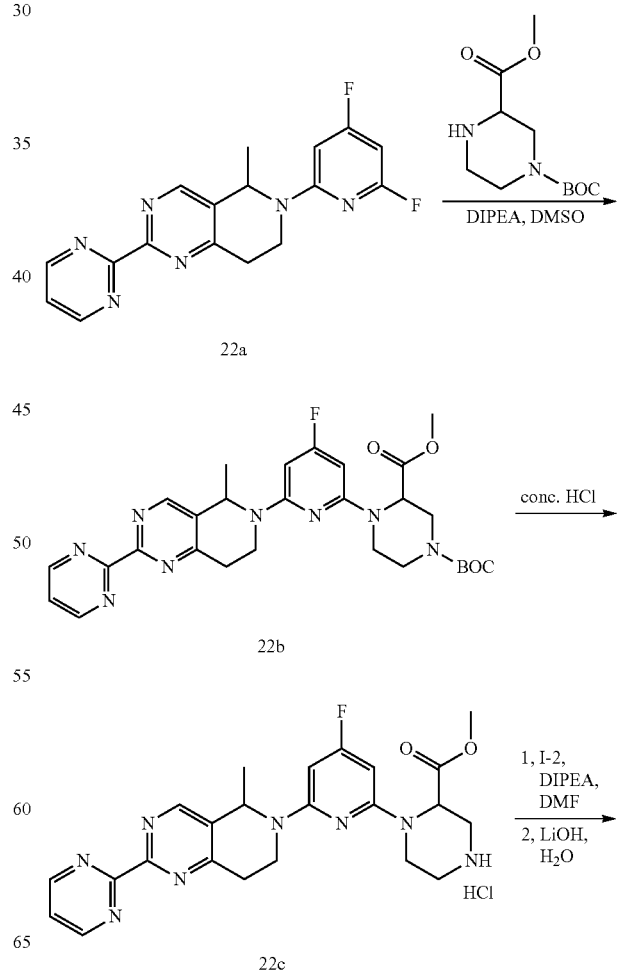

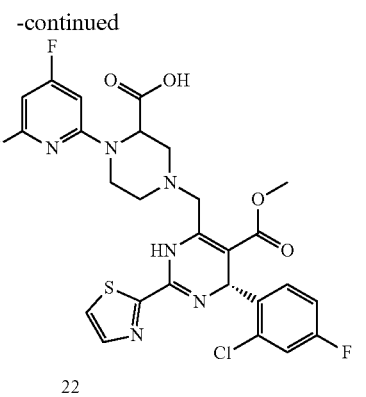

22

Step 1: Preparation of O1-tert-butyl O3-methyl 4-[4-fluoro-6-[5-methyl-2-pyrimidin-2-yl-7,8-dihydro-5H-pyrido[4,3-d]pyrimidin-6-yl]-2-pyridyl]piperazine-1,3-dicarboxylate (Compound 22b)

To a solution of 6-(4,6-difluoro-2-pyridyl)-5-methyl-2-pyrimidin-2-yl-7,8-dihydro-5H-pyrido[4,3-d]pyrimidine (compound 22a, 60 mg, 176 μmol, prepared according to WO2016177655, example 151) in DIPEA (2 mL) and DMSO (0.5 mL) was added O1-tert-butyl O3-methyl piperazine-1,3-dicarboxylate (56 mg, 229 μmol). The mixture was stirred at 120° C. for 48 hours, then concentrated under reduced pressure. The residue was purified by column chromatography to give O1-tert-butyl O3-methyl 4-[4-fluoro-6-[5-methyl-2-pyrimidin-2-yl-7,8-dihydro-5H-pyrido[4,3-d]pyrimidin-6-yl]-2-pyridyl]piperazine-1,3-dicarboxylate (compound 22b, 15 mg).

Step 2: Preparation of methyl 1-[4-fluoro-6-[5-methyl-2-pyrimidin-2-yl-7,8-dihydro-5H-pyrido[4,3-d]pyrimidin-6-yl]-2-pyridyl]piperazine-2-carboxylate Hydrochloride (Compound 22c)

To a solution of the mixture of O1-tert-butyl O3-methyl 4-[4-fluoro-6-[5-methyl-2-pyrimidin-2-yl-7,8-dihydro-5H-pyrido[4,3-d]pyrimidin-6-yl]-2-pyridyl]piperazine-1,3-dicarboxylate (compound 22b, 15 mg) in MeOH (5 mL) was added concentrated hydrochloride (1 m). The mixture was stirred at room temperature for two hours, then concentrated under reduced pressure to give crude methyl 1-[4-fluoro-6-[5-methyl-2-pyrimidin-2-yl-7,8-dihydro-5H-pyrido[4,3-d]pyrimidin-6-yl]-2-pyridyl]piperazine-2-carboxylate hydrochloride (compound 22c, 16.2 mg).

Step 3: Preparation of 4-[[(4R)-4-(2-chloro-4-fluoro-phenyl)-5-methoxycarbonyl-2-thiazol-2-yl-1,4-dihydropyrimidin-6-yl]methyl]-1-[4-fluoro-6-[5-methyl-2-pyrimidin-2-yl-7,8-dihydro-5H-pyrido[4,3-d]pyrimidin-6-yl]-2-pyridyl]piperazine-2-carboxylic Acid To a solution of methyl 1-[4-fluoro-6-[5-methyl-2-pyrimidin-2-yl-7,8-dihydro-5H-pyrido[4,3-d]pyrimidin-6-yl]-2-pyridyl]piperazine-2-carboxylate hydrochloride (compound 22c, 16.2 mg, 32.3 μmol in DMF (3 mL) was added (R)-methyl 6-(bromomethyl)-4-(2-chloro-4-fluorophenyl)-2-(thiazol-2-yl)-1,4-dihydropyrimidine-5-carboxylate (intermediate I-2, 14.4 mg, 32.3 μmol), DIPEA (12.5 mg, 96.9 μmol) and potassium iodide (10.7 mg, 64.6 μmol). The mixture was stirred at 50° C. for 3 hours, then cooled to room temperature. To the mixture was added water (1 mL) and lithium hydroxide monohydrate (15 mg). The resulting mixture was stirred at room temperature for two hours, then acidified with 6 M HCl and purified by Preparative HPLC to give 4-[[(4R)-4-(2-chloro-4-fluoro-phenyl)-5-methoxycarbonyl-2-thiazol-2-yl-1,4-dihydropyrimidin-6-yl]methyl]-1-[4-fluoro-6-[5-methyl-2-pyrimidin-2-yl-7,8-dihydro-5H-pyrido[4,3-d]pyrimidin-6-yl]-2-pyridyl]piperazine-2-carboxylic acid (Example 22, 5 mg). MS obsd. (ESI$^+$) [(M+H)$^+$]: 814. $^1$H NMR (400 MHz, DMSO-$d_6$) δ=8.99 (d, 2H), 8.91 (s, 1H), 7.99 (d, 1H), 7.92 (d, 1H), 7.63 (t, 1H), 7.46-7.38 (m, 2H), 7.22-7.14 (m, 2H), 6.14 (s, 1H), 6.04 (s, 1H), 5.89 (s, 1H), 5.73-5.66 (m, 1H), 4.50-4.40 (m, 1H), 4.16-4.10 (m, 1H), 3.51 (s, 3H), 3.47-3.36 (m, 3H), 3.32-3.28 (m, 2H), 3.17-2.89 (m, 6H), 1.50 (d, 3H).

BIOLOGICAL EXAMPLES

Example 23: HepG2.2.15 Cells Primary Screen Assay

Materials and Methods

HBV Cell Line

HepG2.2.15 cells (Acs et al. *Proc Natl Acad Sci USA*, 84, (1987), 4641-4), a constitutively HBV-expressing cell line were cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% $CO_2$ at 37° C.

HBsAg Assay

HepG2.2.15 cells were seeded in duplicate into white, 96-well plates at $1.5 \times 10^4$ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL0310-2) was used to measure the levels of secreted HBV antigens semi-quantitatively. For the detection 50 μL/well culture supernatant was used and HBsAg was quantified using HBsAg chemiluminescence immunoassay (CLIA) kit (Autobio Diagnostics Co., Zhengzhou, China, Catalog number: CL0310-2), 50 μL of the supernatant was transferred to the CLIA assay plate and 50 μL of enzyme conjugate reagent was added into each well. The plates were sealed and gently agitated for 1 hour at room temperature. The supernatant-enzyme-mixture was discarded and wells were washed 6 times with 300 μL of PBS. The residual liquid was removed by plating the CLIA plate right side down on absorbent tissue paper. 25 μL of substrates A and B were added to each well. Luminance was measured using a luminometer (Mithras LB 940 Multimode Microplate Reader) after 10 minutes incubation. Dose-response curves were generated and the $IC_{50}$ value was extrapolated by using the E-WorkBook Suite (ID Business Solutions Ltd., Guildford, UK). The $IC_{50}$ was defined as the compound concentration (or conditioned media log dilution) at which HBsAg secretion was reduced by 50% compared to the no drug control.

The compounds of the present invention were tested for their capacity to inhibit HBsAg as described herein. The Examples were tested in the above assay and found to have IC$_{50}$ below 10 μM. Particular compounds of formula I were found to have IC$_{50}$ below 1.0 μM. Results of HBsAg assay are given in Table 1.

TABLE 1

Activity data of compounds of this invention

| Example No. | IC$_{50}$ (μM) | Example No. | IC$_{50}$ (μM) | Example No. | IC$_{50}$ (μM) | Example No. | IC$_{50}$ (μM) |
|---|---|---|---|---|---|---|---|
| 1 | 0.041 | 2 | 0.088 | 3 | 0.045 | 4 | 0.182 |
| 5 | 3.48 | 6 | 0.262 | 7 | 0.19 | 8 | 0.048 |
| 9 | 0.113 | 10 | 0.569 | 11 | 6.339 | 12 | 0.74 |
| 13 | 0.085 | 14 | 0.096 | 15 | 0.041 | 16 | 0.107 |
| 17 | 1.186 | 18 | 0.912 | 19 | 0.724 | 20 | 0.824 |
| 21 | 0.582 | 22 | 0.618 | | | | |

The invention claimed is:

1. A compound of formula (I),

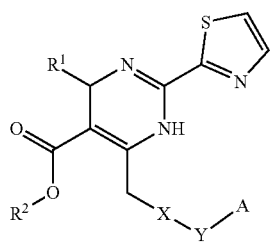

(I)

wherein:
R$^1$ is phenyl, which is unsubstituted or substituted one, two or three times by halogen or C$_{1-6}$alkyl;
R$^2$ is C$_{1-6}$alkyl;
X is —(Cy)$_{0-1}$-(L$^1$)$_{0-1}$-(L$^2$)$_{0-1}$-; wherein:
Cy is 3-20 membered heterocyclyl;
L$^1$ is C$_{1-6}$alkyl or carboxyC$_{1-6}$alkyl; and
L$^2$ is O, S, —N(R$^3$)— or —C(O)—NH—, wherein R$^3$ is H or C$_{1-6}$alkyl;
Y is a bond, C$_{1-9}$alkyl, C$_{1-6}$alkoxyC$_{1-6}$alkoxyC$_{1-6}$alkyl or carboxyC$_{1-9}$alkyl; and
A is formula (A1)

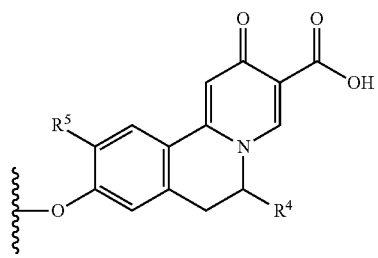

(A1)

wherein:
R$^4$ is hydrogen or C$_{1-6}$alkyl; and
R$^5$ is hydrogen or C$_{1-6}$alkoxy;
or A is formula (A2)

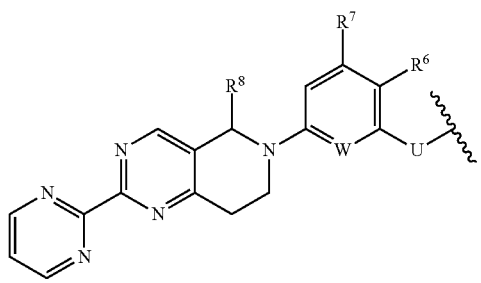

(A2)

wherein:
R$^6$ is hydrogen or halogen;
R$^7$ is hydrogen or halogen;
R$^8$ is hydrogen or C$_{1-6}$alkyl;
U is a bond or O; and
W is CH or N;
or a pharmaceutically acceptable salt thereof.

2. A compound according to claim 1, wherein:
R$^1$ is phenyl, which is one or two or three times substituted by halogen;
X is —(Cy)$_{0-1}$-(L$^1$)$_{0-1}$-(L$^2$)$_{0-1}$-, wherein:
Cy is 5-6 membered monocyclic heterocyclyl or 9-10 membered fused bicyclic heterocyclyl;
A is formula (A1), wherein R$^4$ is C$_{1-6}$alkyl, or R$^5$ is C$_{1-6}$alkoxy;
or A is formula (A2), wherein R$^7$ is halogen, and R$^8$ is C$_{1-6}$alkyl,
or a pharmaceutically acceptable salt thereof.

3. A compound according to claim 2, wherein:
R$^1$ is chlorofluorophenyl;
R$^2$ is methyl or ethyl;
X is a bond; O; —N(CH$_3$)—; piperazinyl; carboxypiperazinyl; (aminocarboxy) propylpiperazinyl; (methylamino)methylmorpholinyl; (aminocarbonyl)morpholinyl; 3-oxo-5,6,8,8a-tetrahydro-1H-imidazo[1,5-a]pyrazinyl or (aminocarbonyl)propyl-3-oxo-5,6,8,8a-tetrahydro-1H-imidazo[1,5-a]pyrazinyl;
Y is a bond, hexyl, pentyl, butyl, propyl, (ethoxyethoxy) ethyl or carboxyhexyl; and
A is:
formula (A1), wherein R$^4$ is tert-butyl, R$^5$ is methoxy;
or
formula (A2), wherein R$^6$ is hydrogen or fluoro, R$^7$ is fluoro, R$^8$ is methyl, U is a bond or O, and W is CH or N;
or a pharmaceutically acceptable salt thereof.

4. A compound according to claim 2, or a pharmaceutically acceptable salt thereof, wherein R$^1$ is phenyl, which is two times substituted by halogen.

5. A compound according to claim 4, or a pharmaceutically acceptable salt thereof, wherein R$^1$ is chlorofluorophenyl.

6. A compound according to claim 4, or a pharmaceutically acceptable salt thereof, wherein X is —(Cy)$_1$-(L$^1$)$_{0-1}$-(L$^2$)$_{0-1}$-, wherein Cy is piperazinyl, carboxypiperazinyl, morpholinyl or 3-oxo-5,6,8,8a-tetrahydro-1H-imidazo[1,5-a]pyrazinyl.

7. A compound according to claim 6, or a pharmaceutically acceptable salt thereof, wherein X is piperazinyl, carboxypiperazinyl, or (aminocarbonyl)propyl-3-oxo-5,6,8,8a-tetrahydro-1H-imidazo[1,5-a]pyrazinyl.

8. A compound according to claim 6, or a pharmaceutically acceptable salt thereof, wherein Y is a bond, $C_{1-9}$alkyl or $C_{1-6}$alkoxy$C_{1-6}$alkoxy$C_{1-6}$alkyl.

9. A compound according to claim 8, or a pharmaceutically acceptable salt thereof, wherein Y is a bond, hexyl, propyl, or (ethoxyethoxy)ethyl.

10. A compound according to claim 1, selected from:

6-tert-butyl-9-[6-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylic acid;

6-tert-butyl-9-[5-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]pentoxy]-10-methoxy-2-oxo-6,7-dihydrobenzo[a]quinolizine-3-carboxylic acid;

6-tert-butyl-9-[4-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]butoxy]-10-methoxy-2-oxo-6,7-dihydrobenzo[a]quinolizine-3-carboxylic acid;

6-tert-butyl-9-[3-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]propoxy]-10-methoxy-2-oxo-6,7-dihydrobenzo[a]quinolizine-3-carboxylic acid;

6-tert-butyl-9-[3-[2-carboxy-4-[[(4R)-4-(2-chloro-4-fluoro-phenyl)-5-methoxycarbonyl-2-thiazol-2-yl-1,4-dihydropyrimidin-6-yl]methyl]piperazin-1-yl]propoxy]-10-methoxy-2-oxo-6,7-dihydrobenzo[a]quinolizine-3-carboxylic acid;

6-tert-butyl-9-[6-[3-carboxy-4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylic acid;

6-tert-butyl-9-[6-[2-carboxy-4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylic acid;

6-tert-butyl-9-[6-[7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]hexoxy]-10-methoxy-2-oxo-6,7-dihydrobenzo[a]quinolizine-3-carboxylic acid;

6-tert-butyl-9-[6-[[(4R)-4-(2-chloro-4-fluoro-phenyl)-5-methoxycarbonyl-2-thiazol-2-yl-1,4-dihydropyrimidin-6-yl]methyl-methyl-amino]hexoxy]-10-methoxy-2-oxo-6,7-dihydrobenzo[a]quinolizine-3-carboxylic acid;

6-tert-butyl-9-[2-[2-[2-[[(3S)-4-[[(4R)-4-(2-chloro-4-fluoro-phenyl)-5-methoxycarbonyl-2-thiazol-2-yl-1,4-dihydropyrimidin-6-yl]methyl]morpholine-3-carbonyl]amino]ethoxy]ethoxy]ethoxy]-10-methoxy-2-oxo-6,7-dihydrobenzo[a]quinolizine-3-carboxylic acid;

6-tert-butyl-9-[2-[2-[2-[2-carboxy-4-[[(4R)-4-(2-chloro-4-fluoro-phenyl)-5-methoxycarbonyl-2-thiazol-2-yl-1,4-dihydropyrimidin-6-yl]methyl]piperazin-1-yl]ethoxy]ethoxy]ethoxy]-10-methoxy-2-oxo-6,7-dihydrobenzo[a]quinolizine-3-carboxylic acid;

6-tert-butyl-9-[4-carboxy-6-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]hexoxy]-10-methoxy-2-oxo-6,7-dihydrobenzo[a]quinolizine-3-carboxylic acid;

6-tert-butyl-9-[6-[[(3S)-4-[[(4R)-4-(2-chloro-4-fluoro-phenyl)-5-methoxycarbonyl-2-thiazol-2-yl-1,4-dihydropyrimidin-6-yl]methyl]morpholine-3-carbonyl]amino]hexoxy]-10-methoxy-2-oxo-6,7-dihydrobenzo[a]quinolizine-3-carboxylic acid;

6-tert-butyl-9-[6-[[4-(2-chloro-4-fluoro-phenyl)-5-ethoxycarbonyl-2-thiazol-2-yl-1,4-dihydropyrimidin-6-yl]methoxy]hexoxy]-10-methoxy-2-oxo-6,7-dihydrobenzo[a]quinolizine-3-carboxylic acid;

9-[6-[[3-[(8aS)-7-[[(4R)-4-(2-chloro-3-fluoro-phenyl)-5-ethoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-2,2-dimethyl-propanoyl]amino]hexoxy]-6-tert-butyl-10-methoxy-2-oxo-6,7-dihydrobenzo[a]quinolizine-3-carboxylic acid;

9-[6-[[4-[(8aS)-7-[[(4R)-4-(2-chloro-4-fluoro-phenyl)-5-methoxycarbonyl-2-thiazol-2-yl-1,4-dihydropyrimidin-6-yl]methyl]-3-oxo-5,6,8,8a-tetrahydro-1H-imidazo[1,5-a]pyrazin-2-yl]-3,3-dimethyl-butanoyl]amino]hexoxy]-6-tert-butyl-10-methoxy-2-oxo-6,7-dihydrobenzo[a]quinolizine-3-carboxylic acid;

methyl (4R)-6-[[(8aS)-2-[4-[6-[2,3-difluoro-5-[5-methyl-2-pyrimidin-2-yl-7,8-dihydro-5H-pyrido[4,3-d]pyrimidin-6-yl]phenoxy]hexylamino]-2,2-dimethyl-4-oxo-butyl]-3-oxo-5,6,8,8a-tetrahydro-1H-imidazo[1,5-a]pyrazin-7-yl]methyl]-4-(2-chloro-4-fluoro-phenyl)-2-thiazol-2-yl-1,4-dihydropyrimidine-5-carboxylate;

methyl (4R)-4-(2-chloro-4-fluoro-phenyl)-6-[[(3S)-3-[6-[2,3-difluoro-5-(5-methyl-2-pyrimidin-2-yl-7,8-dihydro-5H-pyrido[4,3-d]pyrimidin-6-yl)phenoxy]hexylcarbamoyl]morpholin-4-yl]methyl]-2-thiazol-2-yl-1,4-dihydropyrimidine-5-carboxylate;

methyl (4R)-4-(2-chloro-4-fluoro-phenyl)-6-[[(3R)-3-[[6-[2,3-difluoro-5-(5-methyl-2-pyrimidin-2-yl-7,8-dihydro-5H-pyrido[4,3-d]pyrimidin-6-yl)phenoxy]hexyl-methyl-amino]methyl]morpholin-4-yl]methyl]-2-thiazol-2-yl-1,4-dihydropyrimidine-5-carboxylate;

methyl (4R)-4-(2-chloro-4-fluoro-phenyl)-6-[[2,3-difluoro-5-(5-methyl-2-pyrimidin-2-yl-7,8-dihydro-5H-pyrido[4,3-d]pyrimidin-6-yl)phenoxy]methyl]-2-thiazol-2-yl-1,4-dihydropyrimidine-5-carboxylate;

(2R)-4-[4-[[(4R)-4-(2-chloro-4-fluoro-phenyl)-5-methoxycarbonyl-2-thiazol-2-yl-1,4-dihydropyrimidin-6-yl]methyl]piperazin-1-yl]-2-[6-[2,3-difluoro-5-(5-methyl-2-pyrimidin-2-yl-7,8-dihydro-5H-pyrido[4,3-d]pyrimidin-6-yl)phenoxy]hexylamino]butanoic acid; and 4-[[(4R)-4-(2-chloro-4-fluoro-phenyl)-5-methoxycarbonyl-2-thiazol-2-yl-1,4-dihydropyrimidin-6-yl]methyl]-1-[4-fluoro-6-[5-methyl-2-pyrimidin-2-yl-7,8-dihydro-5H-pyrido[4,3-d]pyrimidin-6-yl]-2-pyridyl]piperazine-2-carboxylic acid;

or a pharmaceutically acceptable salt thereof.

11. A process for preparing a compound according to claim 1, or a pharmaceutically acceptable salt thereof, the process comprising any one of the following steps:

(a) hydrolysis of a compound of formula (VI), in the presence of a base;

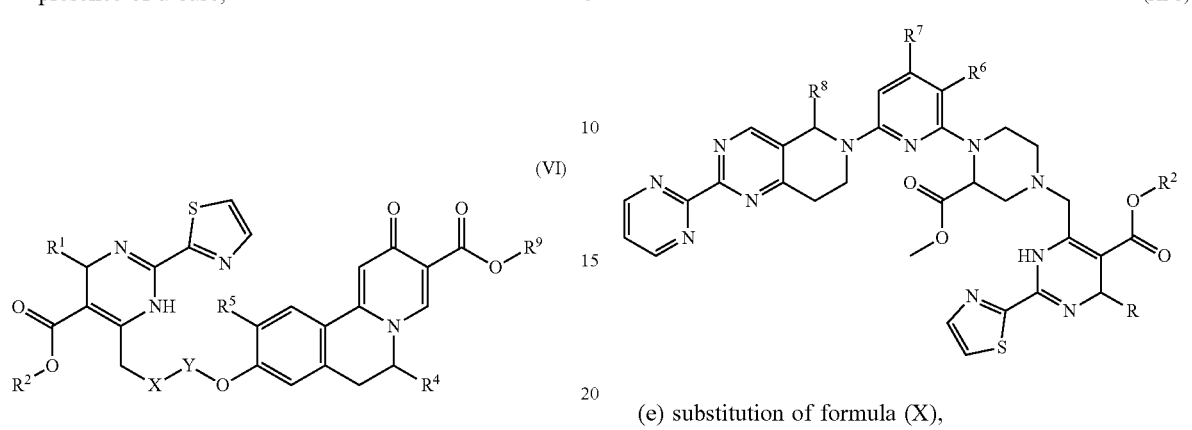

(b) hydrolysis of a compound of formula (V-2),

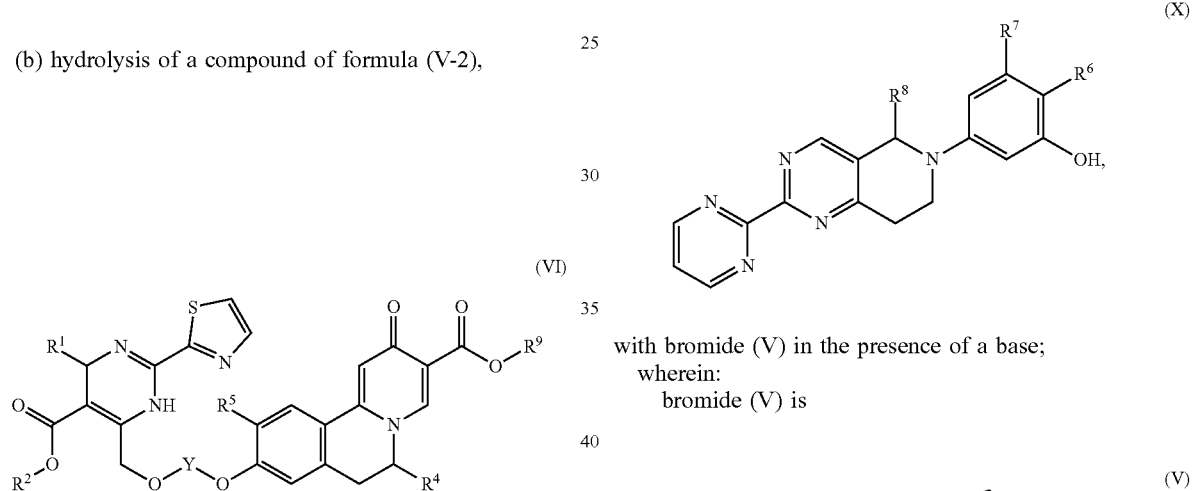

(c) de-protection and substitution of a compound of formula (X-2), with bromide (V) in the presence of a base;

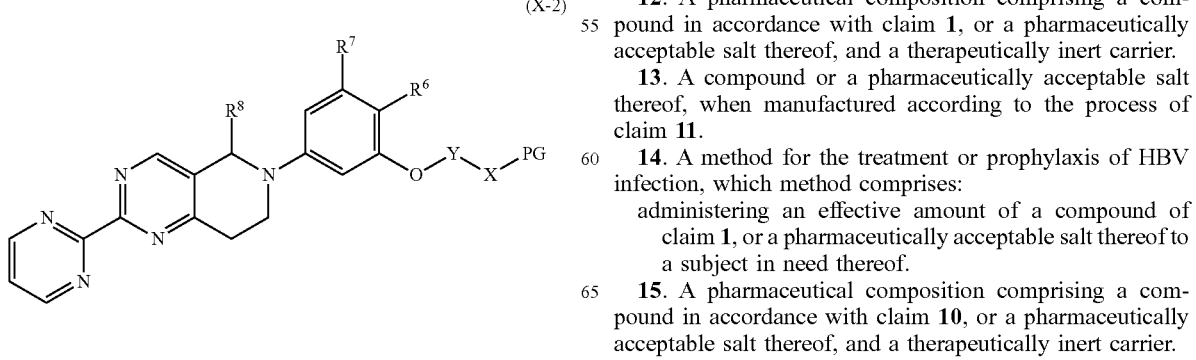

(d) hydrolysis of a compound of formula (XI-3), in the presence of a base;

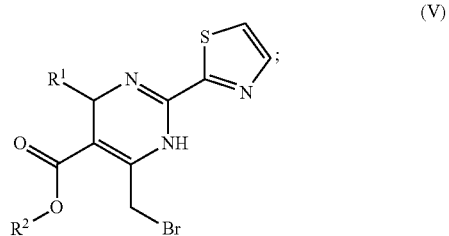

(e) substitution of formula (X), with bromide (V) in the presence of a base;
wherein:
bromide (V) is PG is Boc; and
$R^9$ is $C_{1-6}$alkyl.

12. A pharmaceutical composition comprising a compound in accordance with claim 1, or a pharmaceutically acceptable salt thereof, and a therapeutically inert carrier.

13. A compound or a pharmaceutically acceptable salt thereof, when manufactured according to the process of claim 11.

14. A method for the treatment or prophylaxis of HBV infection, which method comprises:
administering an effective amount of a compound of claim 1, or a pharmaceutically acceptable salt thereof to a subject in need thereof.

15. A pharmaceutical composition comprising a compound in accordance with claim 10, or a pharmaceutically acceptable salt thereof, and a therapeutically inert carrier.

16. A method for the treatment or prophylaxis of HBV infection, which method comprises:
   administering an effective amount of a compound of claim 10, or a pharmaceutically acceptable salt thereof to a subject in need thereof.

* * * * *